United States Patent
Zhu et al.

(10) Patent No.: US 12,116,627 B2
(45) Date of Patent: Oct. 15, 2024

(54) METHODS OF SEQUENCING AND PRODUCING NUCLEIC ACID SEQUENCES

(71) Applicant: Tsinghua University, Beijing (CN)

(72) Inventors: Ting Zhu, Beijing (CN); Xianyu Liu, Beijing (CN); Wenjun Jiang, Beijing (CN); Min Wang, Beijing (CN)

(73) Assignee: Tsinghua University, Beijing (CN)

( * ) Notice: Subject to any disclaimer, the term of this patent is extended or adjusted under 35 U.S.C. 154(b) by 1023 days.

(21) Appl. No.: 17/034,024

(22) Filed: Sep. 28, 2020

(65) Prior Publication Data

US 2021/0010078 A1    Jan. 14, 2021

Related U.S. Application Data

(63) Continuation of application No. PCT/IB2019/052752, filed on Apr. 4, 2019.

(60) Provisional application No. 62/652,915, filed on Apr. 5, 2018.

(51) Int. Cl.
   *C12Q 1/6869* (2018.01)
   *C12N 15/10* (2006.01)
   *C12Q 1/6806* (2018.01)

(52) U.S. Cl.
   CPC ....... *C12Q 1/6869* (2013.01); *C12N 15/1096* (2013.01); *C12Q 1/6806* (2013.01)

(58) Field of Classification Search
   CPC ............... C12Q 1/6869; C12Q 1/6806; C12Q 2523/107; C12Q 2527/125; C12Q 2563/101; C12Q 2563/107; C12Q 2565/125; C12N 15/1096; C12N 15/10
   See application file for complete search history.

(56) References Cited

U.S. PATENT DOCUMENTS 6,605,713 B1    8/2003  Furste et al.
6,902,891 B2    6/2005  Laayoun et al.

FOREIGN PATENT DOCUMENTS

| CA | 2045891 | 7/2003 |
| CN | 101575639 | 11/2009 |
| CN | 104178467 | 12/2014 |
| CN | 105985949 | 10/2016 |
| DE | 3839397 | 5/1990 |
| JP | 2011068651 | * 4/2011 |
| WO | WO 2010/049156 | 5/2010 |
| WO | WO 2017/177759 | 10/2017 |
| WO | WO 2019/193526 | 10/2019 |

OTHER PUBLICATIONS

Liu et al, Sequencing Mirror-Image DNA Chemically, Cell Chemical Biology, 25, 1151-1156, Post Art (Year: 2018).*
Communication Pursuant to Article 94(3) EPC Dated Mar. 17, 2023 From the European Patent Office Re. Application No. 19780836.3 (17 Pages).
Franca et al. "A Review of DNA Sequencing Techniques", Quarterly Reviews of Biophysics, 35(2): 169-200, Aug. 20, 2002.
Supplementary European Search Report and the European Search Opinion Dated Nov. 17, 2021 From the European Patent Office Re. Application No. 19780836.3. (12 Pages).
Frauendorf et al. "Internal 32P-labeling of L-Deoxyoligonucleotides", Nucleic Acids Research, 31(7 e34):1-4, XP055334943, Apr. 1, 2003.
Liu et al. "Sequencing Mirror-Image DNA Chemically", Cell Chemical Biology, 25(9):1151-1156, XP55858327A, Sep. 20, 2018.
Maxam et al. "A New Method for Sequencing DNA", Proceedings of the National Academy of Sciences, 74(2):560-564, XP614976A, Feb. 1, 1977.
Pichersky "DNA Sequencing by the Chemical Method", Basic DNA And RNA Protocols: Methods in Molecular Biology, 58:447-451, XP9531108A , Feb. 19, 1996.
International Preliminary Report on Patentability Dated Oct. 15, 2020 From the International Bureau of WIPO Re. Application No. PCT/IB2019/052752. (6 Pages).
International Search Report and the Written Opinion Dated Aug. 20, 2019 From the International Searching Authority Re. Application No. PCT/IB2019/052752. (10 Pages).
Derrington et al. "Sub-Angstrom Single-Molecule Measurements of Motor Proteins Using A Nanopore", Nature Biotechnology, 33(10): 1073-1075, October 215.
Jiang et al. "Mirror-Image Polymerase Chain Reaction", Cell Discovery, 3: 17037-1-17037-7, Published Online Oct. 17, 2017.
Pech et al. "A Thermostable D-Polymerase for Mirror-Image PCR", Nucleic Acids Research, 45(7): 3997-4005, Published Online Feb. 2, 2017.
Wang et al. "A Synthetic Molecular System Capable of Mirror-Image Genetic Replication and Transcription", Nature Chemistry, 8(7): 698-704, Published Online May 16, 2016.
Wang et al. "Mirror-Image Gene Transcription and Reverse Transcription", Chem, 5: 1-10, Published Online Feb. 7, 2019.

(Continued)

*Primary Examiner* — Narayan K Bhat

(57)  ABSTRACT

Methods of sequencing and producing nucleic acid sequences are provided. Accordingly there are provided methods of sequencing a nucleic acid sequence comprising L-nucleotides comprising subjecting the nucleic acid sequence comprising the L-nucleotides to a chemical sequencing method. Also provided is a method of reverse transcribing a ribose nucleic acid sequence into a deoxyribose nucleic acid sequence comprising catalyzing reverse transcription of the ribose nucleic acid sequence with a *Sulfolobus solfataricus* P2 DNA polymerase IV (Dpo4).

22 Claims, 13 Drawing Sheets

Figure 1A:
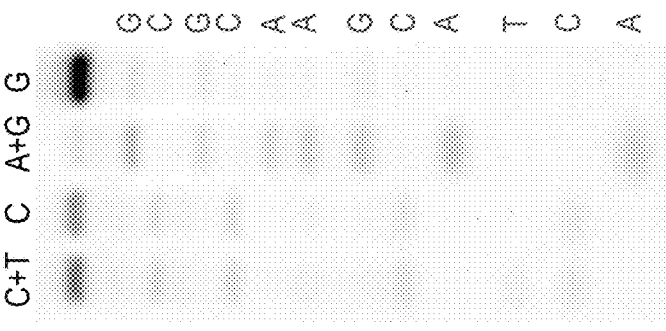

Specification includes a Sequence Listing.

(56) References Cited

OTHER PUBLICATIONS

Williams et al. "Bioactive and Nuclease-Resistant L-DNA Ligand of Vasopressin", Proc. Natl. Acad. Sci. USA, 94(21): 11285-11290, Oct. 14, 1997.
Xu et al. "Total Chemical Synthesis of A Thermostable Enzyme Capable of Polymerase Chain Reaction", Cell Discovery, 3: 17008-1-17008-10, Published Online Feb. 28, 2017.
Yatime et al. "Structural Basis for the Targeting of Complement Anaphylatoxin C5a Using A Mixed L-RNA/L-DNA Aptamer", Nature Communications, 6: 6481-1-6481-13, Apr. 22, 2015.
Turner et al. "Methods for L-Ribooligonucleotide Sequence Determination Using LCMS", Nucleic Acids Research, 39(21): e147, 13P., Sep. 24, 2011.
Supplementary European Search Report and the European Search Opinion Dated Feb. 17, 2022 From the European Patent Office Re. Application No. 1'9780836.3. (11 Pages).
Communication Pursuant to Article 94(3) EPC Dated Jan. 24, 2024 From the European Patent Office Re. Application No. 19780836.3 (4 Pages).

* cited by examiner

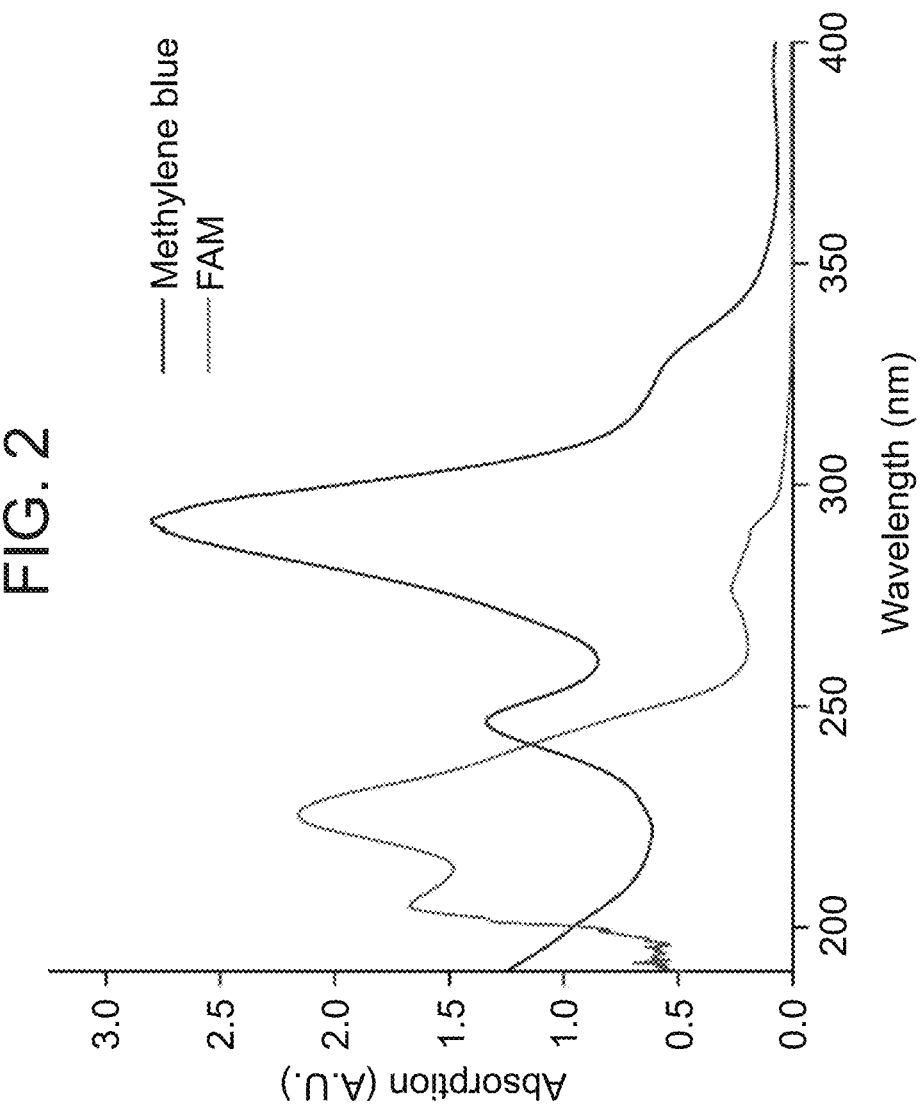

FIG. 3A

\*5'-ACTACGAACGCG-3' SEQ ID NO:1

C+T     C     A+G     G

\*ACTACGAACG(C)    \*ACTACGAACGC(G) \*ACTACGAACGC(G)
\*ACTACGAACG(C)               \*ACTACGAAC(G)    \*ACTACGAAC(G)
\*ACTACGAA(C)    \*ACTACGAA(C)
                          \*ACTACGA(A)
                          \*ACTACG(A)
\*ACTA(C)    \*ACTA(C)                 \*ACTAC(G)
                          \*ACT(A)
\*AC(T)
\*A(C)        \*A(C)
                          \*(A)

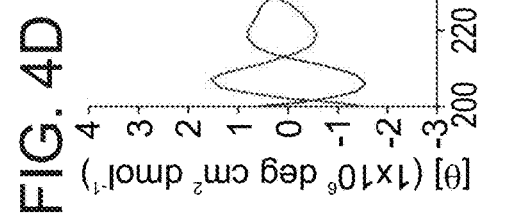
FIG. 4B
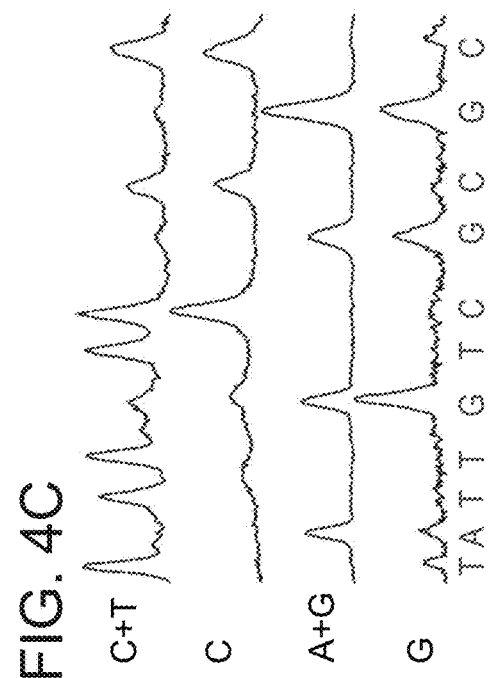
FIG. 4D
FIG. 4A
FIG. 4C

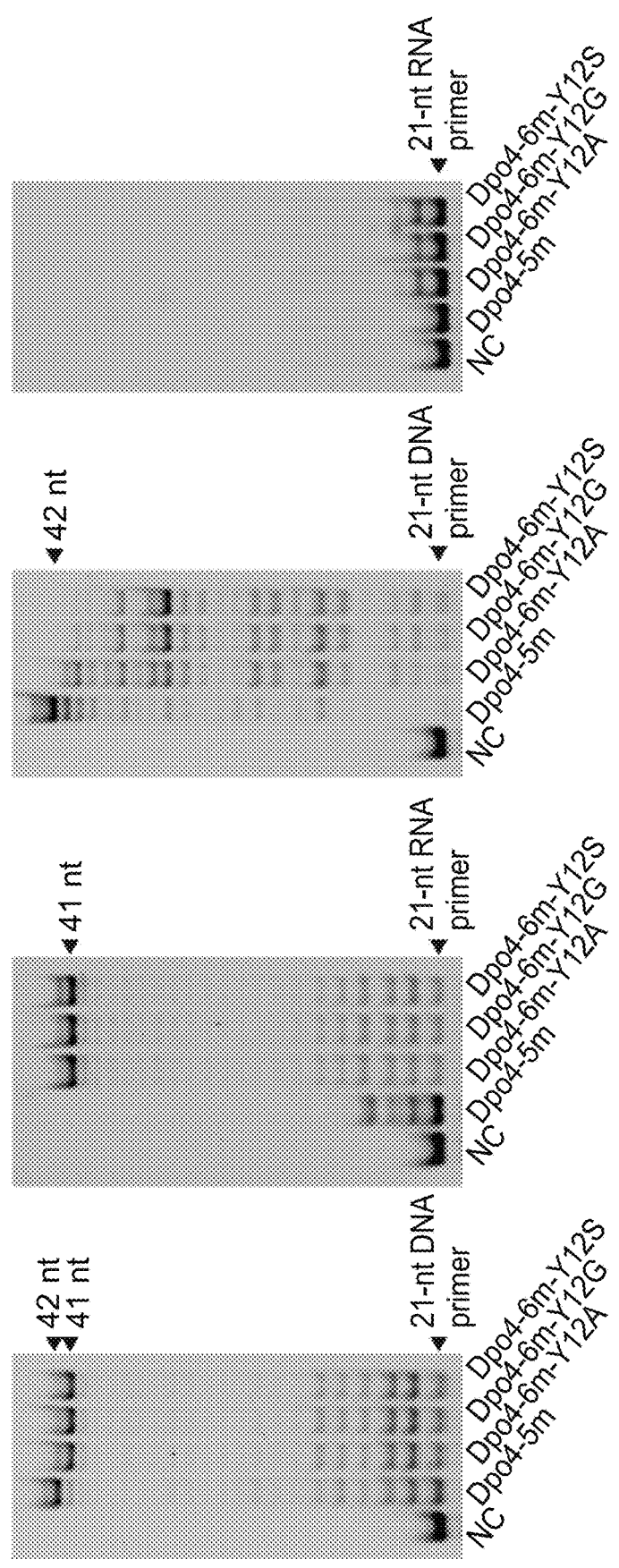

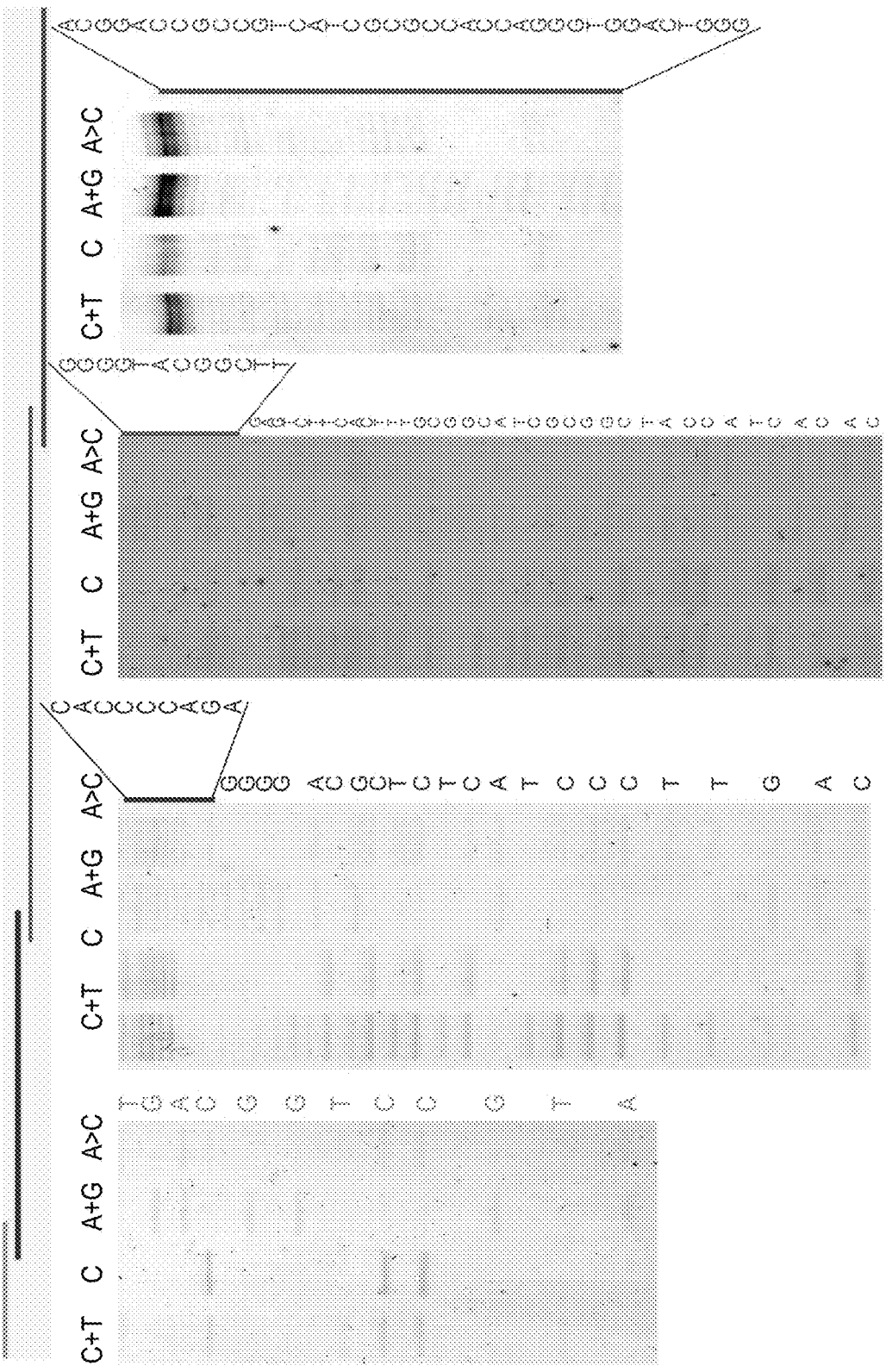

L-DNA primer

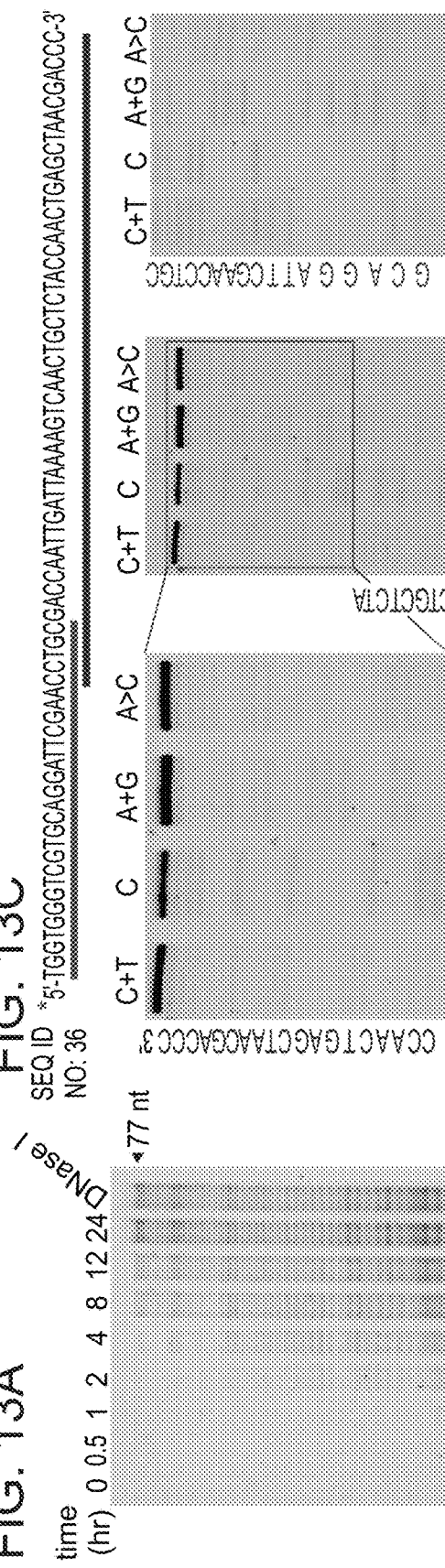
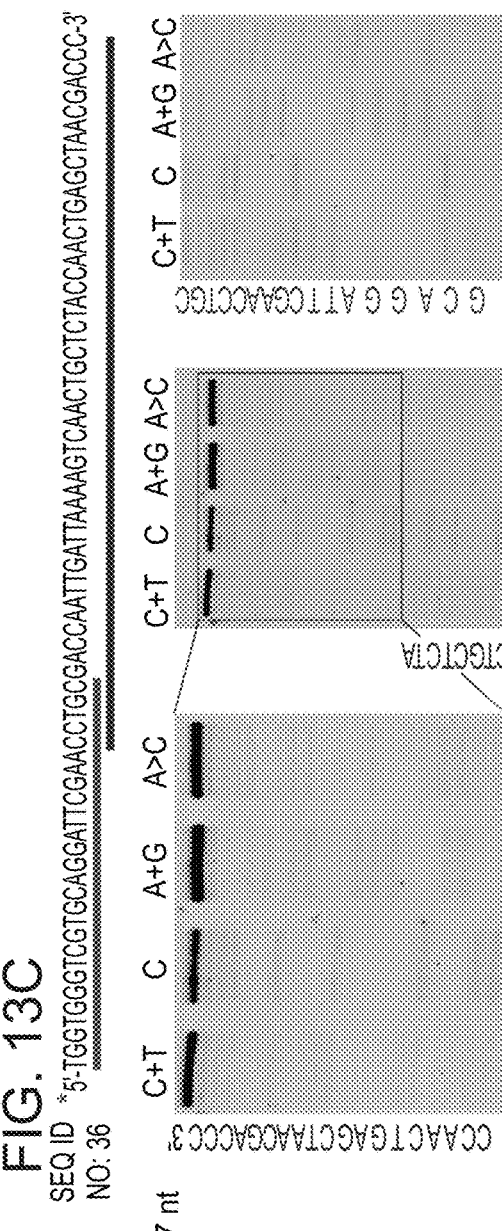
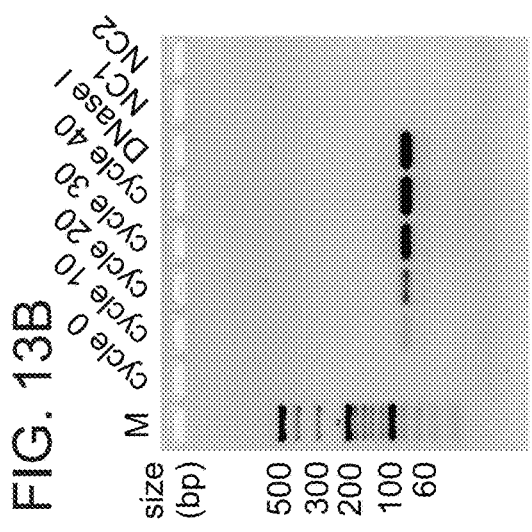
FIG. 13A
FIG. 13B
FIG. 13C

SEQUENCE LISTING

```
<160> NUMBER OF SEQ ID NOS: 36

<210> SEQ ID NO 1
<211> LENGTH: 12
<212> TYPE: DNA
<213> ORGANISM: Artificial sequence
<220> FEATURE:
<223> OTHER INFORMATION: 5'-fluorescein amidite (FAM) labeled
      12-nucleotides (nt) L-DNA oligonucleotide (oligo)
<220> FEATURE:
<221> NAME/KEY: misc_feature
<222> LOCATION: (1)..(1)
<223> OTHER INFORMATION: 5' FAM conjugated

<400> SEQUENCE: 1
actacgaacg cg                                                           12

<210> SEQ ID NO 2
<211> LENGTH: 11
<212> TYPE: DNA
<213> ORGANISM: Artificial sequence
<220> FEATURE:
<223> OTHER INFORMATION: 5'-FAM labeled 11-nt L-DNA oligo
<220> FEATURE:
<221> NAME/KEY: misc_feature
<222> LOCATION: (1)..(1)
<223> OTHER INFORMATION: 5' FAM conjugated

<400> SEQUENCE: 2
cgcgctgtta t                                                            11

<210> SEQ ID NO 3
<211> LENGTH: 25
<212> TYPE: DNA
<213> ORGANISM: Artificial sequence
<220> FEATURE:
<223> OTHER INFORMATION: 5'-FAM labeled 25-nucleotides (nt) L-DNA
      oligonucleotide (oligo)
<220> FEATURE:
<221> NAME/KEY: misc_feature
<222> LOCATION: (1)..(1)
<223> OTHER INFORMATION: 5'-FAM conjugated

<400> SEQUENCE: 3
atgcctggca gttccctact ctcgc                                             25
```

```
<210> SEQ ID NO 4
<211> LENGTH: 55
<212> TYPE: DNA
<213> ORGANISM: Artificial sequence
<220> FEATURE:
<223> OTHER INFORMATION: 5'-FAM labeled 55-nt L-DNA aptamer
<220> FEATURE:
<221> NAME/KEY: misc_feature
<222> LOCATION: (1)..(1)
<223> OTHER INFORMATION: 5'-FAM conjugated

<400> SEQUENCE: 4
tcacgtgcat gatagacggc gaagccgtcg agttgctgtg tgccgatgca cgtga      55

<210> SEQ ID NO 5
<211> LENGTH: 46
<212> TYPE: RNA
<213> ORGANISM: Artificial sequence
<220> FEATURE:
<223> OTHER INFORMATION: 5' FAM-labeled 46-nt L-ribozyme RNA
<220> FEATURE:
<221> NAME/KEY: misc_feature
<222> LOCATION: (1)..(1)
<223> OTHER INFORMATION: 5' FAM cunjugated

<400> SEQUENCE: 5
ggaucgaaag auuuccgcau ccccgaaagg guacauggcg uuaggu                46

<210> SEQ ID NO 6
<211> LENGTH: 352
<212> TYPE: PRT
<213> ORGANISM: Sulfolobus solfataricus

<400> SEQUENCE: 6
```

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Ala Val Ala Thr Ala Asn Tyr
        35                  40                  45

Glu Ala Arg Lys Phe Gly Val Lys Ala Gly Ile Pro Ile Val Glu Ala
    50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr

```
                210                 215                 220
Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Val Thr Glu Asp Leu Asp Ile Val Ser Arg Gly Arg Thr Phe Pro His
            290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 7
<211> LENGTH: 416
<212> TYPE: PRT
<213> ORGANISM: Sulfolobus solfataricus

<400> SEQUENCE: 7

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
        50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
            130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240
```

-continued

```
Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Val Thr Glu Asp Leu Asp Ile Val Ser Arg Gly Arg Thr Phe Pro His
    290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

Gln Ala Glu Leu Cys Ala Asp Pro Lys Glu Leu Trp Val Gln Gln Leu
        355                 360                 365

Met Gln His Leu Asp Lys Thr Pro Ser Pro Gln Lys Pro Ala Gln Gly
    370                 375                 380

Cys Arg Lys Asp Arg Gly Ala Ser Lys Thr Gly Lys Lys Gly Lys Gly
385                 390                 395                 400

Ser Lys Gly Cys Lys Arg Thr Glu Arg Ser Gln Thr Pro Lys Gly Pro
                405                 410                 415

<210> SEQ ID NO 8
<211> LENGTH: 358
<212> TYPE: PRT
<213> ORGANISM: Artificial sequence
<220> FEATURE:
<223> OTHER INFORMATION: Dpo4 wt with 5' His tag

<400> SEQUENCE: 8

His His His His His His Met Ile Val Leu Phe Val Asp Phe Asp Tyr
1               5                   10                  15

Phe Tyr Ala Gln Val Glu Glu Val Leu Asn Pro Ser Leu Lys Gly Lys
            20                  25                  30

Pro Val Val Val Cys Val Phe Ser Gly Arg Phe Glu Asp Ser Gly Ala
        35                  40                  45

Val Ala Thr Ala Asn Tyr Glu Ala Arg Lys Phe Gly Val Lys Ala Gly
    50                  55                  60

Ile Pro Ile Val Glu Ala Lys Lys Ile Leu Pro Asn Ala Val Tyr Leu
65                  70                  75                  80

Pro Met Arg Lys Glu Val Tyr Gln Gln Val Ser Ser Arg Ile Met Asn
                85                  90                  95

Leu Leu Arg Glu Tyr Ser Glu Lys Ile Glu Ile Ala Ser Ile Asp Glu
            100                 105                 110

Ala Tyr Leu Asp Ile Ser Asp Lys Val Arg Asp Tyr Arg Glu Ala Tyr
        115                 120                 125

Asn Leu Gly Leu Glu Ile Lys Asn Lys Ile Leu Glu Lys Glu Lys Ile
    130                 135                 140

Thr Val Thr Val Gly Ile Ser Lys Asn Lys Val Phe Ala Lys Ile Ala
145                 150                 155                 160

Ala Asp Met Ala Lys Pro Asn Gly Ile Lys Val Ile Asp Asp Glu Glu
                165                 170                 175

Val Lys Arg Leu Ile Arg Glu Leu Asp Ile Ala Asp Val Pro Gly Ile
            180                 185                 190
```

```
Gly Asn Ile Thr Ala Glu Lys Leu Lys Lys Leu Gly Ile Asn Lys Leu
            195                 200                 205

Val Asp Thr Leu Ser Ile Glu Phe Asp Lys Leu Lys Gly Met Ile Gly
    210                 215                 220

Glu Ala Lys Ala Lys Tyr Leu Ile Ser Leu Ala Arg Asp Glu Tyr Asn
225                 230                 235                 240

Glu Pro Ile Arg Thr Arg Val Arg Lys Ser Ile Gly Arg Ile Val Thr
                245                 250                 255

Met Lys Arg Asn Ser Arg Asn Leu Glu Ile Lys Pro Tyr Leu Phe
                260                 265                 270

Arg Ala Ile Glu Glu Ser Tyr Tyr Lys Leu Asp Lys Arg Ile Pro Lys
                275                 280                 285

Ala Ile His Val Val Ala Val Thr Glu Asp Leu Asp Ile Val Ser Arg
            290                 295                 300

Gly Arg Thr Phe Pro His Gly Ile Ser Lys Glu Thr Ala Tyr Ser Glu
305                 310                 315                 320

Ser Val Lys Leu Leu Gln Lys Ile Leu Glu Glu Asp Glu Arg Lys Ile
                325                 330                 335

Arg Arg Ile Gly Val Arg Phe Ser Lys Phe Ile Glu Ala Ile Gly Leu
            340                 345                 350

Asp Lys Phe Phe Asp Thr
            355

<210> SEQ ID NO 9
<211> LENGTH: 352
<212> TYPE: PRT
<213> ORGANISM: Artificial sequence
<220> FEATURE:
<223> OTHER INFORMATION: Dpo4 wt without 5' His tag

<400> SEQUENCE: 9

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
        50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190
```

```
Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
        210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Val Thr Glu Asp Leu Asp Ile Val Ser Arg Gly Arg Thr Phe Pro His
290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 10
<211> LENGTH: 358
<212> TYPE: PRT
<213> ORGANISM: Artificial sequence
<220> FEATURE:
<223> OTHER INFORMATION: Dpo4-5m with 5' His tag
<220> FEATURE:
<221> NAME/KEY: misc_feature
<222> LOCATION: (7)..(7)
<223> OTHER INFORMATION: Xaa is isosteric methionine analog norleucine
<220> FEATURE:
<221> NAME/KEY: misc_feature
<222> LOCATION: (82)..(82)
<223> OTHER INFORMATION: Xaa is isosteric methionine analog norleucine
<220> FEATURE:
<221> NAME/KEY: misc_feature
<222> LOCATION: (95)..(95)
<223> OTHER INFORMATION: Xaa is isosteric methionine analog norleucine
<220> FEATURE:
<221> NAME/KEY: misc_feature
<222> LOCATION: (163)..(163)
<223> OTHER INFORMATION: Xaa is isosteric methionine analog norleucine
<220> FEATURE:
<221> NAME/KEY: misc_feature
<222> LOCATION: (222)..(222)
<223> OTHER INFORMATION: Xaa is isosteric methionine analog norleucine
<220> FEATURE:
<221> NAME/KEY: misc_feature
<222> LOCATION: (257)..(257)
<223> OTHER INFORMATION: Xaa is isosteric methionine analog norleucine

<400> SEQUENCE: 10

His His His His His His Xaa Ile Val Leu Phe Val Asp Phe Asp Tyr
1               5                   10                  15

Phe Tyr Ala Gln Val Glu Glu Val Leu Asn Pro Ser Leu Lys Gly Lys
            20                  25                  30

Pro Val Val Val Ser Val Phe Ser Gly Arg Phe Glu Asp Ser Gly Ala
        35                  40                  45

Val Ala Thr Ala Asn Tyr Glu Ala Arg Lys Phe Gly Val Lys Ala Gly
    50                  55                  60

Ile Pro Ile Val Glu Ala Lys Lys Ile Leu Pro Asn Ala Val Tyr Leu
65                  70                  75                  80
```

```
Pro Xaa Arg Lys Glu Val Tyr Gln Gln Val Ser Cys Arg Ile Xaa Asn
            85                  90                  95

Leu Leu Arg Glu Tyr Ser Glu Lys Ile Glu Ile Ala Ser Ile Asp Glu
            100                 105                 110

Ala Tyr Leu Asp Ile Ser Asp Lys Val Arg Asp Tyr Arg Glu Ala Tyr
            115                 120                 125

Ala Leu Gly Leu Glu Ile Lys Asn Lys Ile Leu Glu Lys Glu Lys Ile
            130                 135                 140

Thr Val Thr Val Gly Ile Ser Lys Asn Lys Val Phe Ala Lys Ile Ala
145                 150                 155                 160

Ala Asp Xaa Ala Lys Pro Asn Gly Ile Lys Val Ile Asp Asp Glu Glu
            165                 170                 175

Val Lys Arg Leu Ile Arg Glu Leu Asp Ile Ala Asp Val Pro Gly Ile
            180                 185                 190

Gly Asn Ile Thr Ala Glu Lys Leu Lys Lys Leu Gly Ile Asn Lys Leu
            195                 200                 205

Val Asp Thr Leu Ala Ile Glu Phe Asp Lys Leu Lys Gly Xaa Ile Gly
            210                 215                 220

Glu Ala Lys Ala Lys Tyr Leu Ile Ser Leu Ala Arg Asp Glu Tyr Asn
225                 230                 235                 240

Glu Pro Ile Arg Thr Arg Val Arg Lys Ser Ile Gly Arg Ile Val Thr
            245                 250                 255

Xaa Lys Arg Asn Ser Arg Asn Leu Glu Ile Lys Pro Tyr Leu Phe
            260                 265                 270

Arg Ala Ile Glu Glu Ser Tyr Tyr Lys Leu Asp Lys Arg Ile Pro Lys
            275                 280                 285

Ala Ile His Val Val Ala Val Thr Glu Asp Leu Asp Ile Val Ser Arg
            290                 295                 300

Gly Arg Thr Phe Pro His Gly Ile Ser Lys Glu Thr Ala Tyr Ala Glu
305                 310                 315                 320

Ser Val Lys Leu Leu Gln Lys Ile Leu Glu Asp Glu Arg Lys Ile
            325                 330                 335

Arg Arg Ile Gly Val Arg Phe Ser Lys Phe Ile Glu Ala Ile Gly Leu
            340                 345                 350

Asp Lys Phe Phe Asp Thr
            355

<210> SEQ ID NO 11
<211> LENGTH: 352
<212> TYPE: PRT
<213> ORGANISM: Artificial sequence
<220> FEATURE:
<223> OTHER INFORMATION: Dpo4-5m without His tag
<220> FEATURE:
<221> NAME/KEY: misc_feature
<222> LOCATION: (1)..(1)
<223> OTHER INFORMATION: Xaa is isosteric methionine analog norleucine
<220> FEATURE:
<221> NAME/KEY: misc_feature
<222> LOCATION: (76)..(76)
<223> OTHER INFORMATION: Xaa is isosteric methionine analog norleucine
<220> FEATURE:
<221> NAME/KEY: misc_feature
<222> LOCATION: (89)..(89)
<223> OTHER INFORMATION: Xaa is isosteric methionine analog norleucine
<220> FEATURE:
<221> NAME/KEY: misc_feature
<222> LOCATION: (157)..(157)
<223> OTHER INFORMATION: Xaa is isosteric methionine analog norleucine
<220> FEATURE:
<221> NAME/KEY: misc_feature
```

```
<222> LOCATION: (216)..(216)
<223> OTHER INFORMATION: Xaa is isosteric methionine analog norleucine
<220> FEATURE:
<221> NAME/KEY: misc_feature
<222> LOCATION: (251)..(251)
<223> OTHER INFORMATION: Xaa is isosteric methionine analog norleucine

<400> SEQUENCE: 11
```

Xaa Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Ser Val
            20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
50                  55                  60

Lys Lys Ile Leu Pro Asn Ala Val Tyr Leu Pro Xaa Arg Lys Glu Val
65                  70                  75                  80

Tyr Gln Gln Val Ser Cys Arg Ile Xaa Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Ala Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Lys Ile Ala Ala Asp Xaa Ala Lys Pro
145                 150                 155                 160

Asn Gly Ile Lys Val Ile Asp Asp Glu Glu Val Lys Arg Leu Ile Arg
            165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ala Ile
            195                 200                 205

Glu Phe Asp Lys Leu Lys Gly Xaa Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Xaa Lys Arg Asn Ser Arg
            245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Val Thr Glu Asp Leu Asp Ile Val Ser Arg Gly Arg Thr Phe Pro His
290                 295                 300

Gly Ile Ser Lys Glu Thr Ala Tyr Ala Glu Ser Val Lys Leu Leu Gln
305                 310                 315                 320

Lys Ile Leu Glu Glu Asp Glu Arg Lys Ile Arg Arg Ile Gly Val Arg
            325                 330                 335

Phe Ser Lys Phe Ile Glu Ala Ile Gly Leu Asp Lys Phe Phe Asp Thr
            340                 345                 350

```
<210> SEQ ID NO 12
<211> LENGTH: 358
<212> TYPE: PRT
```

```
<213> ORGANISM: Artificial sequence
<220> FEATURE:
<223> OTHER INFORMATION: Dpo4-6m-Y12S with 5' His tag
<220> FEATURE:
<221> NAME/KEY: misc_feature
<222> LOCATION: (7)..(7)
<223> OTHER INFORMATION: Xaa is isosteric methionine analog norleucine
<220> FEATURE:
<221> NAME/KEY: misc_feature
<222> LOCATION: (82)..(82)
<223> OTHER INFORMATION: Xaa is isosteric methionine analog norleucine
<220> FEATURE:
<221> NAME/KEY: misc_feature
<222> LOCATION: (95)..(95)
<223> OTHER INFORMATION: Xaa is isosteric methionine analog norleucine
<220> FEATURE:
<221> NAME/KEY: misc_feature
<222> LOCATION: (163)..(163)
<223> OTHER INFORMATION: Xaa is isosteric methionine analog norleucine
<220> FEATURE:
<221> NAME/KEY: misc_feature
<222> LOCATION: (222)..(222)
<223> OTHER INFORMATION: Xaa is isosteric methionine analog norleucine
<220> FEATURE:
<221> NAME/KEY: misc_feature
<222> LOCATION: (257)..(257)
<223> OTHER INFORMATION: Xaa is isosteric methionine analog norleucine

<400> SEQUENCE: 12
```

His His His His His His Xaa Ile Val Leu Phe Val Asp Phe Asp Tyr
1               5                   10                  15

Phe Ser Ala Gln Val Glu Glu Val Leu Asn Pro Ser Leu Lys Gly Lys
            20                  25                  30

Pro Val Val Val Ser Val Phe Ser Gly Arg Phe Glu Asp Ser Gly Ala
        35                  40                  45

Val Ala Thr Ala Asn Tyr Glu Ala Arg Lys Phe Gly Val Lys Ala Gly
    50                  55                  60

Ile Pro Ile Val Glu Ala Lys Lys Ile Leu Pro Asn Ala Val Tyr Leu
65                  70                  75                  80

Pro Xaa Arg Lys Glu Val Tyr Gln Gln Val Ser Cys Arg Ile Xaa Asn
                85                  90                  95

Leu Leu Arg Glu Tyr Ser Glu Lys Ile Glu Ile Ala Ser Ile Asp Glu
            100                 105                 110

Ala Tyr Leu Asp Ile Ser Asp Lys Val Arg Asp Tyr Arg Glu Ala Tyr
        115                 120                 125

Ala Leu Gly Leu Glu Ile Lys Asn Lys Ile Leu Glu Lys Glu Lys Ile
    130                 135                 140

Thr Val Thr Val Gly Ile Ser Lys Asn Lys Val Phe Ala Lys Ile Ala
145                 150                 155                 160

Ala Asp Xaa Ala Lys Pro Asn Gly Ile Lys Val Ile Asp Glu Glu
                165                 170                 175

Val Lys Arg Leu Ile Arg Glu Leu Asp Ile Ala Asp Val Pro Gly Ile
        180                 185                 190

Gly Asn Ile Thr Ala Glu Lys Leu Lys Lys Leu Gly Ile Asn Lys Leu
    195                 200                 205

Val Asp Thr Leu Ala Ile Glu Phe Asp Lys Leu Lys Gly Xaa Ile Gly
210                 215                 220

Glu Ala Lys Ala Lys Tyr Leu Ile Ser Leu Ala Arg Asp Glu Tyr Asn
225                 230                 235                 240

Glu Pro Ile Arg Thr Arg Val Arg Lys Ser Ile Gly Arg Ile Val Thr
            245                 250                 255

Xaa Lys Arg Asn Ser Arg Asn Leu Glu Glu Ile Lys Pro Tyr Leu Phe

```
                260                 265                 270
Arg Ala Ile Glu Glu Ser Tyr Tyr Lys Leu Asp Lys Arg Ile Pro Lys
            275                 280                 285

Ala Ile His Val Val Ala Val Thr Glu Asp Leu Asp Ile Val Ser Arg
            290                 295                 300

Gly Arg Thr Phe Pro His Gly Ile Ser Lys Glu Thr Ala Tyr Ala Glu
305                 310                 315                 320

Ser Val Lys Leu Leu Gln Lys Ile Leu Glu Glu Asp Glu Arg Lys Ile
            325                 330                 335

Arg Arg Ile Gly Val Arg Phe Ser Lys Phe Ile Glu Ala Ile Gly Leu
            340                 345                 350

Asp Lys Phe Phe Asp Thr
            355
```

<210> SEQ ID NO 13
<211> LENGTH: 352
<212> TYPE: PRT
<213> ORGANISM: Artificial sequence
<220> FEATURE:
<223> OTHER INFORMATION: Dpo4-6m-Y12S without His tag
<220> FEATURE:
<221> NAME/KEY: misc_feature
<222> LOCATION: (1)..(1)
<223> OTHER INFORMATION: Xaa is isosteric methionine analog norleucine
<220> FEATURE:
<221> NAME/KEY: misc_feature
<222> LOCATION: (76)..(76)
<223> OTHER INFORMATION: Xaa is isosteric methionine analog norleucine
<220> FEATURE:
<221> NAME/KEY: misc_feature
<222> LOCATION: (89)..(89)
<223> OTHER INFORMATION: Xaa is isosteric methionine analog norleucine
<220> FEATURE:
<221> NAME/KEY: misc_feature
<222> LOCATION: (157)..(157)
<223> OTHER INFORMATION: Xaa is isosteric methionine analog norleucine
<220> FEATURE:
<221> NAME/KEY: misc_feature
<222> LOCATION: (216)..(216)
<223> OTHER INFORMATION: Xaa is isosteric methionine analog norleucine
<220> FEATURE:
<221> NAME/KEY: misc_feature
<222> LOCATION: (251)..(251)
<223> OTHER INFORMATION: Xaa is isosteric methionine analog norleucine

<400> SEQUENCE: 13

```
Xaa Ile Val Leu Phe Val Asp Phe Asp Tyr Phe Ser Ala Gln Val Glu
1               5                   10                  15

Glu Val Leu Asn Pro Ser Leu Lys Gly Lys Pro Val Val Val Ser Val
            20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
        50                  55                  60

Lys Lys Ile Leu Pro Asn Ala Val Tyr Leu Pro Xaa Arg Lys Glu Val
65                  70                  75                  80

Tyr Gln Gln Val Ser Cys Arg Ile Xaa Asn Leu Leu Arg Glu Tyr Ser
            85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Ala Leu Gly Leu Glu Ile
            115                 120                 125

Lys Asn Lys Ile Leu Glu Lys Glu Lys Ile Thr Val Thr Val Gly Ile
```

```
            130                 135                 140
Ser Lys Asn Lys Val Phe Ala Lys Ile Ala Ala Asp Xaa Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ala Ile
            195                 200                 205

Glu Phe Asp Lys Leu Lys Gly Xaa Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Xaa Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Val Thr Glu Asp Leu Asp Ile Val Ser Arg Gly Arg Thr Phe Pro His
290                 295                 300

Gly Ile Ser Lys Glu Thr Ala Tyr Ala Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 14
<211> LENGTH: 358
<212> TYPE: PRT
<213> ORGANISM: Artificial sequence
<220> FEATURE:
<223> OTHER INFORMATION: Dpo4-6m-Y12A with 5' His tag
<220> FEATURE:
<221> NAME/KEY: misc_feature
<222> LOCATION: (7)..(7)
<223> OTHER INFORMATION: Xaa is isosteric methionine analog norleucine
<220> FEATURE:
<221> NAME/KEY: misc_feature
<222> LOCATION: (82)..(82)
<223> OTHER INFORMATION: Xaa is isosteric methionine analog norleucine
<220> FEATURE:
<221> NAME/KEY: misc_feature
<222> LOCATION: (95)..(95)
<223> OTHER INFORMATION: Xaa is isosteric methionine analog norleucine
<220> FEATURE:
<221> NAME/KEY: misc_feature
<222> LOCATION: (163)..(163)
<223> OTHER INFORMATION: Xaa is isosteric methionine analog norleucine
<220> FEATURE:
<221> NAME/KEY: misc_feature
<222> LOCATION: (222)..(222)
<223> OTHER INFORMATION: Xaa is isosteric methionine analog norleucine
<220> FEATURE:
<221> NAME/KEY: misc_feature
<222> LOCATION: (257)..(257)
<223> OTHER INFORMATION: Xaa is isosteric methionine analog norleucine

<400> SEQUENCE: 14

His His His His His His Xaa Ile Val Leu Phe Val Asp Phe Asp Tyr
1               5                   10                  15

Phe Ala Ala Gln Val Glu Glu Val Leu Asn Pro Ser Leu Lys Gly Lys
```

```
                20                  25                  30
Pro Val Val Val Ser Val Phe Ser Gly Arg Phe Glu Asp Ser Gly Ala
                35                  40                  45
Val Ala Thr Ala Asn Tyr Glu Ala Arg Lys Phe Gly Val Lys Ala Gly
 50                  55                  60
Ile Pro Ile Val Glu Ala Lys Lys Ile Leu Pro Asn Ala Val Tyr Leu
 65                  70                  75                  80
Pro Xaa Arg Lys Glu Val Tyr Gln Gln Val Ser Cys Arg Ile Xaa Asn
                 85                  90                  95
Leu Leu Arg Glu Tyr Ser Glu Lys Ile Glu Ile Ala Ser Ile Asp Glu
                100                 105                 110
Ala Tyr Leu Asp Ile Ser Asp Lys Val Arg Asp Tyr Arg Glu Ala Tyr
                115                 120                 125
Ala Leu Gly Leu Glu Ile Lys Asn Lys Ile Leu Glu Lys Glu Lys Ile
                130                 135                 140
Thr Val Thr Val Gly Ile Ser Lys Asn Lys Val Phe Ala Lys Ile Ala
145                 150                 155                 160
Ala Asp Xaa Ala Lys Pro Asn Gly Ile Lys Val Ile Asp Asp Glu Glu
                165                 170                 175
Val Lys Arg Leu Ile Arg Glu Leu Asp Ile Ala Asp Val Pro Gly Ile
                180                 185                 190
Gly Asn Ile Thr Ala Glu Lys Leu Lys Lys Leu Gly Ile Asn Lys Leu
                195                 200                 205
Val Asp Thr Leu Ala Ile Glu Phe Asp Lys Leu Lys Gly Xaa Ile Gly
                210                 215                 220
Glu Ala Lys Ala Lys Tyr Leu Ile Ser Leu Ala Arg Asp Glu Tyr Asn
225                 230                 235                 240
Glu Pro Ile Arg Thr Arg Val Arg Lys Ser Ile Gly Arg Ile Val Thr
                245                 250                 255
Xaa Lys Arg Asn Ser Arg Asn Leu Glu Glu Ile Lys Pro Tyr Leu Phe
                260                 265                 270
Arg Ala Ile Glu Glu Ser Tyr Tyr Lys Leu Asp Lys Arg Ile Pro Lys
                275                 280                 285
Ala Ile His Val Val Ala Val Thr Glu Asp Leu Asp Ile Val Ser Arg
                290                 295                 300
Gly Arg Thr Phe Pro His Gly Ile Ser Lys Glu Thr Ala Tyr Ala Glu
305                 310                 315                 320
Ser Val Lys Leu Leu Gln Lys Ile Leu Glu Glu Asp Glu Arg Lys Ile
                325                 330                 335
Arg Arg Ile Gly Val Arg Phe Ser Lys Phe Ile Glu Ala Ile Gly Leu
                340                 345                 350
Asp Lys Phe Phe Asp Thr
                355

<210> SEQ ID NO 15
<211> LENGTH: 358
<212> TYPE: PRT
<213> ORGANISM: Artificial sequence
<220> FEATURE:
<223> OTHER INFORMATION: Dpo4-6m-Y12A without His tag
<220> FEATURE:
<221> NAME/KEY: misc_feature
<222> LOCATION: (7)..(7)
<223> OTHER INFORMATION: Xaa is isosteric methionine analog norleucine
<220> FEATURE:
<221> NAME/KEY: misc_feature
<222> LOCATION: (82)..(82)
```

```
<223> OTHER INFORMATION: Xaa is isosteric methionine analog norleucine
<220> FEATURE:
<221> NAME/KEY: misc_feature
<222> LOCATION: (95)..(95)
<223> OTHER INFORMATION: Xaa is isosteric methionine analog norleucine
<220> FEATURE:
<221> NAME/KEY: misc_feature
<222> LOCATION: (163)..(163)
<223> OTHER INFORMATION: Xaa is isosteric methionine analog norleucine
<220> FEATURE:
<221> NAME/KEY: misc_feature
<222> LOCATION: (222)..(222)
<223> OTHER INFORMATION: Xaa is isosteric methionine analog norleucine
<220> FEATURE:
<221> NAME/KEY: misc_feature
<222> LOCATION: (257)..(257)
<223> OTHER INFORMATION: Xaa is isosteric methionine analog norleucine

<400> SEQUENCE: 15

His His His His His His Xaa Ile Val Leu Phe Val Asp Phe Asp Tyr
1               5                   10                  15

Phe Ala Ala Gln Val Glu Glu Val Leu Asn Pro Ser Leu Lys Gly Lys
            20                  25                  30

Pro Val Val Val Ser Val Phe Ser Gly Arg Phe Glu Asp Ser Gly Ala
        35                  40                  45

Val Ala Thr Ala Asn Tyr Glu Ala Arg Lys Phe Gly Val Lys Ala Gly
    50                  55                  60

Ile Pro Ile Val Glu Ala Lys Lys Ile Leu Pro Asn Ala Val Tyr Leu
65                  70                  75                  80

Pro Xaa Arg Lys Glu Val Tyr Gln Gln Val Ser Cys Arg Ile Xaa Asn
                85                  90                  95

Leu Leu Arg Glu Tyr Ser Glu Lys Ile Glu Ile Ala Ser Ile Asp Glu
            100                 105                 110

Ala Tyr Leu Asp Ile Ser Asp Lys Val Arg Asp Tyr Arg Glu Ala Tyr
        115                 120                 125

Ala Leu Gly Leu Glu Ile Lys Asn Lys Ile Leu Glu Lys Glu Lys Ile
    130                 135                 140

Thr Val Thr Val Gly Ile Ser Lys Asn Lys Val Phe Ala Lys Ile Ala
145                 150                 155                 160

Ala Asp Xaa Ala Lys Pro Asn Gly Ile Lys Val Ile Asp Asp Glu Glu
                165                 170                 175

Val Lys Arg Leu Ile Arg Glu Leu Asp Ile Ala Asp Val Pro Gly Ile
            180                 185                 190

Gly Asn Ile Thr Ala Glu Lys Leu Lys Lys Leu Gly Ile Asn Lys Leu
        195                 200                 205

Val Asp Thr Leu Ala Ile Glu Phe Asp Lys Leu Lys Gly Xaa Ile Gly
    210                 215                 220

Glu Ala Lys Ala Lys Tyr Leu Ile Ser Leu Ala Arg Asp Glu Tyr Asn
225                 230                 235                 240

Glu Pro Ile Arg Thr Arg Val Arg Lys Ser Ile Gly Arg Ile Val Thr
                245                 250                 255

Xaa Lys Arg Asn Ser Arg Asn Leu Glu Glu Ile Lys Pro Tyr Leu Phe
            260                 265                 270

Arg Ala Ile Glu Glu Ser Tyr Tyr Lys Leu Asp Lys Arg Ile Pro Lys
        275                 280                 285

Ala Ile His Val Val Ala Val Thr Glu Asp Leu Asp Ile Val Ser Arg
    290                 295                 300

Gly Arg Thr Phe Pro His Gly Ile Ser Lys Glu Thr Ala Tyr Ala Glu
305                 310                 315                 320
```

```
Ser Val Lys Leu Leu Gln Lys Ile Leu Glu Glu Asp Glu Arg Lys Ile
            325                 330                 335

Arg Arg Ile Gly Val Arg Phe Ser Lys Phe Ile Glu Ala Ile Gly Leu
            340                 345                 350

Asp Lys Phe Phe Asp Thr
            355
```

<210> SEQ ID NO 16
<211> LENGTH: 358
<212> TYPE: PRT
<213> ORGANISM: Artificial sequence
<220> FEATURE:
<223> OTHER INFORMATION: Dpo4-6m-Y12G with 5' His tag
<220> FEATURE:
<221> NAME/KEY: misc_feature
<222> LOCATION: (7)..(7)
<223> OTHER INFORMATION: Xaa is isosteric methionine analog norleucine
<220> FEATURE:
<221> NAME/KEY: misc_feature
<222> LOCATION: (82)..(82)
<223> OTHER INFORMATION: Xaa is isosteric methionine analog norleucine
<220> FEATURE:
<221> NAME/KEY: misc_feature
<222> LOCATION: (95)..(95)
<223> OTHER INFORMATION: Xaa is isosteric methionine analog norleucine
<220> FEATURE:
<221> NAME/KEY: misc_feature
<222> LOCATION: (163)..(163)
<223> OTHER INFORMATION: Xaa is isosteric methionine analog norleucine
<220> FEATURE:
<221> NAME/KEY: misc_feature
<222> LOCATION: (222)..(222)
<223> OTHER INFORMATION: Xaa is isosteric methionine analog norleucine
<220> FEATURE:
<221> NAME/KEY: misc_feature
<222> LOCATION: (257)..(257)
<223> OTHER INFORMATION: Xaa is isosteric methionine analog norleucine

<400> SEQUENCE: 16

```
His His His His His His Xaa Ile Val Leu Phe Val Asp Phe Asp Tyr
1               5                   10                  15

Phe Gly Ala Gln Val Glu Glu Val Leu Asn Pro Ser Leu Lys Gly Lys
            20                  25                  30

Pro Val Val Val Ser Val Phe Ser Gly Arg Phe Glu Asp Ser Gly Ala
        35                  40                  45

Val Ala Thr Ala Asn Tyr Glu Ala Arg Lys Phe Gly Val Lys Ala Gly
    50                  55                  60

Ile Pro Ile Val Glu Ala Lys Lys Ile Leu Pro Asn Ala Val Tyr Leu
65                  70                  75                  80

Pro Xaa Arg Lys Glu Val Tyr Gln Gln Val Ser Cys Arg Ile Xaa Asn
                85                  90                  95

Leu Leu Arg Glu Tyr Ser Glu Lys Ile Glu Ile Ala Ser Ile Asp Glu
            100                 105                 110

Ala Tyr Leu Asp Ile Ser Asp Lys Val Arg Asp Tyr Arg Glu Ala Tyr
        115                 120                 125

Ala Leu Gly Leu Glu Ile Lys Asn Lys Ile Leu Glu Lys Glu Lys Ile
    130                 135                 140

Thr Val Thr Val Gly Ile Ser Lys Asn Lys Val Phe Ala Lys Ile Ala
145                 150                 155                 160

Ala Asp Xaa Ala Lys Pro Asn Gly Ile Lys Val Ile Asp Asp Glu Glu
                165                 170                 175

Val Lys Arg Leu Ile Arg Glu Leu Asp Ile Ala Asp Val Pro Gly Ile
            180                 185                 190
```

```
Gly Asn Ile Thr Ala Glu Lys Leu Lys Lys Leu Gly Ile Asn Lys Leu
            195                 200                 205

Val Asp Thr Leu Ala Ile Glu Phe Asp Lys Leu Lys Gly Xaa Ile Gly
    210                 215                 220

Glu Ala Lys Ala Lys Tyr Leu Ile Ser Leu Ala Arg Asp Glu Tyr Asn
225                 230                 235                 240

Glu Pro Ile Arg Thr Arg Val Arg Lys Ser Ile Gly Arg Ile Val Thr
                245                 250                 255

Xaa Lys Arg Asn Ser Arg Asn Leu Glu Glu Ile Lys Pro Tyr Leu Phe
                260                 265                 270

Arg Ala Ile Glu Glu Ser Tyr Tyr Lys Leu Asp Lys Arg Ile Pro Lys
            275                 280                 285

Ala Ile His Val Val Ala Val Thr Glu Asp Leu Asp Ile Val Ser Arg
            290                 295                 300

Gly Arg Thr Phe Pro His Gly Ile Ser Lys Glu Thr Ala Tyr Ala Glu
305                 310                 315                 320

Ser Val Lys Leu Leu Gln Lys Ile Leu Glu Glu Asp Glu Arg Lys Ile
                325                 330                 335

Arg Arg Ile Gly Val Arg Phe Ser Lys Phe Ile Glu Ala Ile Gly Leu
            340                 345                 350

Asp Lys Phe Phe Asp Thr
        355

<210> SEQ ID NO 17
<211> LENGTH: 352
<212> TYPE: PRT
<213> ORGANISM: Artificial sequence
<220> FEATURE:
<223> OTHER INFORMATION: Dpo4-6m-Y12G without His tag
<220> FEATURE:
<221> NAME/KEY: misc_feature
<222> LOCATION: (1)..(1)
<223> OTHER INFORMATION: Xaa is isosteric methionine analog norleucine
<220> FEATURE:
<221> NAME/KEY: misc_feature
<222> LOCATION: (76)..(76)
<223> OTHER INFORMATION: Xaa is isosteric methionine analog norleucine
<220> FEATURE:
<221> NAME/KEY: misc_feature
<222> LOCATION: (89)..(89)
<223> OTHER INFORMATION: Xaa is isosteric methionine analog norleucine
<220> FEATURE:
<221> NAME/KEY: misc_feature
<222> LOCATION: (157)..(157)
<223> OTHER INFORMATION: Xaa is isosteric methionine analog norleucine
<220> FEATURE:
<221> NAME/KEY: misc_feature
<222> LOCATION: (216)..(216)
<223> OTHER INFORMATION: Xaa is isosteric methionine analog norleucine
<220> FEATURE:
<221> NAME/KEY: misc_feature
<222> LOCATION: (251)..(251)
<223> OTHER INFORMATION: Xaa is isosteric methionine analog norleucine

<400> SEQUENCE: 17

Xaa Ile Val Leu Phe Val Asp Phe Asp Tyr Phe Gly Ala Gln Val Glu
1               5                   10                  15

Glu Val Leu Asn Pro Ser Leu Lys Gly Lys Pro Val Val Val Ser Val
                20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
    50                  55                  60
```

```
Lys Lys Ile Leu Pro Asn Ala Val Tyr Leu Pro Xaa Arg Lys Glu Val
 65                  70                  75                  80

Tyr Gln Gln Val Ser Cys Arg Ile Xaa Asn Leu Leu Arg Glu Tyr Ser
             85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Ala Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Lys Ile Ala Ala Asp Xaa Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
                180                 185                 190

Lys Leu Lys Lys Leu Gly Ile Asn Lys Leu Val Asp Thr Leu Ala Ile
            195                 200                 205

Glu Phe Asp Lys Leu Lys Gly Xaa Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Xaa Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Val Thr Glu Asp Leu Asp Ile Val Ser Arg Gly Arg Thr Phe Pro His
290                 295                 300

Gly Ile Ser Lys Glu Thr Ala Tyr Ala Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 18
<211> LENGTH: 41
<212> TYPE: DNA
<213> ORGANISM: Artificial sequence
<220> FEATURE:
<223> OTHER INFORMATION: (D)-41-nt DNA template

<400> SEQUENCE: 18
ggacggcatt ggatcgacga tgagttggtt ggacggctgc g                    41

<210> SEQ ID NO 19
<211> LENGTH: 41
<212> TYPE: RNA
<213> ORGANISM: Artificial sequence
<220> FEATURE:
<223> OTHER INFORMATION: (D)-41-nt RNA template

<400> SEQUENCE: 19
ggacggcauu ggaucgacga ugaguugguu ggacggcugc g                    41
```

<210> SEQ ID NO 20
<211> LENGTH: 21
<212> TYPE: DNA
<213> ORGANISM: Artificial sequence
<220> FEATURE:
<223> OTHER INFORMATION: (D)- 21 nt DNA primer (DNA-1-P)  5' FAM
      labelled
<220> FEATURE:
<221> NAME/KEY: misc_feature
<222> LOCATION: (1)..(1)
<223> OTHER INFORMATION: 5' FAM conjugated

<400> SEQUENCE: 20
cgcagccgtc caaccaactc a                                              21

<210> SEQ ID NO 21
<211> LENGTH: 21
<212> TYPE: RNA
<213> ORGANISM: Artificial sequence
<220> FEATURE:
<223> OTHER INFORMATION: (D)- 21 nt RNA primer (RNA-1-P)  5' FAM
      labelled
<220> FEATURE:
<221> NAME/KEY: misc_feature
<222> LOCATION: (1)..(1)
<223> OTHER INFORMATION: 5' FAM conjugated

<400> SEQUENCE: 21
cgcagccguc caaccaacuc a                                              21

<210> SEQ ID NO 22
<211> LENGTH: 15
<212> TYPE: DNA
<213> ORGANISM: Artificial sequence
<220> FEATURE:
<223> OTHER INFORMATION: (L)-15-nt DNA primer  5' FAM labelled
<220> FEATURE:
<221> NAME/KEY: misc_feature
<222> LOCATION: (1)..(1)
<223> OTHER INFORMATION: 5' FAM conjugated

<400> SEQUENCE: 22
acctaacgcc atgta                                                     15

<210> SEQ ID NO 23
<211> LENGTH: 25
<212> TYPE: DNA
<213> ORGANISM: Artificial Sequence
<220> FEATURE:
<223> OTHER INFORMATION: (L)-FAM-PCR-R-DNA primer 5' FAM labelled

<400> SEQUENCE: 23
atgcctggca gttccctact ctcgc                                          25

<210> SEQ ID NO 24
<211> LENGTH: 19
<212> TYPE: DNA
<213> ORGANISM: Artificial Sequence
<220> FEATURE:
<223> OTHER INFORMATION: (L)-PCR-F-DNA primer 5' FAM labelled

<400> SEQUENCE: 24
tgcctggcgg cagtagcgc                                                 19

<210> SEQ ID NO 25
<211> LENGTH: 120
<212> TYPE: DNA
<213> ORGANISM: Artificial Sequence
<220> FEATURE:
<223> OTHER INFORMATION: (L)-120-nt DNA template

<400> SEQUENCE: 25
atgcctggca gttccctact ctcgcatggg gagaccccac actaccatcg gcgctacggc    60
gtttcacttc tgagttcggc atggggtcag gtgggaccac cgcgctactg ccgccaggca    120

<210> SEQ ID NO 26
<211> LENGTH: 120
<212> TYPE: DNA
<213> ORGANISM: Artificial Sequence
<220> FEATURE:
<223> OTHER INFORMATION: (L)-120-nt 5S RNA template (a transcription
      product of SEQ ID NO: 25
<220> FEATURE:
<221> NAME/KEY: misc_feature
<222> LOCATION: (1)..(1)
<223> OTHER INFORMATION: 5'-FAM

<400> SEQUENCE: 26
ugccuggcgg caguagcgcg gugucccac cugaccccau gccgaacuca gaagugaaac    60
gccguagcgc cgaugguagu gugggguucuc cccaugcgag aguagggaac ugccaggcau   120

<210> SEQ ID NO 27
<211> LENGTH: 25
<212> TYPE: DNA
<213> ORGANISM: Artificial Sequence
<220> FEATURE:
<223> OTHER INFORMATION: (L) 25 nt DNA Primer (for RT of L-5S rRNA)
<220> FEATURE:
<221> NAME/KEY: misc_feature
<222> LOCATION: (1)..(1)
<223> OTHER INFORMATION: 5'-Cy5

<400> SEQUENCE: 27
atgcctggca gttccctact ctcgc                                          25

<210> SEQ ID NO 28
<211> LENGTH: 120
<212> TYPE: DNA
<213> ORGANISM: Artificial Sequence
<220> FEATURE:
<223> OTHER INFORMATION: (D)-120-nt DNA (marker)
<220> FEATURE:
<221> NAME/KEY: misc_feature
<222> LOCATION: (1)..(1)
<223> OTHER INFORMATION: 5'-Cy5

<400> SEQUENCE: 28
atgcctggca gttccctact ctcgcatggg gagaccccac actaccatcg gcgctacggc    60
gtttcacttc tgagttcggc atggggtcag gtgggaccac cgcgctactg ccgccaggca    120

<210> SEQ ID NO 29
<211> LENGTH: 19
<212> TYPE: DNA
<213> ORGANISM: Artificial Sequence
<220> FEATURE:
<223> OTHER INFORMATION: (L) 5S rRNA-PCR-F primer

<400> SEQUENCE: 29
tgcctggcgg cagtagcgc                                                 19

<210> SEQ ID NO 30
<211> LENGTH: 25
<212> TYPE: DNA
<213> ORGANISM: Artificial Sequence -continued
<220> FEATURE:
<223> OTHER INFORMATION: (L) 5S rRNA-PCR-R primer

<400> SEQUENCE: 30
atgcctggca gttccctact ctcgc                                       25

<210> SEQ ID NO 31
<211> LENGTH: 76
<212> TYPE: DNA
<213> ORGANISM: Artificial Sequence
<220> FEATURE:
<223> OTHER INFORMATION: (L) 76 nt tRNA template

<400> SEQUENCE: 31
gggucguuag cucaguuggu agagcaguug acuuuuaauc aauuggucgc agguucgaau    60
ccugcacgac ccacca                                                   76

<210> SEQ ID NO 32
<211> LENGTH: 14
<212> TYPE: DNA
<213> ORGANISM: Artificial Sequence
<220> FEATURE:
<223> OTHER INFORMATION: (L)-FAM-14 nt DNA primer (for RT of L-76 nt
      tRNA)
<220> FEATURE:
<221> NAME/KEY: misc_feature
<222> LOCATION: (1)..(1)
<223> OTHER INFORMATION: 5'-FAM

<400> SEQUENCE: 32
tggtgggtcg tgca                                                    14

<210> SEQ ID NO 33
<211> LENGTH: 18
<212> TYPE: DNA
<213> ORGANISM: Artificial Sequence
<220> FEATURE:
<223> OTHER INFORMATION: (L) 18 nt PCR-F primer (for amplifying 76 nt RT
      DNA)

<400> SEQUENCE: 33
gggtcgttag ctcagttg                                                18

<210> SEQ ID NO 34
<211> LENGTH: 14
<212> TYPE: DNA
<213> ORGANISM: Artificial Sequence
<220> FEATURE:
<223> OTHER INFORMATION: (L) 14 nt PCR-R primer (for amplifying 76 nt RT
      DNA)

<400> SEQUENCE: 34
tggtgggtcg tgca                                                    14

<210> SEQ ID NO 35
<211> LENGTH: 18
<212> TYPE: DNA
<213> ORGANISM: Artificial Sequence
<220> FEATURE:
<223> OTHER INFORMATION: (L) 18 nt PCR-F primer (for amplifying 76 nt RT
      DNA)
<220> FEATURE:
<221> NAME/KEY: misc_feature
<222> LOCATION: (1)..(1)
<223> OTHER INFORMATION: 5'-FAM

<400> SEQUENCE: 35

```
gggtcgttag ctcagttg                                              18
```

<210> SEQ ID NO 36
<211> LENGTH: 76
<212> TYPE: DNA
<213> ORGANISM: Artificial Sequence
<220> FEATURE:
<223> OTHER INFORMATION: (L)- 76 nt DNA (a reverse transcription product
      of SEQ ID NO: 31)

<400> SEQUENCE: 36

```
tggtgggtcg tgcaggattc gaacctgcga ccaattgatt aaaagtcaac tgctctacca    60
actgagctaa cgaccc                                                   76
```

METHODS OF SEQUENCING AND PRODUCING NUCLEIC ACID SEQUENCES

RELATED APPLICATIONS

This application is a US Continuation of PCT Patent Application No. PCT/IB2019/052752 having international filing date of Apr. 4, 2019 which claims the benefit of priority under 35 USC § 119(e) of U.S. Provisional Patent Application No. 62/652,915 filed on Apr. 5, 2018. The contents of the above applications are all incorporated by reference as if fully set forth herein in their entirety.

SEQUENCE LISTING STATEMENT

The ASCII file, entitled 83542SequenceListing.txt, created on Sep. 28, 2020, comprising 49,960 bytes, submitted concurrently with the filing of this application is incorporated herein by reference.

FIELD AND BACKGROUND OF THE INVENTION

The present invention, in some embodiments thereof, relates to methods of sequencing and producing nucleic acid sequences.

Nucleic acids are used in various technologies, as catalysts, inhibitors or stimulators of biochemical reactions that take place in or outside the cell. In their natural form nucleic acids comprise D-ribose or D-deoxyribose as the sugar backbone for RNA or DNA respectively. Naturally occurring nucleic acids are subjected to the activity of degrading enzymes which significantly shortens the effect of these molecules in the natural environment. Hence, mirror-image biological systems hold promise for many applications which take place in a biological environment that comprises these enzymes such as in medicine, pharmaceutical diagnostics, biotechnology and agriculture. For example, nuclease-resistant L-DNA aptamers are categorized as plasma-stable L-aptamer drugs[1,2].

However, the production, development and use of such mirror-image nucleic acid molecules require a sensitive, accurate and reproducible method to verify the mass, length and sequence of the L-nucleic acid sequences.

Despite the remarkable advancements in DNA sequencing technologies, no practical method for sequencing L-DNA has been reported. Most of the commonly used sequencing-by-synthesis methods are unavailable because they require a polymerase capable of incorporating labeled L-di-deoxynucleotide triphosphates (L-ddNTPs) or L-deoxyribonucleotide triphosphates (dNTPs). Although a couple of mirror-image polymerase systems based on enzymes small enough for total chemical synthesis, such as the African Swine Fever Virus polymerase X (ASFV pol X)[5] and the *Sulfolobus solfataricus* P2 DNA polymerase IV (Dpo4)[3,4,6], have been developed, they still suffer from poor fidelity and inability to incorporate labeled ddNTPs or dNTPs. Next-generation nanopore DNA sequencing approach could be applied for sequencing mirror-image DNA in principle, however it also requires a particular D-nucleic acid polymerase or helicase, which is not yet available, to help slow down DNA movement through the pore[7].

Additional background art includes U.S. Pat. No. 6,605,713; Canadian Patent No. CA2045891 and International Patent Application Publication No: WO2010049156.

SUMMARY OF THE INVENTION

According to an aspect of some embodiments of the present invention there is provided a method of sequencing a nucleic acid sequence comprising L-nucleotides, the method comprising subjecting the nucleic acid sequence comprising the L-nucleotides to a chemical sequencing method using a chemical selected from the group consisting of Dimethyl sulfate, Methylamine, Diethyl pyrocarbonate, Methylene blue, Potassium chloropalladate, Sodium hydroxide, Osmium tetroxide, Spermine, potassium permanganate, Hydrazine, hydrazine hydrate, Hydroxylamine hydrochloride, Diethyl pyrocarbonate, Formic acid and Citrate buffer.

According to an aspect of some embodiments of the present invention there is provided a method of sequencing a nucleic acid sequence comprising L-nucleotides, the method comprising subjecting the nucleic acid sequence comprising the L-nucleotides to a chemical sequencing method, wherein the nucleic acid sequence comprises more than 120 nucleotides in length.

According to an aspect of some embodiments of the present invention there is provided a method of sequencing a nucleic acid sequence comprising L-nucleotides, the method comprising subjecting the nucleic acid sequence comprising the L-nucleotides to a chemical sequencing method, wherein the chemical sequencing method comprises gel-electrophoresis to determine the nucleic acid sequence.

According to an aspect of some embodiments of the present invention there is provided a method of sequencing a nucleic acid sequence comprising L-nucleotides, the method comprising:

(a) labeling at a 5' terminus or 3' terminus of the nucleic acid sequence comprising the L-nucleotides with 5-iodoacetamidofluorescein, so as to obtain a labeled nucleic acid sequence comprising the L-nucleotides; and (b) subjecting the labeled nucleic acid sequence comprising the L-nucleotides to a chemical sequencing method.

According to an aspect of some embodiments of the present invention there is provided a method of labeling a nucleic acid sequence comprising L-nucleotides, the method comprising labeling the nucleic acid sequence comprising the L-nucleotides at a 5' terminus using a polynucleotidekinase.

According to some embodiments of the invention, there is provided a method of sequencing a nucleic acid sequence comprising L-nucleotides, the method comprising:

(a) labeling the nucleic acid sequence comprising the L-nucleotides using a polynucleotide kinase according to the method of the present invention, so as to obtain a labeled nucleic acid sequence comprising the L-nucleotides; and (b) subjecting the labeled nucleic acid sequence comprising the L-nucleotides to a chemical sequencing method.

According to some embodiments of the invention, the chemical sequencing method comprises using a chemical selected from the group consisting of Dimethyl sulfate, Methylamine, Diethyl pyrocarbonate, Methylene blue, Potassium chloropalladate, Sodium hydroxide, Osmium tetroxide, Spermine, potassium permanganate, Hydrazine, hydrazine hydrate, Hydroxylamine hydrochloride, Diethyl pyrocarbonate, Formic acid and Citrate buffer.

According to some embodiments of the invention, the chemical is selected from the group consisting of Methylene blue, Sodium hydroxide, Hydroxylamine hydrochloride, Formic acid and hydrazine hydrate.

According to some embodiments of the invention, the nucleic acid sequence comprises more than 120 nucleotides in length.

According to some embodiments of the invention, the nucleic acid sequence comprises more than 150 nucleotides in length.

According to some embodiments of the invention, the method comprises labeling the nucleic acid sequence at a 5' terminus or 3' terminus with fluorescein amidite (FAM), 5-iodoacetamidofluorescein or biotin.

According to some embodiments of the invention, the method comprises labeling the nucleic acid sequence at a 5' terminus or 3' terminus with fluorescein amidite (FAM) or 5-iodoacetamidofluorescein.

According to some embodiments of the invention, the labeling is at a 5' terminus.

According to some embodiments of the invention, the method comprises labeling the nucleic acid sequence at a 5' terminus using a polynucleotide kinase.

According to some embodiments of the invention, the labeling comprises labeling with a radioactive isotype.

According to some embodiments of the invention, the method does not comprise mass-spectrometry (MS).

According to some embodiments of the invention, the nucleic acid sequence comprises deoxyribose nucleotides.

According to some embodiments of the invention, the nucleic acid sequence comprises ribose nucleotides.

According to some embodiments of the invention, the chemical sequencing method comprises:
  (a) labeling a plurality of molecules of the nucleic acid sequence at a 5' terminus or 3' terminus of the plurality of molecules with a label;
  (b) partially modifying the plurality of molecules following the (a) using a nucleobase-specific chemical agent such that upon cleaving the plurality of molecules adjacent to modified nucleobases a plurality of fragments of the nucleic acid sequence comprising the label are obtained;
  (c) cleaving the plurality of molecules following the (b) adjacent to modified nucleobases; and
  (d) determining the modified nucleobases positions in the nucleic acid sequence according to lengths, masses and/or charges of fragments produced by the cleaving and comprising the label.

According to some embodiments of the invention, the (b) is effected in at least 3 separate reaction mixtures so as to create a set of fragments comprising the label differing by a single nucleotide in length.

According to an aspect of some embodiments of the present invention there is provided a kit comprising chemicals for chemical sequencing of a nucleic acid sequence comprising L-nucleotides and a positive control template comprising a nucleic acid sequence comprising L-nucleotides.

According to some embodiments of the invention, the kit of the present invention comprising a label for labeling the nucleic acid sequence comprising the L-nucleotides at a 5' terminus or a 3' terminus of the nucleic acid sequence.

According to some embodiments of the invention, the kit of the present invention comprising a polynucleotide kinase.

According to an aspect of some embodiments of the present invention there is provided a method of reverse transcribing a ribose nucleic acid sequence into a deoxyribose nucleic acid sequence, the method comprising catalyzing reverse transcription of the ribose nucleic acid sequence with a *Sulfolobus solfataricus* P2 DNA polymerase IV (Dpo4).

According to some embodiments of the invention, the reverse transcription is effected in the presence of dNTPs.

According to some embodiments of the invention, the reverse transcription is effected in the presence of a primer that hybridizes to a 3' terminus of the ribose nucleic acid sequence.

According to some embodiments of the invention, the catalyzing is effected under conditions allowing reverse transcription of the ribose nucleic acid sequence.

According to an aspect of some embodiments of the present invention there is provided a kit comprising a *Sulfolobus solfataricus* P2 DNA polymerase IV (Dpo4) and a positive control template sequence comprising a ribose nucleic acid sequence.

According to some embodiments of the invention, the kit of the present invention comprising dNTPs.

According to some embodiments of the invention, the kit of the present invention comprising a primer that hybridizes to a 3' terminus of the positive control template sequence comprising the ribose nucleic acid sequence.

According to some embodiments of the invention, the ribose nucleic acid sequence is a D-ribose nucleic acid sequence and the Dpo4 is an L-Dpo4.

According to some embodiments of the invention, the ribose nucleic acid sequence is an L-ribose nucleic acid sequence and the Dpo4 is a D-Dpo4.

According to some embodiments of the invention, there is provided a method of amplifying a ribose nucleic acid sequence, the method comprising reverse transcribing the ribose nucleic acid sequence into a deoxyribose nucleic acid sequence according to the method of the present invention and amplifying the deoxyribose nucleic acid sequence.

According to some embodiments of the invention, there is provided a method of sequencing a ribose nucleic acid sequence, the method comprising reverse transcribing the ribose nucleic acid sequence into a deoxyribose nucleic acid sequence according to the method of the present invention and sequencing the deoxyribose nucleic acid sequence.

According to some embodiments of the invention, sequencing the deoxyribose nucleic acid sequence is effected by a chemical sequencing method.

According to some embodiments of the invention, sequencing is effected according to the method of the present invention.

According to some embodiments of the invention, there is provided a method of sequencing a nucleic acid sequence comprising L-ribose nucleotides, the method comprising reverse transcribing the nucleic acid sequence comprising the L-ribose nucleotides into a nucleic acid sequence comprising L-deoxyribose nucleotides according to the method of the present invention, wherein the Dpo4 is a D-Dpo4, and subjecting the nucleic acid sequence comprising the L-deoxyribose nucleotides to a chemical sequencing method.

According to some embodiments of the invention, there is provided a method of cloning an expression product of interest, the method comprising reverse transcribing a ribose nucleic acid sequence encoding the expression product of interest into a deoxyribose nucleic acid sequence according to the method of the present invention and cloning the deoxyribose nucleic acid in a host-cell.

According to some embodiments of the invention, there is provided a method of determining a transcriptome of a cell, the method comprising reverse transcribing ribose nucleic acid sequences expressed in the cell into deoxyribose nucleic acid sequences according to the method of the present invention.

According to some embodiments of the invention, the method comprises amplifying the deoxyribose nucleic acid sequence following the reverse transcribing.

According to some embodiments of the invention, the amplifying is effected by the Dpo4.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1B:
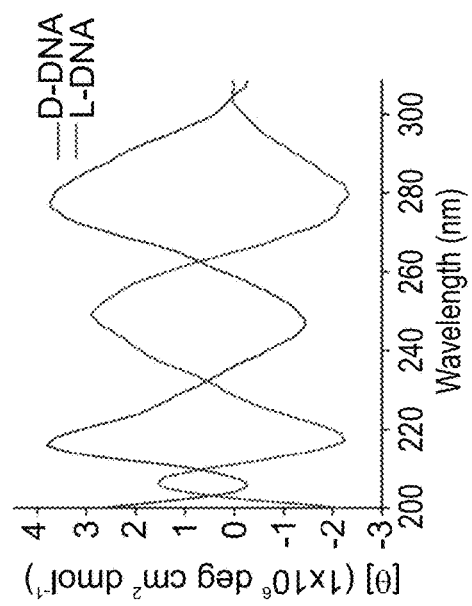
Figure 1C:
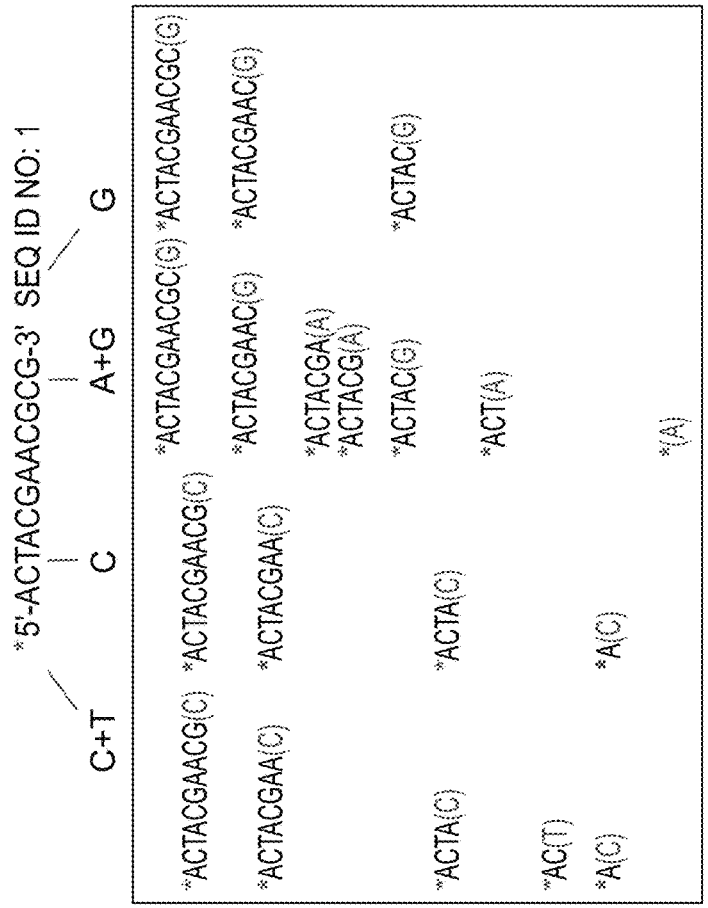
Figure 1D:
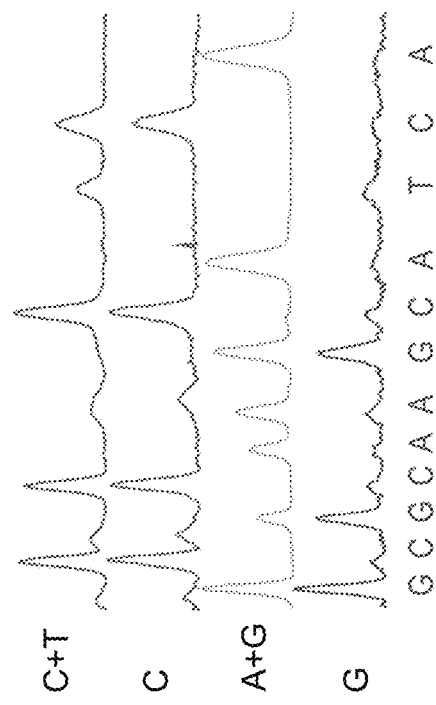

In the drawings:

FIGS. 1A-1D demonstrate chemical sequencing of a 5'-fluorescein amidite (FAM) labeled 12-nucleotides (nt) L-DNA oligonucleotide (oligo) (SEQ ID NO: 1). FIG. 1A shows the sequence and predicted chemical degradation pattern of the 12-nt L-DNA oligo, with cleaved nucleobases highlighted in parentheses, and fragments separated by PAGE corresponding to the positions of those shown in FIG. 1B. Asterisk denotes the 5'-FAM label. C+T reaction was performed by treatment with 50% hydrazine at 45° C. for 18 minutes; C-specific reaction with 4 M $NH_2OH$—HCl (pH 6.0) at RT for 20 minutes; A+G reaction with 80% formic acid at RT for 40 minutes; and G-specific reaction with 0.1% (m/v) methylene blue under UV for 2 minutes. The products were analyzed by 20% PAGE in 8 M urea scanned under FAM mode. FIG. 1B is a FAM mode photograph showing denaturing PAGE analysis of the 12-nt L-DNA oligo following chemical degradation. FIG. 1C is a sequencing chromatogram of the 12-nt L-DNA oligo. FIG. 1D is a graph demonstrating CD spectra of 12-nt D-DNA and L-DNA oligos of the same sequence (SEQ ID NO: 1).

FIG. 2 is a graph demonstrating absorption spectra of FAM and methylene blue. The absorption data was measured by a UV-VIS spectrophotometer.

FIGS. 3A-3C demonstrate chemical sequencing of a 5'-FAM labeled 12-nt D-DNA oligo (SEQ ID NO: 1). FIG. 3A shows the sequence and predicted chemical degradation pattern of the 12-nt D-DNA oligo, with cleaved nucleobases highlighted in parentheses, and fragments separated by PAGE corresponding to the positions of those shown in FIG. 3B. Asterisk denotes the 5'-FAM label. C+T reaction was performed by treatment with 50% hydrazine at 45° C. for 18 minutes; C-specific reaction with 4 M $NH_2OH$—HCl (pH 6.0) at RT for 20 minutes; A+G reaction with 80% formic acid at RT for 40 minutes; G-specific reaction with methylene blue under UV at RT for 2 minutes. The products were analyzed by 20% PAGE in 8 M urea scanned under FAM mode. FIG. 3B is a FAM mode photograph showing denaturing PAGE analysis of the 12-nt D-DNA oligo following chemical degradation. FIG. 3C is a sequencing chromatogram of the 12-nt D-DNA oligo.

FIGS. 4A-4D demonstrate chemical sequencing of a 5'-FAM labeled 11-nt L-DNA oligo (SEQ ID NO: 2). FIG. 4A shows the sequence and predicted chemical degradation pattern of the 11-nt L-DNA oligo, with cleaved nucleobases highlighted in parentheses, and fragments separated by PAGE corresponding to the positions of those shown in FIG. 4B. Asterisk denotes the 5'-FAM label. C+T reaction was performed by treatment with 50% hydrazine at 45° C. for 18 minutes; C-specific reaction with 4 M $NH_2OH$—HCl (pH 6.0) at RT for 20 minutes; A+G reaction with 80% formic acid at RT for 40 minutes; G-specific reaction with 0.1% (m/v) methylene blue under UV at RT for 2 minutes. The products were analyzed by 20% PAGE in 8 M urea under FAM mode. FIG. 4B is a FAM mode photograph showing denaturing PAGE analysis of the 11-nt L-DNA oligo following chemical degradation. FIG. 4C is a sequencing chromatogram of the 11-nt L-DNA oligo. FIG. 4D is a graph demonstrating CD spectra of 11-nt D-DNA and L-DNA oligos of the same sequence (SEQ ID NO: 2).

Figure 5A:
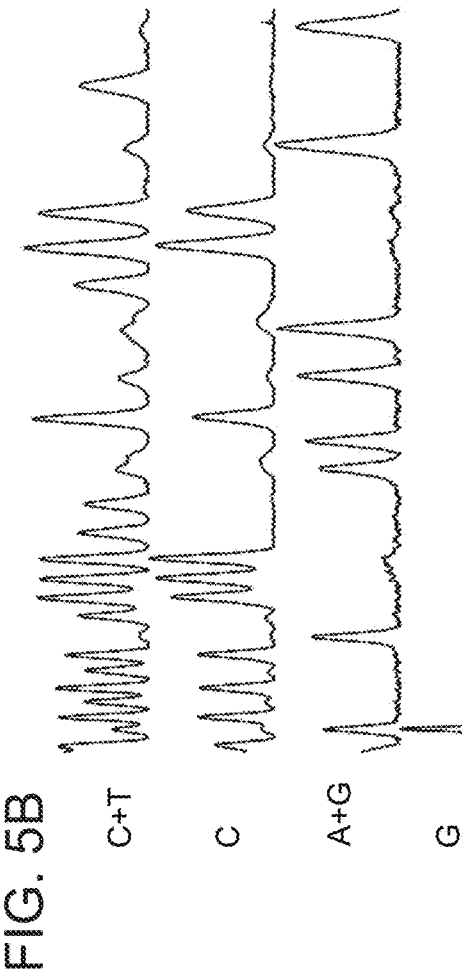
Figure 5B:
Figure 5C:
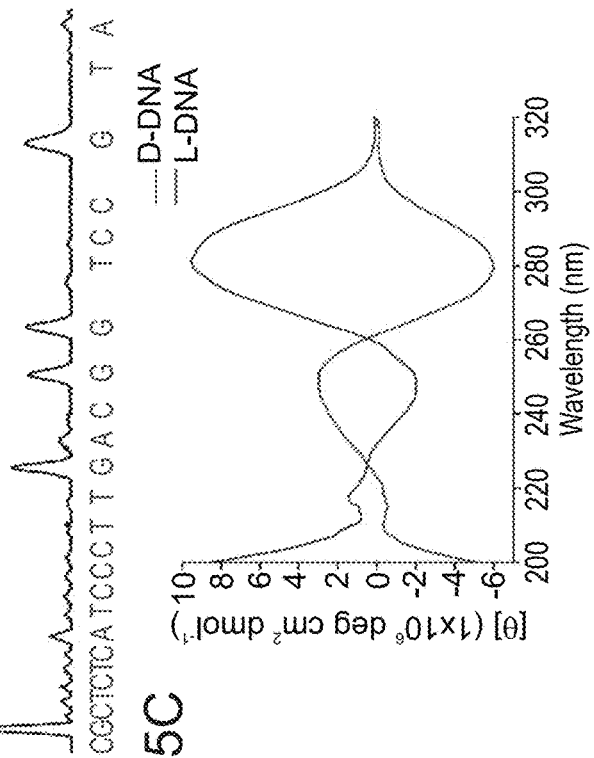

FIGS. 5A-5C demonstrate chemical sequencing of a 5'-FAM labeled 25-nucleotides (nt) L-DNA oligonucleotide (oligo) (SEQ ID NO: 3). FIG. 5A is a FAM mode photograph showing denaturing PAGE analysis of the 25-nt L-DNA oligo following chemical degradation. C+T reaction was performed by treatment with 50% hydrazine at 45° C. for 10 minutes; C-specific reaction with 4 M $NH_2OH$—HCl (pH 6.0) at RT for 10 minutes; A+G reaction with 66% formic acid at RT for 10 minutes; G-specific reaction with 0.1% (m/v) methylene blue under UV at RT for 4 minutes. The products were analyzed by 20% PAGE in 8 M urea scanned under FAM mode. FIG. 5B is a sequencing chromatogram of the 25-nt L-DNA oligo. FIG. 5C is a graph demonstrating CD spectra of 25-nt D-DNA and L-DNA oligos of the same sequence (SEQ ID NO: 3).

Figure 6B:
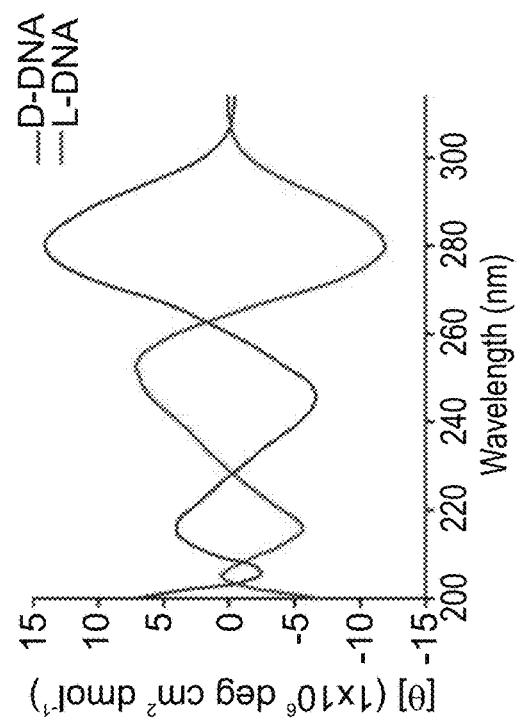
Figure 6A:
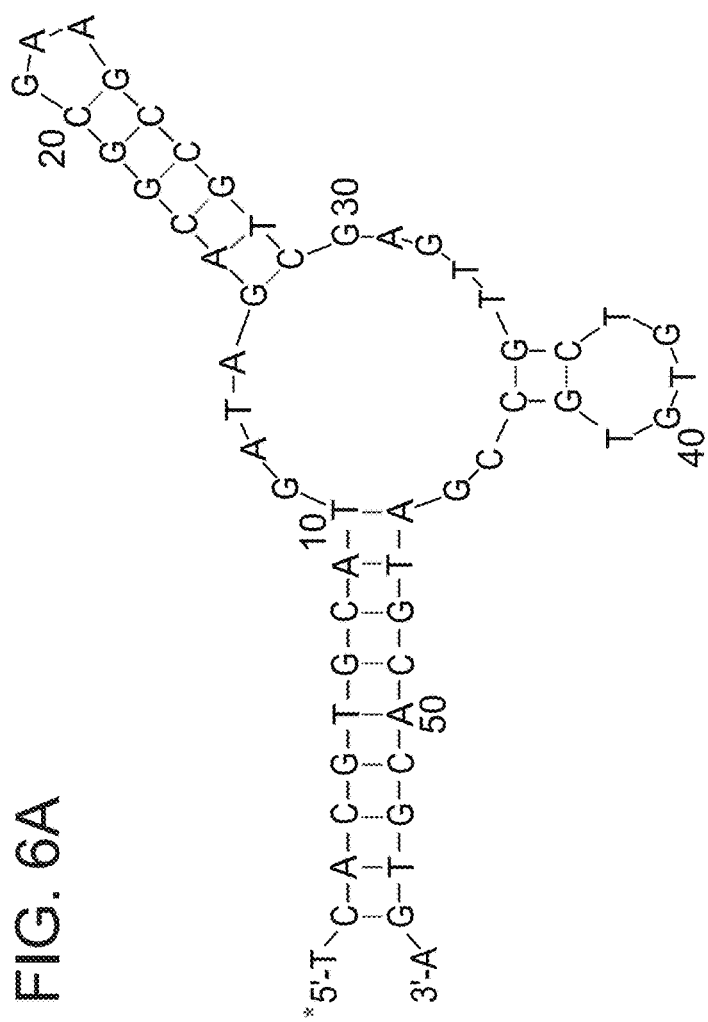
Figure 6C:
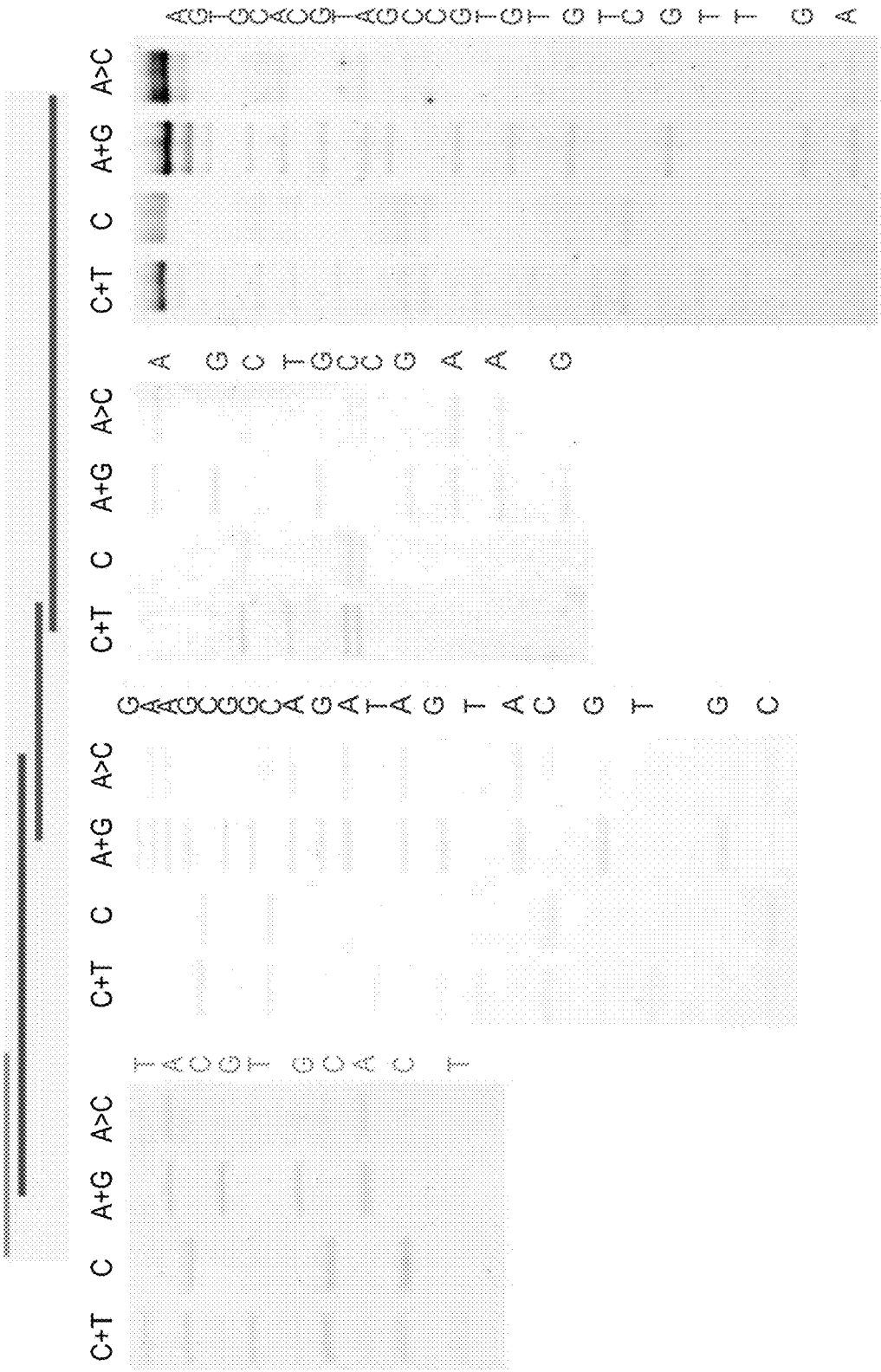

FIGS. 6A-6C demonstrate chemical sequencing of a 5'-FAM labeled 55-nt L-DNA aptamer (SEQ ID NO: 4). FIG. 6A is a Mfold-predicted secondary structure of the 55-nt L-DNA aptamer[20]. Asterisk denotes 5'-FAM label. FIG. 6B is a graph demonstrating CD spectra of 55-nt D-DNA and L-DNA aptamers of the same sequence (SEQ ID NO: 4). FIG. 6C shows multiple loading strategy for sequencing the L-DNA in four sections, indicated by four different colors that correspond to those of the determined sequences. C+T reaction was performed by treatment with 50% hydrazine at 45° C. for 5 minutes; C-specific reaction with 4 M $NH_2OH$—HCl (pH 6.0) at 90° C. for 1 minutes; A+G reaction with 66% formic acid at RT for 3 minutes; A>C reaction with NaOH at 90° C. for 12 minutes. The products were analyzed by 10% or 20% PAGE in 8 M urea scanned under FAM mode.

FIGS. 7A-7D demonstrate combinations of D-primer, template, and dNTPs or NTPs in primer extension reactions by natural Dpo4-5m and its mutants (Dpo4-6m-Y12A, Dpo4-6m-Y12G, Dpo4-6m-Y12S). FIG. 7A is a PAGE photograph demonstrating the results of an assay for DNA-dependent DNA polymerase activity with a DNA primer, a DNA template, and dNTPs.

FIG. 7B is a PAGE photograph demonstrating an assay for DNA-dependent RNA polymerase activity with a RNA primer, a DNA template, and NTPs. FIG. 7C is a PAGE photograph demonstrating the results of an assay for RNA-dependent DNA polymerase activity with a DNA primer, a RNA template, and dNTPs. FIG. 7D is a PAGE photograph demonstrating the results of an assay for RNA-dependent RNA polymerase activity with a RNA primer, a RNA template, and NTPs. All the primer reactions were effected at 65° C. for 1 hour. NC denotes negative control without an enzyme.

Figure 8:
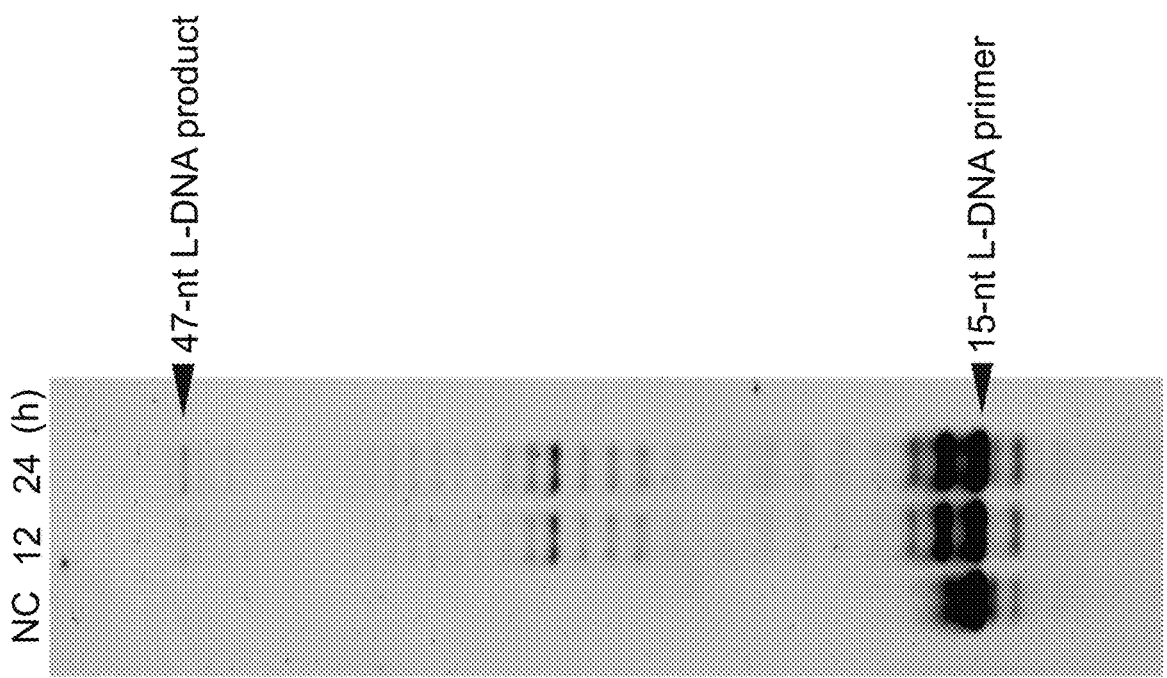

FIG. 8 demonstrates reverse transcription of a FAM-labeled 46-nt L-ribozyme RNA (SEQ ID NO: 5) by d-Dpo4-5m. Shown is a PAGE photograph demonstrating full-length extension of a 5'-FAM labeled L-DNA obtained by catalyzing an L-DNA primer annealed to an L-ribozyme RNA template with synthetic D-Dpo4-5m at 65° C. for 12 and 24 hours in the presence of L-dNTPs. NC denotes negative control without a d-enzyme.

Figure 9A:
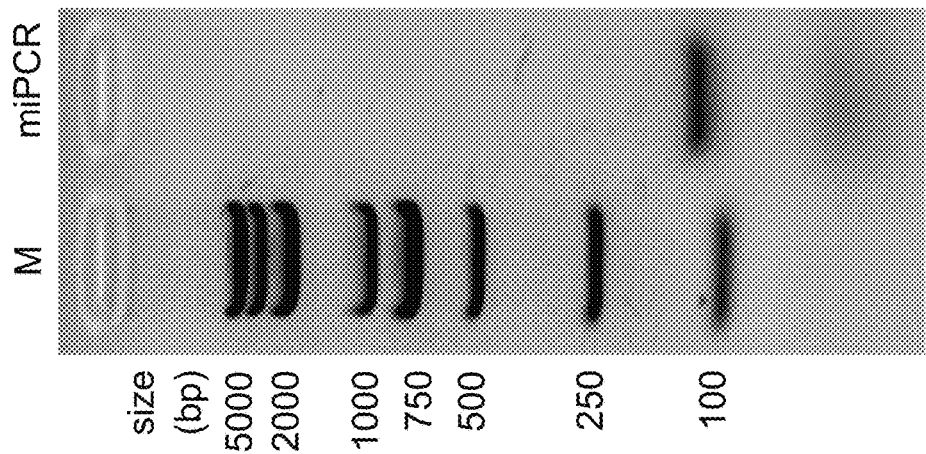

FIGS. 9A-9B demonstrates chemical sequencing of a 5'FAM labeled 120-nt L-5S DNA (SEQ ID NO: 25). FIG. 9A is an agarose gel photograph demonstrating PCR amplification of the 120-nt L-5S DNA by d-Dpo4-5m. FIG. 9B shows multiple loading strategy for sequencing the L-DNA in four sections, indicated by four different colors that correspond to those of the determined sequences. C+T reaction was performed by treatment with 50% hydrazine at 45° C. for 2.5 minutes; C-specific reaction with 4 M NH$_2$OH—HCl (pH 6.0) at 90° C. for 25 seconds; A+G reaction with 66% formic acid at RT for 2 minutes; A>C reaction with NaOH at 90° C. for 5 minutes. The products were analyzed by 8%, 10% or 20% PAGE in 8 M urea scanned under FAM mode.

Figure 10:
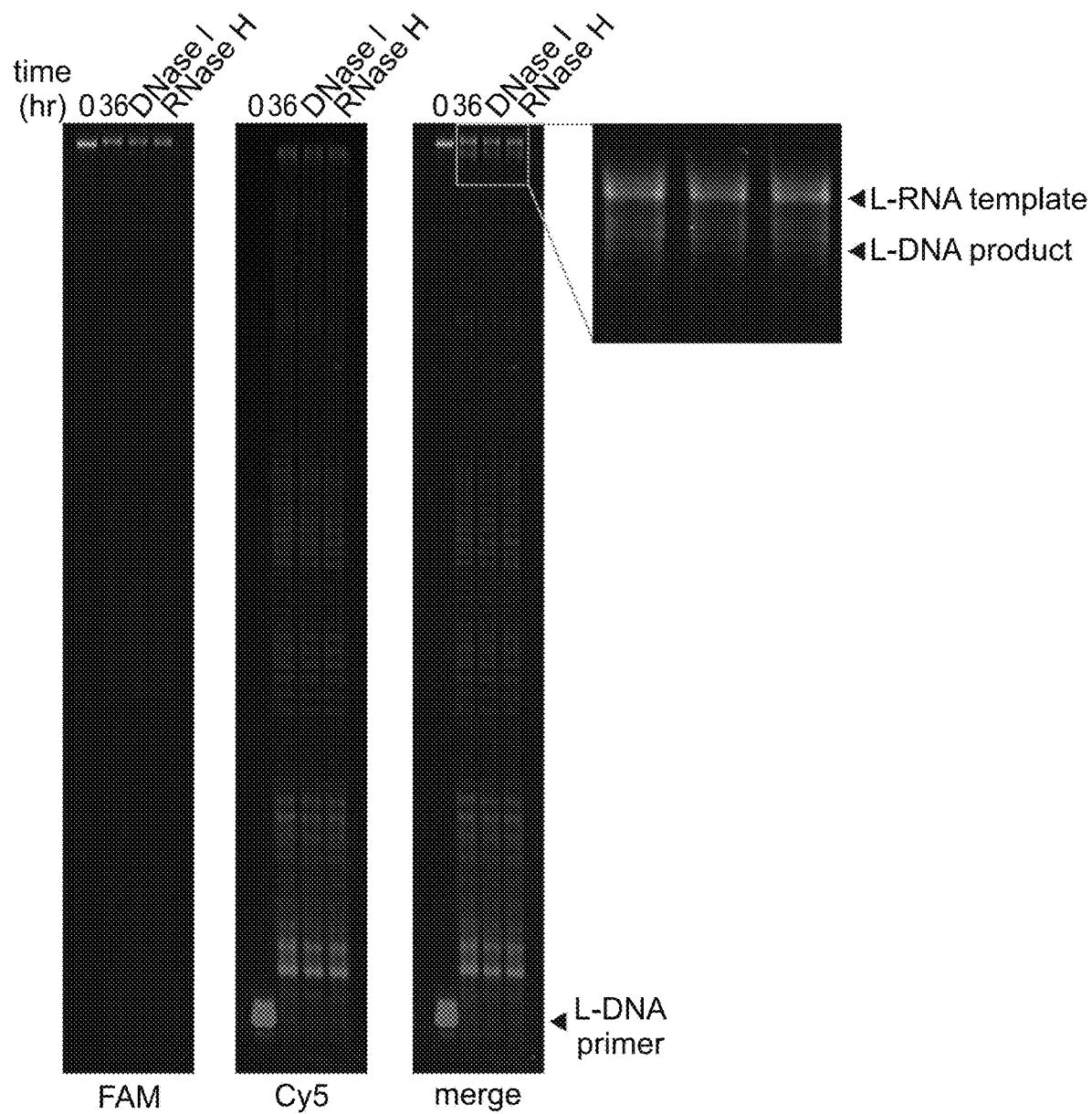

FIG. 10 demonstrates reverse transcription of a 120-nt L-ribozyme RNA (SEQ ID NO: 26) by d-Dpo4-5m. Shown is a PAGE photograph demonstrating full-length extension of a 5'-Cy5-labeled L-DNA obtained by catalyzing a 5'-Cy5-labeled L-DNA primer (SEQ ID NO: 27) annealed to an 5'-FAM-labeled L-ribozyme RNA template (SEQ ID NO: 26) with synthetic D-Dpo4-5m at 65° C. for 36 hours in the presence of L-dNTPs. Where indicated, the reverse transcription product was further treated by natural DNase I or RNase H. The products were analysed by 12% denaturing PAGE in 8 M urea scanned under FAM or Cy5 mode as indicated. Partially extended L-DNA products can be observed below the 120-nt target band. The L-RNA template and a portion of the reverse-transcribed L-DNA products were further extended due to non-templated nucleotide addition to the 3'-terminus by D-Dpo4-5m.

Figure 11:
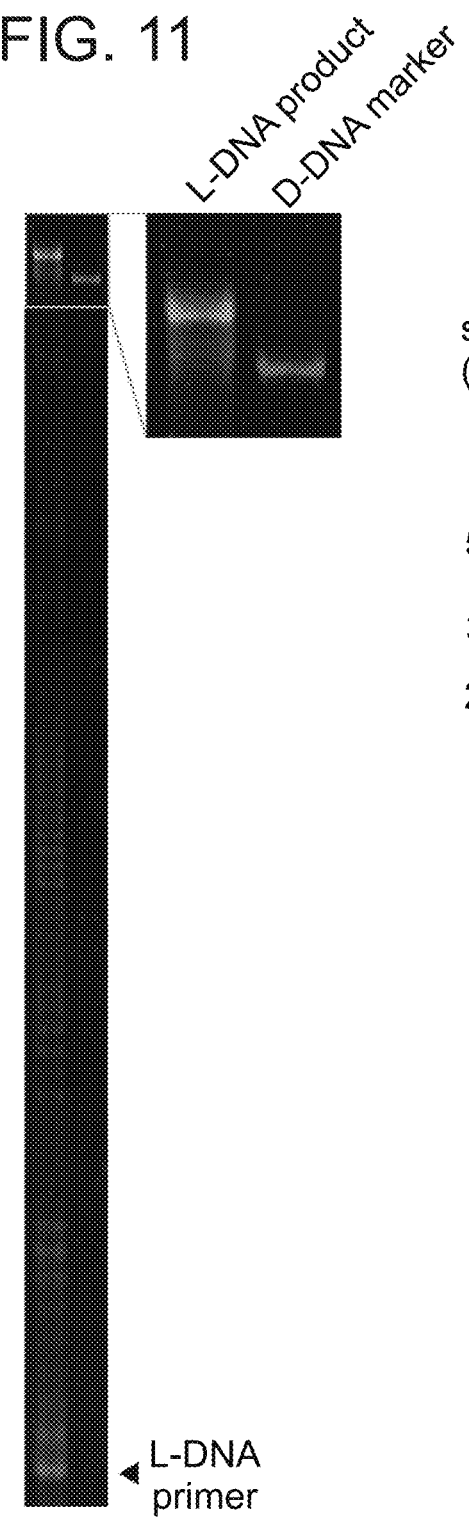

FIG. 11 is a photograph of a side-by-side PAGE of reverse transcribed 5'-Cy5-labelled L-DNA (described in FIG. 10) with 5'-Cy5-labelled D-DNA marker of the same length and sequence prepared by PCR using a Q5 high-fidelity DNA polymerase with a 5'-Cy5-labelled primer (SEQ ID NO: 28).

Figure 12:
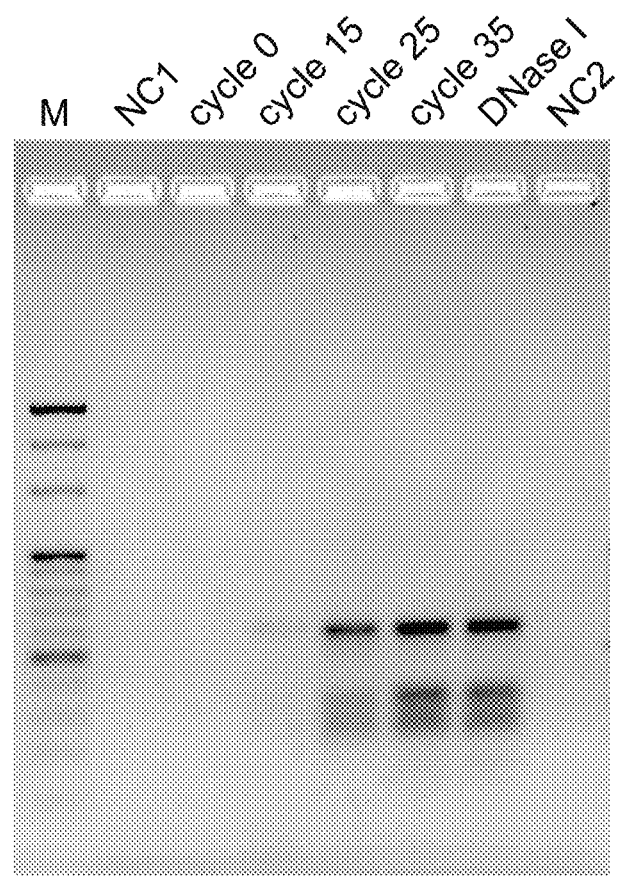

FIG. 12 demonstrates PCR amplification of the reverse transcribed 12-nt L-DNA (described in FIG. 10) by D-Dpo4-5m, sampled from multiple cycles. The PCR product was amplified, treated by natural DNase I where indicated, and analyzed by 3% sieving agarose gel electrophoresis stained by GoldView. The cycle number is indicated above the lanes; NC1 denotes negative control without reverse transcription product; NC2 denotes negative control without polymerase; and M denotes DNA marker.

FIGS. 13A-13C demonstrates reverse transcription, PCR amplification, and sequencing of 76-nt L-tRNA (SEQ ID NO: 31). FIG. 13A is a PAGE photograph demonstrating extension of a 14-nt 5'-FAM-labelled DNA primer (SEQ ID NO: 32) on a synthetic 76-nt L-tRNA (SEQ ID NO: 31) catalyzed by synthetic D-Dpo4-5m, at 65° C. for up to 24 hours. The reverse transcribed product was further treated by natural DNase I where indicated. The products were analyzed by 12% denaturing PAGE in 8 M urea. FIG. 13B demonstrates PCR amplification of the reverse transcribed product shown in FIG. 13A by D-Dpo4-5m, sampled from multiple cycles. The mirror-image PCR product was further treated by natural DNase I where indicated. The products were analyzed by 3% sieving agarose gel electrophoresis and stained by GoldView. The cycle number is indicated above the lanes; NC1 denotes negative control without reverse transcription product; NC2 denotes negative control without polymerase; and M denotes DNA marker. FIG. 13C demonstrates chemical sequencing of the amplified product described in FIG. 13B. Shown multiple loading strategy for sequencing the L-DNA in two sections, indicated by two different colors that correspond to those of the determined sequences. C+T reaction was performed by treatment with 50% hydrazine at 45° C. for 2.5 minutes; C-specific reaction with 4 M NH$_2$OH—HCl (pH 6.0) at 90° C. for 25 seconds; A+G reaction with 66% formic acid at RT for 2 minutes; A>C reaction with NaOH at 90° C. for 5 minutes. The products were analyzed by 12% or 20% denaturing PAGE in 8 M urea, respectively, and scanned under FAM mode.

DESCRIPTION OF SPECIFIC EMBODIMENTS OF THE INVENTION

The present invention, in some embodiments thereof, relates to methods of sequencing and producing nucleic acid sequences.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The development of mirror-image nucleic acids for use in medicine, diagnostics and agriculture faces a critical barrier of lacking a sensitive, accurate and reproducible L-nucleic acids sequencing technique.

Whilst reducing the present invention to practice, the present inventors have now developed a practical method for sequencing mirror-image nucleic acids by a chemical sequencing approach.

As is illustrated hereinunder and in the examples section, which follows, the present inventors show that the chemical sequencing approach they developed, through which specific nucleobases in an end-labelled L-DNA are modified by achiral chemicals (e.g. hydrazine for the C+T reaction, hydroxylamine hydrochloride for the C-specific reaction, formic acid for the A+G reaction, and methylene blue under ultraviolet (UV) irradiation for the G-specific reaction or NaOH for the A>C reaction) followed by strand scission adjacent to the modified site by treatment with piperidine, separation of the obtained fragmented products using polyacrylamide gel electrophoresis (PAGE), visualization of the bands comprising the end-label and generation of a sequencing chromatogram; enabled accurate sequencing of several L-DNA sequences (SEQ ID NOs: 1-4, Example 1, FIGS. 1A-D, 2, 3A-C, 4A-C, 5A-C, 6A-C, 9A-B).

In addition, the present inventors show that both D-RNA and L-RNA sequences can be reverse transcribed into DNA by the thermostable *Sulfolobus solfataricus* P2 DNA polymerase IV (Dpo4), using L-Dpo4 and D-Dpo4 respectively (Example 2, FIGS. 7A-D, 8, 10 and 11). Consequently, the obtained DNA can be further used for multiple applications such as, but not limited to, amplification, sequencing, cloning and single cell transcriptome analysis (Example 2, FIGS. 12 and 13A-C).

Thus, according to a first aspect of the present invention, there is provided a method of sequencing a nucleic acid sequence comprising L-nucleotides, the method comprising subjecting the nucleic acid sequence comprising the L-nucleotides to a chemical sequencing method using a chemical selected from the group consisting of Dimethyl sulfate, Methylamine, Diethyl pyrocarbonate, Methylene blue, Potassium chloropalladate, Sodium hydroxide, Osmium tetroxide, Spermine, potassium permanganate, Hydrazine, hydrazine hydrate, Hydroxylamine hydrochloride, Diethyl pyrocarbonate, Formic acid and Citrate buffer.

According to an alternative or an additional aspect of the present invention, there is provided a method of sequencing a nucleic acid sequence comprising L-nucleotides, the method comprising subjecting the nucleic acid sequence comprising the L-nucleotides to a chemical sequencing method, wherein said nucleic acid sequence comprises more than 120 nucleotides in length.

According to an alternative or an additional aspect of the present invention, there is provided a method of sequencing a nucleic acid sequence comprising L-nucleotides, the method comprising subjecting the nucleic acid sequence comprising the L-nucleotides to a chemical sequencing method, wherein said chemical sequencing method comprises gel-electrophoresis to determine said nucleic acid sequence.

According to an alternative or an additional aspect of the present invention, there is provided a method of sequencing a nucleic acid sequence comprising L-nucleotides, the method comprising:
  (a) labeling at a 5' terminus or 3' terminus of the nucleic acid sequence comprising the L-nucleotides 5-iodoacetamidofluorescein, so as to obtain a labeled nucleic acid sequence comprising the L-nucleotides; and
  (b) subjecting said labeled nucleic acid sequence comprising the L-nucleotides to a chemical sequencing method.

According to an alternative or an additional aspect of the present invention, there is provided a method of sequencing a nucleic acid sequence comprising L-nucleotides, the method comprising:
  (a) labeling at a 5' terminus of the nucleic acid sequence comprising the L-nucleotides using a polynucleotide kinase, so as to obtain a labeled nucleic acid sequence comprising the L-nucleotides; and
  (b) subjecting said labeled nucleic acid sequence comprising the L-nucleotides to a chemical sequencing method.

As used herein, the term "nucleotides" refers to naturally occurring D-nucleotides, mirror-image nucleotides (i.e. L-nucleotides) and nucleotides analogs having modified sugars which comprise an adenine (A), guanine (G), thymine (T), cytosine (C) or uracil (U) nucleobase.

According to specific embodiments, the nucleotides comprise ribose nucleotides.

As used herein, the term "ribose nucleotides" refers to a nucleotide having ribose as its sugar backbone.

According to specific embodiments, the nucleotides comprise deoxyribose nucleotides.

As used herein, the term "deoxyribose nucleotide" refers to a nucleotide having deoxyribose as its sugar backbone.

As used herein the term "nucleic acid sequence", "nucleic acid molecule" or "polynucleotide", which are interchangeably used herein, refers to a single or double stranded nucleic acid sequence wherein the nucleotides are connected to each other in a chain by at least one covalent bond between the sugar of one nucleotide and the phosphate of the next, resulting in an alternating sugar-phosphate backbone.

According to specific embodiments, the nucleic acid sequence is in the form of a nucleic acid sequence comprising ribose nucleotides (e.g. RNA sequence), a nucleic acid sequence comprising deoxyribose nucleotides [e.g. DNA or a complementary polynucleotide sequence (cDNA)] or a composite nucleic acid sequence (e.g., a combination of the above).

According to specific embodiments, the nucleic acid sequence comprises ribose nucleotides.

According to specific embodiments, the nucleic acid sequence consists of ribose nucleotides.

According to specific embodiments, the nucleic acid sequence comprises deoxyribose nucleotides.

According to specific embodiments, the nucleic acid sequence consists of deoxyribose nucleotides.

According to specific embodiments, the nucleic acid sequence is a single stranded nucleic acid sequence.

According to specific embodiments, the nucleic acid sequence is a double stranded nucleic acid sequence.

According to specific embodiments, the nucleic acid sequence comprises D-nucleotides.

According to specific embodiments, the nucleic acid sequence consists of D-nucleotides.

According to specific embodiments, the nucleic acid sequence comprises L-nucleotides.

According to specific embodiments, the nucleic acid sequence consists of L-nucleotides.

According to specific embodiments, the nucleic acid sequence consists of ribose nucleotides all being of the L-isomer.

According to specific embodiments, the nucleic acid sequence consists of deoxyribose nucleotides all being of the L-isomer.

According to specific embodiments, the nucleic acid sequence of the present invention is at least 10 nucleotides long, at least 20 nucleotides long, at least 50 nucleotides long, at least 100 nucleotides long, at least 120 nucleotides long, at least 150 nucleotides long, at least 200 nucleotides long, each possibility represents a separate embodiment of the present invention. According to a particular embodiment, the nucleic acid sequence is about 120 nucleotides long. According to a particular embodiment, the nucleic acid sequence is about 150 nucleotides long. According to a particular embodiment, the nucleic acid sequence is about 200 nucleotides long. According to a particular embodiment, the nucleic acid sequence comprises more than 120 nucleotides in length. According to a particular embodiment, the nucleic acid sequence comprises more than 150 nucleotides in length. According to still another embodiment, the nucleic acid sequence is no longer than 500 nucleotides long. According to still another embodiment, the nucleic acid sequences are no longer than 1000 nucleotides long. According to another specific embodiment, the nucleic acid sequence is 10-200, 10-500, 50-200, 50-500, 100-200, 100-500, 120-200, 120-500, 150-200 or 150-500 nucleotides long.

According to specific embodiments, nucleic acid sequence is an aptamer, spiegelmer, ribozyme, spiegelzyme, antisense molecule, siRNA molecule, shRNA, miRNA, or a decoy molecule.

According to specific embodiments, the sequencing method comprises sequencing or de-novo sequencing.

As nucleic acid sequences comprising L-nucleotides are not naturally occurring, according to specific embodiments of the present invention, the nucleic acid sequence is synthesized by any method known in the art, such as enzymatic synthesis or solid phase synthesis. Equipment and reagents for executing solid-phase synthesis are commercially available from, for example, Applied Biosystems. Any other means for such synthesis may also be employed; the actual synthesis of the nucleic acid sequence is well within the capabilities of one skilled in the art and can be accomplished via established methodologies as detailed in, for example, J. Sambrook et al., "Molecular Cloning: A Laboratory Manual", 1989, 2.sup.nd Ed., Cold Spring Harbour Laboratory Press: New York, N.Y.; "PCR Protocols: A Guide to Methods and Applications", 1990, M. A. Innis (Ed.), Academic Press: New York, N.Y.; P. Tijssen "Hybridization with Nucleic Acid Probes—Laboratory Techniques in Biochemistry and Molecular Biology (Parts I and II)", 1993, Elsevier Science; "PCR Strategies", 1995, M. A. Innis (Ed.), Academic Press: New York, N.Y.; and "Short Protocols in Molecular Biology", 2002, F. M. Ausubel (Ed.), 5.sup.th Ed., John Wiley & Sons: Secaucus, N.J.; S. A. Narang et al., Meth. Enzymol. 1979, 68: 90-98; E. L. Brown et al., Meth. Enzymol. 1979, 68: 109-151; E. S. Belousov et al., Nucleic Acids Res. 1997, 25: 3440-3444; D. Guschin et al., Anal. Biochem. 1997, 250: 203-211; M. J. Blommers et al., Biochemistry, 1994, 33: 7886-7896; and K. Frenkel et al., Free Radic. Biol. Med. 1995, 19: 373-380; and U.S. Pat. No. 4,458,066.

For example, nucleic acid sequences may be prepared using an automated, solid-phase procedure based on the phosphoramidite approach. In such a method, each nucleotide is individually added to the 5'-end of the growing oligonucleotide chain, which is attached at the 3'-end to a solid support. The added nucleotides are in the form of trivalent 3'-phosphoramidites that are protected from polymerization by a dimethoxytrityl (or DMT) group at the 5'-position. After base-induced phosphoramidite coupling, mild oxidation to give a pentavalent phosphotriester intermediate and DMT removal provides a new site for oligonucleotide elongation. The generated nucleic acid sequences are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc. (Foster City, Calif.), DuPont (Wilmington, Del.) or Milligen (Bedford, Mass.). Alternatively, nucleic acid sequences can be custom made and ordered from a variety of commercial sources well-known in the art, including, for example, the Midland Certified Reagent Company (Midland, Tex.), ExpressGen, Inc. (Chicago, Ill.), Operon Technologies, Inc. (Huntsville, Ala.), and many others.

Purification of the nucleic acid sequences, where necessary or desirable, may be carried out by any of a variety of methods well-known in the art. Purification of nucleic acid sequences is typically performed either by native acrylamide gel electrophoresis, by anion-exchange HPLC as described, for example, by J. D. Pearson and F. E. Regnier (J. Chrom., 1983, 255: 137-149) or by reverse phase HPLC (G. D. McFarland and P. N. Borer, Nucleic Acids Res., 1979, 7: 1067-1080).

According to specific embodiments, the nucleic acid sequence may be modified to contain one or more additional covalently linked (either directly or with a linker) moieties, such as, for example, polypeptides (e.g., nucleases, toxins, antibodies, signal peptides, poly-L-lysine), carbohydrates, polyethylene glycol (PEG), Hydroxyethyl starch (HES), intercalators (e.g., acridine, psoralen), chelators (e.g., metals, radioactive metals, iron, oxidative metals), and alkylators.

Furthermore, according to specific embodiments, the nucleic acid sequence of the present invention may also be modified to contain a label such as a radioactive isotope (such as $[^{125}]$iodine), a phosphorescent chemical, a chemiluminescent chemical, a fluorescent chemical (fluorophore), an enzyme, a fluorescent polypeptide, a chromophore, an affinity tag (or a member of a binding pair), a mass tag, a lipophilic tag and molecules (contrast agents) detectable by Positron Emission Tomography (PET) or Magnetic Resonance Imaging (MRI).

According to a specific embodiment, the label is a fluorescent chemical (fluorophore).

Examples of suitable fluorophores include, but are not limited to, fluorescein amidite (FAM), 5-iodoacetamidofluorescein, phycoerythrin (PE), fluorescein isothiocyanate (FITC), Cy-chrome, rhodamine, Texas red, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, U K. (2001); U.S. Pat. No. 6,350,466 to Targesome, Inc.

According to specific embodiments, the label comprises fluorescein amidite (FAM) or 5-iodoacetamidofluorescein.

According to specific embodiments, the label comprises a radioactive isotype.

According to other specific embodiments, the label is an affinity tag.

The affinity tag (or a member of a binding pair) can be for example an antigen identifiable by a corresponding antibody [e.g., digoxigenin (DIG) which is identified by an anti-DIG antibody], biotin which has a high affinity towards the streptavidin, an oligonucleotide that can bind a second oligonucleotide, calmodulin which binds a calmodulin binding peptide, albumin which binds Cibracon Blue, a metal-chelator agent which binds a metal-chelating support.

According to specific embodiments, the label comprises biotin.

According to specific embodiments, the label is directly linked to the nucleic acid sequence (e.g. at the 5' terminus or the 3' terminus).

According to other specific embodiments, the label is indirectly (e.g. using a linker) linked to the nucleic acid sequence (e.g. at the 5' terminus or the 3' terminus).

According to specific embodiments, the label is linked to the 5' terminus or the 3' terminus of the nucleic acid sequence.

According to a specific embodiment, the label is linked to the 5' terminus of the nucleic acid sequence.

According to another specific embodiment, the label is linked to the 3' terminus of the nucleic acid sequence.

Various methods, widely practiced in the art, may be employed to attach the label to the nucleic acid sequence of the invention.

The label may be directly incorporated into the nucleic acid sequence during or following synthesis. Alternatively or optionally, the label may be incorporated into the nucleic acid sequence prior to or following effecting the methods of the present invention.

Thus, according to specific embodiments, the methods comprising labeling the nucleic acid sequence at a 5' terminus or a 3' terminus, as to obtain a labeled nucleic acid sequence comprising the L-nucleotides, prior to subjecting the nucleic acid sequence to chemical sequencing.

According to a specific embodiment, the method comprises labeling the nucleic acid sequence at a 5' terminus or 3' terminus with fluorescein amidite (FAM), 5-iodoacetamidofluorescein or biotin.

According to another specific embodiment, method comprises labeling said nucleic acid sequence at a 5' terminus or 3' terminus with fluorescein amidite (FAM) or 5-iodoacetamidofluorescein.

According to specific embodiments, the method comprises labeling the nucleic acid sequence at a 5' terminus using a polynucleotide kinase.

As used herein, the term "polynucleotide kinase (PNK)", E.C. No. 2.7.1.78, refers to an enzyme that catalyzes the transfer of a gamma-phosphate from ATP to the free hydroxyl end of a 5' terminus of a nucleic acid sequence comprising L-nucleotides resulting in a product that can be end-labeled using e.g. a radioactive isotope. According to specific embodiments, the polynucleotide kinase refers to the T4 bacteriophage polynucleotide kinase or the T7 bacteriophage polynucleotide kinase.

Polynucleotide kinase can be obtained commercially from e.g. BioLabs, Promega, Thermo Fisher Scientific.

According to specific embodiments, the polynucleotide kinase comprises L-amino acids.

According to specific embodiments, the polynucleotide kinase comprises D-amino acids.

According to specific embodiments, the polynucleotide kinase consists of D-amino acids.

According to specific embodiments, wherein the nucleic acid sequence is a double stranded nucleic acid sequence the methods of the present invention may include denaturation of the double stranded nucleic acid sequence. The denaturation step can be effected in any step (e.g. prior to sequencing, prior to or following amplification, prior to cloning, following reverse transcription). The denaturation step generally comprises heating the double stranded nucleic acid sequences to an elevated temperature and maintaining it at the elevated temperature for a period of time sufficient for any double-stranded nucleic acid present in the reaction mixture to dissociate. For denaturation, the temperature of the reaction mixture is usually raised to, and maintained at, a temperature ranging from about 85° C. to about 100° C., usually from about 90° C. to about 98° C., and more usually from about 93° C. to about 96° C. for a period of time ranging from 3-240 seconds, 3-180 seconds, 2-120 seconds, 100-180 seconds.

According to specific embodiments, the methods of the present invention also comprise a carrier nucleic acid sequence.

The carrier nucleic acid sequence can be any un-labelled nucleic acid sequence, such as, but not limited to a plasmid or a genomic DNA According to specific embodiments, the carrier nucleic acid sequence is an un-labelled genomic DNA. According to specific embodiments, the carrier is an un-labelled *E. coli* genomic DNA.

According to specific embodiments, the carrier concentration is at least 1 µg/µl.

According to specific embodiments, the nucleic acid sequence is subjected to a chemical sequencing method.

As use herein the term "chemical sequencing" refers to a method of sequencing which utilizes chemicals and not enzymes in order to generate fragments of varied sizes of the nucleic acid sequence, all having identical 5'-teminues or 3' terminus.

According to specific embodiments, the chemicals are achiral [i.e. do not depend on the chirality (i.e. D or L) of the reagents for effecting the reaction].

According to specific embodiments, the chemical sequencing method utilizes non-specific (i.e. random) cleavage of the phosphodiester backbone of the nucleic acid sequence such as by acid hydrolysis, acid (e.g. formic acid), polyamines at physiological pH; as disclosed for examples in Shapiro & Danzig, 1972, Farand & Beverly, 2008, Komiyama & Yoshinari, 1997.

According to specific embodiments, the chemical sequencing method utilizes nucleobase-specific chemicals.

Non-limiting examples of nucleobase-specific chemicals which can be used with specific embodiments of the present invention include, but are not limited to Dimethyl sulfate, Methylamine, Diethyl pyrocarbonate, Methylene blue, Potassium chloropalladate, Sodium hydroxide, Osmium tetroxide, Spermine, potassium permanganate, Hydrazine, hydrazine hydrate, Hydroxylamine hydrochloride, Diethyl pyrocarbonate, Formic acid and Citrate buffer.

According to specific embodiments, the chemical is selected from the group consisting of Methylene blue, Sodium hydroxide, Hydroxylamine hydrochloride, Formic acid and hydrazine hydrate.

According to specific embodiments, the chemical sequencing is effected using a plurality of reaction mixtures in a plurality of reaction vessels such that each reaction mixture represents different populations of fragments of the nucleic acid sequence.

According to specific embodiments, the chemical sequencing is effected in at least 3 separate reaction mixtures.

According to specific embodiments, the chemical sequencing is effected in at least 4 separate reaction mixtures.

According to specific embodiments, each of the plurality of reaction mixtures is effected with a chemical specific for 1-2 nucleobases (i.e. can modify 1-2 nucleobases).

Thus, according to specific embodiments, the chemical sequencing method comprises a C+T modification reaction, a C-specific modification reaction, an A+G modification reaction, and a G-specific modification reaction.

According to other specific embodiments, the chemical sequencing method comprises a C+T modification reaction, a C-specific modification reaction, an A+G modification reaction, and an A>C modification reaction.

According to specific embodiments, the chemical sequencing method comprises a T-specific modification reaction.

Non-limiting examples of C+T modification reaction chemicals include Hydrazine hydrate or Hydrazine.

Non-limiting examples of C-specific modification reaction include hydrazine hydrate+salt or Hydroxylamine hydrochloride.

Non-limiting examples of A+G modification reaction include Diethyl pyrocarbonate pH 5, Formic acid or Citrate buffer pH 4.

Non-limiting examples of G-specific modification reaction include Dimethyl sulfate pH 7.0, Methylamine+UV, Diethyl pyrocarbonate pH 8 or Methylene blue+UV.

Non-limiting examples of A>C modification reaction include Dimethyl sulfate+acid or alkali, Potassium chloropalladate or Sodium hydroxide.

Non-limiting examples of T-specific modification reaction include Osmium tetroxide, Spermine+UV or potassium permanganate.

Non-limiting examples of U+C modification reaction chemicals include Hydrazine hydrate or Hydrazine.

A non-limiting example of U specific modification reaction includes Hydroxylamine hydrochloride pH 10.

According to a specific embodiment, the chemical sequencing method comprises C+T modification reaction with Hydrazine, a C-specific modification reaction with Hydroxylamine hydrochloride, an A+G modification reaction with formic acid, and a G-specific modification reaction with methylene blue+UV.

According to a specific embodiment, the chemical sequencing method comprises C+T modification reaction with Hydrazine, a C-specific modification reaction with Hydroxylamine hydrochloride, an A+G modification reaction with formic acid, and an A>C modification reaction with Sodium hydroxide.

According to specific embodiments, the modification reaction is effected together with any additional reaction reagents under conditions (e.g. temperature, buffer, salt, ionic strength, pH and time) that allow the modification to occur.

According to specific embodiments, the modification reaction is effected by partially modifying plurality of molecules of the nucleic acid sequence of the present invention.

As used herein, the term "partially modifying" refers to partially modifying plurality of molecules of the nucleic acid sequence of the present invention with a chemical such that upon cleaving the plurality of molecules adjacent to modified nucleobases, a plurality of fragments of different sizes and composition having an intact 5' terminus or 3' terminus are obtained. According to specific embodiments, partially modifying is such that upon cleaving the plurality of molecules adjacent to modified nucleobases all possible fragments of the nucleic acid sequence having an intact 5' terminus or 3' terminus are obtained.

According to specific embodiments, the modification reaction is effected using a plurality of reaction mixtures such that following cleaving a set of fragments comprising an intact 5' terminus or 3' terminus differing by a single nucleotide in length is obtained.

Determining the suitable conditions for obtaining such a cleavage pattern are well within the capabilities of the skilled in the art.

Thus, for example, the modification reaction may be effected in a variety of standard buffers such as but not limited to primary alkyl amines such as TRIS (tris(hydroxymethyl)aminomethane), secondary amines such as Tricine (N-(Tri(hydroxymethyl)methyl)glycine), tertiary amines such as Triethylamine, Bis-Tris (Bis(2-hydroxyethyl)-imino-tris(hydroxymethyl)-methane), polyamines such as, spermidine, HEPES (4-(2-hydroxyethyl)-1-piperazineethanesulfonic acid) and PIPES (piperazine-N,N'-bis(2-ethanesulfonic acid), quaternary ions such as tetrabutylammonium and tetraethylammonium. Buffers containing aromatic amines such as imidazole are also known in the art. Such buffers can be used in conjunction with hydrochloric, hydrofluoric, hydrobromic, phosphoric, citric, phthalic, tartaric, boric acid and others known in the art. Other suitable buffers/solutions containing alkali metals are also known in the art. Examples of which are hydroxide, carbonate, hydrogen carbonate, phosphate, phthalate, tartrate, borate and acetate. The reaction may be effected in the presence of but not limited to $Mg^{+2}$, $Ca^{+2}$, $Be^{+2}$, $Ba^{+2}$, $Fe^{+2}$, $Zn^{+2}$, $Cu^{+2}$, $Mn^{+2}$, $Cd^{+2}$, $Sr^{+2}$, $Ni^{+2}$, $Co^{+2}$, $Pb^{+2}$.

According to specific embodiments, the temperature of the modification reaction is 0-150° C., more preferably 10-100° C.

According to specific embodiments, the modification reaction is effected at 15-25° C.

According to specific embodiments, the C-specific modification reaction and/or the A>C modification reaction is effected at 80-100° C.

According to specific embodiments, the C-specific modification reaction and/or the A>C modification reaction is effected at about 90° C.

According to specific embodiments, the pH is 1-15 or 4-10.

According to specific embodiments, the C-specific modification reaction is effected at a pH of 4-8, 4-7, 5-7, 4-6 or 5-6.

According to specific embodiments, the C-specific modification reaction is effected at pH 6.

According to specific embodiments, the modification reaction is effected for 0.1 and 60 minutes, 1-60 minutes, 2-60 minutes, 2-40 minutes.

According to specific embodiments, the C+T modification reaction is effected for 5-20 minutes.

According to specific embodiments, the C-specific modification reaction is effected for 30-60 seconds.

According to specific embodiments, the C-specific modification reaction is effected for 5-30 minutes, 5-20 minutes, 10-30 minutes, 10-20 minutes.

According to specific embodiments, the C-specific modification reaction is effected for about 10 minutes.

According to specific embodiments, the C-specific modification reaction is effected for about 20 minutes.

According to specific embodiments, the A+G modification reaction is effected for 1-60 minutes, 1-50 minutes, 1-40 minutes, 3-40 minutes.

According to specific embodiments, the A+G modification reaction is effected for about 3 minutes.

According to specific embodiments, the A+G modification reaction is effected for about 10 minutes.

According to specific embodiments, the A+G modification reaction is effected for about 30 minutes.

According to specific embodiments, the G-specific modification reaction is effected at 0.5-10 minutes, 1-10 minutes, 1-5 minutes.

According to specific embodiments, the G-specific modification reaction is effected at about 2 minutes.

According to specific embodiments, the G-specific modification reaction is effected at about 2 minutes.

According to specific embodiments, the A>C modification reaction is effected at 1-20 minutes, 5-20 minutes, 10-20 minutes.

According to specific embodiments, the A>C modification reaction is effected for about 12 minutes.

According to specific embodiments, the concentration of the nucleic acid sequence in the modification reaction is 0.1-100 pmol, 1-100 pmol, 10-100 pmol.

According to specific embodiments, the concentration of the nucleic acid sequence in the modification reaction is about 20 pmol.

According to specific embodiments, the nucleic acid sequence is dissolved in water.

Non-limiting examples of modifications conditions are disclosed in the Materials and Methods and Table 2 of the Examples section which follows, which serve as an integral part of the specification of the instant application.

Typically, it is irrelevant whether or not the individual molecule is modified at a single nucleotide in each of the nucleic acids molecules or at a plurality of nucleotides in each of the nucleic acids molecule as long as the overall cleaving provides for a representation of a plurality of fragments (preferably all possible fragments) of the nucleic acid sequence.

According to specific embodiments, the modification reaction conditions are adjusted to generate a modification of a single nucleotide in each of the plurality of molecules of the nucleic acid sequence.

If a single cleavage site is generated, then two specific fragments are obtained: one having an intact 5'-terminus and one having an intact 3'-terminus. If more cleavage sites along the backbone of the nucleic acid molecule are generated then at least three fragments are obtained: one with an intact 5'-terminus, one with an intact 3'-terminus and at least one internal fragment. Thus, typically, the 5' terminus or the 3' terminus is used as a reference point for further analysis.

Hence, according to specific embodiments, the nucleic acid sequence subjected to the sequencing method comprises a modification at a 5' terminus or a 3' terminus which serves as a labeling moiety. Such labels and labeling methods are well known in the art and are further described hereinabove.

Following modification of the nucleotides, the nucleic acid sequence is fragmented by hydrolysis of the phosphodiester backbone of the nucleic acid sequence adjacent to the modified nucleotide generated by the modification reaction (referred to herein as cleavage reaction).

The cleavage reaction can be effected with any agent capable of specifically hydrolyzing the phosphodiester backbone of the nucleic acid sequence adjacent to the modified nucleotide generated by the modification reaction while not hydrolyzing the phosphodiester backbone adjacent to nucleotides not modified by the modification reaction. Such agents include, but are not limited to heat, divalent cations, base hydrolysis, acid hydrolysis, oxidative agents, reducing agents, ionization radiation, such as X-rays, UV-rays, gamma-rays.

According to specific embodiments, the cleavage reaction is effected with piperidine.

According to specific embodiments, the cleavage reaction is effected together with any additional reaction reagents under conditions (e.g. temperature, buffer, salt, ionic strength, pH and time) that allow hydrolysis of the phosphodiester backbone of the nucleic acid sequence adjacent to the modified nucleotides to occur.

Determining the suitable conditions are well within the capabilities of the skilled in the art.

Thus, for example, the cleavage reaction may be effected in a variety of standard buffers such as but not limited to primary alkyl amines such as TRIS (tris(hydroxymethyl) aminomethane), secondary amines such as Tricine (N-(Tri (hydroxymethyl)methyl)glycine), tertiary amines such as Triethylamine, Bis-Tris (Bis(2-hydroxyethyl)-imino-tris(hydroxymethyl)-methane), polyamines such as, spermidine, HEPES (4-(2-hydroxyethyl)-1-piperazineethanesulfonic acid) and PIPES (piperazine-N,N'-bis(2-ethanesulfonic acid), quaternary ions such as tetrabutylammonium and tetraethylammonium. Buffers containing aromatic amines such as imidazole are also known in the art. Such buffers can be used in conjunction with hydrochloric, hydrofluoric, hydrobromic, phosphoric, citric, phthalic, tartaric, boric acid and others known in the art. Other suitable buffers/solutions containing alkali metals are also known in the art. Examples of which are hydroxide, carbonate, hydrogen carbonate, phosphate, phthalate, tartrate, borate and acetate. The reaction may be effected in the presence of but not limited to $Mg^{+2}$, $Ca^{+2}$, $Be^{+2}$, $Ba^{+2}$, $Fe^{+2}$, $Zn^{+2}$, $Cu^{+2}$, $Mn^{+2}$, $Cd^{+2}$, $Sr^{+2}$, $Ni^{+2}$, $Co^{+2}$, $Pb^{+2}$.

According to specific embodiments, the temperature of the cleavage reaction is 0-150° C., 10-100° C., 10-100° C. or about 90° C.

According to specific embodiments, the pH is 1-15 or 4-10.

According to specific embodiments, the reaction is effected for 1-120 minutes, 1-60 minutes, 10-60 minutes, 30-50 minutes.

According to specific embodiments, the concentration of piperidine is 0.1-100 M, 1-100M, 0.1-10M, 1-10 M or about 1 M.

According to specific embodiments, the concentration of the nucleic acid sequence in the cleavage reaction is 0.1-100 pmol, 1-100 pmol, 10-100 pmol.

According to specific embodiments, the concentration of the nucleic acid sequence in the cleavage reaction is about 20 pmol.

Non-limiting examples of cleavage conditions are disclosed in the Materials and Methods of the Examples section which follows, which serve as an integral part of the specification of the instant application.

According to specific embodiments, following cleavage the fragments containing an intact 5' terminus or 3' terminus are separated from the fragments not containing an intact 5' terminus or 3' terminus.

Thus, for example, when the 5' terminus or 3' terminus comprises a label such a separation can be effected by e.g. interaction of the label with an interaction partner (e.g. chemical interaction, magnetic interaction, affinity interaction) linked to a support such as a solid support (e.g. polymers, plastics, glass, agarose, metals), followed by removal of the fragments not containing the label. Such a removal is a standard procedure as known by a person skilled in the art and include e.g. washing, filtration, dialysis, chromatography, magnetic fields, centrifugation or precipitation.

Non-limiting Examples of chemical interaction include an amine and an activated carboxylic acid, an amine plus an activated carbamate, an amine and an isocyanate/isothiocyanate, an amine plus a halide, an amine plus a maleimide moiety, an amine plus an aldehyde/ketone, a hydroxylamine or a hydrazide plus a ketone/an aldehyde, a hydrazine derivative and an activated carboxylic acid, a hydrazine and an isocyanate/isothiocyanates, a hydrazine plus a halide, a hydrazine plus a maleimide moiety, a hydrazine+an aldehyde/a ketone followed by reductive amination, a thiol plus a halide, a thiol plus a maleimide, a thiol plus an activated thiol, a thiol plus a vinyl sulfone and other Michael addition reactions, an azide plus an alkyne plus Cu salts and other "click chemistry" interaction partners (Kolb et. Al. 2001), an azide plus an activated carboxylic acid via Staudinger reaction utilising alkyl or aryl P(III) moieties, an azide plus a trivalent phosphine attached to an electrophilic trap (Staudinger ligation), an azide plus a phosphinothiol ester—traceless Staudinger ligation, an azide plus an aldehyde/a ketone+PPh to form an imine that can then be with optional reduction to the corresponding amine, a Cis-diol (e.g. as found on the 3' terminus of RNA molecules) oxidised to di-aldehyde that then forms cyclic amines for example, with either amines or hydrazine derivatives after e.g. borohydride mediated reduction, a thioester plus a cysteine—native ligation and derivatives, a phosphorothioate+an α-halocarbonyl containing conjugant, a phosphate+an amine to phosphoramidate e.g. via phosphate activation, a phosphate+an alcohol to phosphodiester e.g. via activation, an aldehyde to form secondary amines (after reduction with Borohydride), hydrazino groups to form hydrazones, semicarbazides to form semi-carbazones, a Cysteine derivative+a thioester peptide, an epoxide plus amine, an alkene/an alkyne+a diene/diyne for Diels Alder reaction, and other Pericyclic reactions, oxime formation through reacting aldehyde with a hydroxylamine, a hydroxy or amino+an epoxide.

Non-limiting Examples of affinity interactions include biotin-streptavidin interaction, antigen-antibody interaction, interaction of two oligonucleotides, interaction of calmodulin and calmodulin binding peptide, interaction of albumin and Cibracon Blue, interaction of a metal-chelator agent and metal-chelating support.

According to specific embodiments, following removal of the fragments not containing an intact 5' terminus or 3' terminus (e.g. non-labeled fragments) the interaction partner or the support is released from the fragments containing an intact 5' terminus or 3' terminus (e.g. labeled fragments).

According to specific embodiments, following removal of the non-labeled fragments the label is released from the labeled nucleic acid fragments.

Such release methods are standards procedures as known by a person skilled in the art and include e.g. enzymatic cleavage, chemical cleavage, light, temperature, pH, ion force, denaturation of the label of the interaction partner, cleavage of a linker, elution with a competitor molecule, use of organic solvents or chaotropic agents.

Determining the positions of the nucleobases in the nucleic acid sequence following the cleavage reaction by analyzing the generated fragments based on their e.g. size, mass, hydrophobicity and/or charge can be carried out using any method known in the art including, but not limited to Gel electrophoresis (e.g. Polyacrylamide gel electrophoresis), capillary electrophoresis adapted with a detector specific for the labels used in the reaction, Mass spectrometry (MS), Tandem mass spectrometry (MS-MS), chromatography, Thin Layer Chromatography (TLC), Liquid chromatography-mass spectrometry (LCMS).

According to specific embodiments, only the fragments containing an intact 5' terminus or 3' terminus are analyzed in order to determine the positions of the nucleobases in the nucleic acid sequence.

According to specific embodiments, only the fragments containing the 5' terminus or 3' terminus label are analyzed in order determine the positions of the nucleobases in the nucleic acid sequence.

According to specific embodiments, analyzing the fragments is effected by gel electrophoresis and detection of the bands using appropriate scanner, to thereby generate a ladder of the obtained fragments.

Gel electrophoresis [e.g. polyacrylamide gel electrophoresis (PAGE)] is a well-known method to the skilled in the art.

The number of gels used depends on the size of the nucleic acid sequence analyzed and can be determined by the skilled in the art.

According to specific embodiments, the fragments are loaded on a single gel.

According to other specific embodiments, the fragments are loaded on several gels, optionally each of the gels in a different concentration.

The gel concentration depends on the size of the fragments and can be determined by the skilled in the art.

According to specific embodiments, the polyacrylamide gel comprises 5-30%, 5-20%, 10-30%, or 10-20% polyacrylamide, each possibility represents a separate embodiment of the claimed invention.

According to specific embodiments, the polyacrylamide gel comprises up to 20% polyacrylamide.

According to specific embodiments, only the fragments containing the label are visualized in the gel, for example by scanning the gel under a mode compatible for the label (e.g. the labeled fragment present different absorbance at a given wavelength compared to the non-labeled fragment).

According to specific embodiments, when MS is used the nucleic acid sequence is further ionized using e.g. electrospray ionization (ESI), matrix-assisted laser desorption/ionization (MALDI), Laser Desorption Ionization (LDI), Desorption electrospray ionization (DESI), Desorption ionisation on silica (DIOS), Surface-enhanced laser desorption/ionization (SELDI), Surface-enhanced neat desorption (SEND), Surface-assisted laser desorption/ionization (SALDI), Secondary Ions Mass Spectrometry (SIMS).

According to other specific embodiments, the method does not comprise mass-spectrometry (MS).

According to specific embodiments, following analysis of the generated fragments based on their e.g. size, mass, hydrophobicity and/or charge, the nucleic acid sequence is deduced according to the pattern of the different fragments, using e.g. a sequencing chromatogram using a software well known in the art such as, but not limited to ImageQuant.

Non-limiting examples of such analysis and deduction are disclosed in the Materials and method, Example 1 and FIGS. 1B-C, 3B-C, 4B-C, 5A-B and 6C of the Examples section which follows.

Thus, in line with the teachings disclose hereinabove, according to specific embodiments, the chemical sequencing method comprises:
(a) labeling a plurality of molecules of said nucleic acid sequence at a 5' terminus or 3' terminus of said plurality of molecules with a label;
(b) partially modifying said plurality of molecules following said (a) using a nucleobase-specific chemical agent such that upon cleaving said plurality of molecules adjacent to modified nucleobases a plurality of fragments of said nucleic acid sequence comprising said label are obtained;
(c) cleaving said plurality of molecules following said (b) adjacent to modified nucleobases; and
(d) determining said modified nucleobases positions in said nucleic acid sequence according to lengths, masses and/or charges of fragments produced by said cleaving and comprising said label.

According to specific embodiments, a plurality of molecules comprises 10-20 pmol.

According to specific embodiments, (b) is effected in at least 3 separate reaction mixtures so as to create a set of fragments comprising said label differing by a single nucleotide in length.

As shown in the Examples section which follows, the present inventors further uncovered that the thermostable *Sulfolobus solfataricus* P2 DNA polymerase IV (Dpo4) can function as a reverse transcriptase.

Thus, according to another aspect of the present invention there is provided a method of reverse transcribing a ribose nucleic acid sequence into a deoxyribose nucleic acid sequence, the method comprising catalyzing reverse transcription of the ribose nucleic acid sequence with a *Sulfolobus solfataricus* P2 DNA polymerase IV (Dpo4).

According this aspect of the present invention the ribose nucleic acid sequence can be extracted and optionally purified from any source comprising ribose nucleic acids or can be synthesized by any method known in the art as further disclosed hereinabove.

Thus, according to specific embodiments, the nucleic acid sequence may comprise an RNA sequence such as total RNA, mRNA, mitochondrial RNA, chloroplast RNA, DNA-RNA hybrids, viral RNA, cell free RNA or mixtures thereof.

Methods of RNA extraction are well-known in the art and are disclosed for examples in J. Sambrook et al., "Molecular Cloning: A Laboratory Manual", 1989, 2.sup.nd Ed., Cold Spring Harbour Laboratory Press: New York, N.Y.; P. Sunnucks et al., Genetics, 1996, 144: 747-756; S. M. Aljanabi and I. Martinez, Nucl. Acids Res. 1997, 25: 4692-4693; S. Gustincich et al., BioTechniques, 1991, 11: 298-302; and J. B. W. Hammond et al., Biochemistry, 1996, 240: 298-300.

There are also numerous versatile kits that can be used to extract RNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), and Qiagen Inc. (Valencia, Calif.). User Guides that describe in great detail the protocol to be followed are usually included in all these kits.

"*Sulfolobus solfataricus* P2 DNA polymerase IV (Dpo4)" is known as a DNA polymerase belonging to the DinB/UmuC superfamily. The Dpo4 of the present invention is capable of at least catalyzing reverse transcription of a ribose nucleic acid sequence to a deoxyribose nucleic acid sequence (i.e. reverse transcriptase). Methods of determining reverse transcriptase activity are well known in the art and include digestion by RNase H, but not by DNase I following the reaction. According to specific embodiments, the Dpo4 refers to the full length protein, such as provided in the following GenBank Numbers AAK42588 (SEQ ID NO: 6) and Q97W02 (SEQ ID NO: 7) or a functional homolog thereof having the RT activity, as described hereinbelow.

According to specific embodiments, the Dpo4 comprises an amino acid sequences selected from the group consisting of SEQ ID Nos: 8-9.

According to specific embodiments, the Dpo4 of the invention is extracted and purified from *Sulfolobus solfataricus*.

According to specific embodiment, the Dpo4 of the invention is recombinantly expressed and extracted from e.g. *Escherichia coli*.

According to other specific embodiments, the Dpo4 of the invention may be synthesized and purified by any techniques that are known to those skilled in the art of peptide synthesis, such as, but not limited to, solid phase and recombinant techniques.

Dpo4 can be obtained commercially, for example wild type L-Dpo4 can be commercially obtained from e.g. Trevigen.

The term also encompasses functional homologues (naturally occurring or synthetically/recombinantly produced) which exhibit the desired activity (i.e., reverse transcriptase). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 6-9 or 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

Sequence identity or homology can be determined using any protein or nucleic acid sequence alignment algorithm such as Blast, ClustalW, and MUSCLE.

According to specific embodiments, the Dpo4 comprises one or more amino acid point mutations in SEQ ID NOs: 6-9 which exhibit the desired activity (i.e. reverse transcriptase). Non-limiting examples of such Dpo4 sequences are disclosed for example in Xu W et al. Cell Discovery (2017) 3: 17008; and Jiang, W. et al. Cell discovery (2017) 3: 17037, and are also set forth in SEQ ID NOs: 10-17.

Non-limiting examples of such point mutations include Y12S, Y12A, Y12G, C31S, S86C, N123A, S207A and/or S313A, corresponding to the Dpo4 amino acid sequence set forth in SEQ ID NO: 9.

According to specific embodiments, the Dpo4 comprises an amino acid sequence selected from the group consisting of SEQ ID NOs: 10-11.

According to specific embodiments, the Dpo4 comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identity to SEQ ID NOs: 10 or 11.

According to specific embodiments, the Dpo4 comprises Isosteric Nle instead of methionine residues (e.g. in Met1, Met76, Met89, Met157, Met216 and/or Met251 of SEQ ID NOs: 6-17).

The functional homologs also refer to functional portions of Dpo4 which maintain the activity of the full length protein (i.e. reverse transcriptase).

The Dpo4 of the present invention can comprise both L- and D-amino acids.

According to specific embodiments, the Dpo4 consists of L-amino acids (L-Dpo4).

According to specific embodiments, the Dpo4 consists of D-amino acids (D-Dpo4).

According to specific embodiments, the ribose nucleic acid sequence is a D-ribose nucleic acid sequence and the Dpo4 is an L-Dpo4.

According to specific embodiments, the ribose nucleic acid sequence is an L-ribose nucleic acid sequence and the Dpo4 is a D-Dpo4.

According to specific embodiments, the reverse transcription is effected under conditions (e.g. reagents, temperature, buffer, salt, ionic strength, pH, time and the like) that allow reverse transcription to occur.

The Reverse transcription reaction conditions which include, but not limited to, reagents, temperature, buffer, salt, ionic strength, pH and the like may readily be selected and/or designed by one skilled in the art.

Thus, for example, in a reverse transcription reaction, the conditions generally comprise primer annealing and primer extension reaction.

Typically, in order to reverse transcribe a ribose nucleic acid sequence a primer is required that hybridizes to the 3' end of the ribose nucleic acid sequence. Hence, according to specific embodiments, the reverse transcription method is effected in the presence of a primer that hybridizes to a 3' terminus of said ribose nucleic acid sequence. Annealing temperature and timing are determined both by the efficiency with which the primer is expected to anneal to a template and the degree of mismatch that is to be tolerated.

The annealing temperature is usually chosen to provide optimal efficiency and specificity, and can range for example between about 15-65° C., 15-50° C. or 15-25° C. Annealing conditions are generally maintained for a period of time ranging from about 15 seconds to about 30 minutes, usually from about 30 seconds to about 5 minutes.

A "primer," as used herein, refers to a nucleic acid sequence, generally with a free 3'-OH group, that hybridizes with a nucleic acid template sequence and is capable of promoting polymerization of a polynucleotide complementary to the template in the presence of a catalyzing polymerase (e.g. RNA-dependent DNA polymerase, DNA-dependent DNA polymerase activity). A "primer" can be, for example, an oligonucleotide (e.g., 2-200 nucleic acid sequence). A primer may contain a non-hybridizing sequence that constitutes a tail on the primer. A primer may still be hybridizing even though its sequences are not completely complementary to the target.

An oligonucleotide primer is often a synthetic polynucleotide that is single stranded, containing a sequence at its 3'-end that is capable of hybridizing with a sequence of the target nucleic acid sequence. Normally, the 3' region of the primer that hybridizes with the target nucleic acid has at least 80%, preferably 90%, more preferably 95%, most preferably 100%, complementarity to a sequence or primer binding site. The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 or 12 to about 200 nucleotides, usually about 15 to about 50 nucleotides. In general, the target nucleic acid sequence is larger than the oligonucleotide primer or primers as described previously.

According to specific embodiment, the primer comprises a barcode sequence (i.e. identification sequence), which may be used to identify a particular molecule, sample or library.

The primer may comprise a modification (e.g. tag, label) at its 5' terminus. The modification can optionally include one or more ligand, blocking group, phosphorylated nucleotide, phosphorothioated nucleotide, biotinylated nucleotide, digoxigenin-labeled nucleotide, methylated nucleotide, uracil, sequence capable of forming a hairpin structure, oligonucleotide hybridization site, restriction endonuclease recognition site, promoter sequence, nucleotides that are necessary for a sequencing process in a downstream reaction and/or cis regulatory sequence.

Methods of synthesizing primers (e.g. oligonucleotides) are known in the art and are further described herein above.

According to specific embodiments, following annealing of a primer to the ribose nucleic acid sequence, Dpo4 catalyzes reverse transcription of the target ribose nucleic acid sequence by extending the annealed primer to thereby synthesize a ribose nucleic acid-deoxyribose nucleic acid hybrid.

According to specific embodiments, the primer extension reaction is effected at 50-80° C., 55-75° C., 60-70° C.

According to specific embodiments, the primer extension reaction is effected at about 65° C.

According to specific embodiments, the primer extension reaction is effected for 2-120 hours, 24-120 hours or 36-96 hours.

The conditions that allow reverse transcription to occur encompass also reagents used in reverse transcription and may include, but are not limited to, buffers (e.g. HEPES), reducing agent such as Dithiothreitol (DTT) and $MnCl_2$, enzyme cofactors such as magnesium or manganese, salts, nicotinamide adenine dinucleotide (NAD) and deoxynucleoside triphosphates (dNTPs), such as deoxyadenosine triphosphate, deoxyguanosine triphosphate, deoxycytidine triphosphate and thymidine triphosphate, RNase inhibitor.

Hence, according to specific embodiments, the reverse transcription method is effected in the presence of dNTPs.

According to specific embodiments, following reverse transcription a double stranded nucleic acid sequence is synthesized from the ribose nucleic acid-deoxyribose nucleic acid hybrid.

Thus, according to specific embodiments, the method comprises synthesizing a complementary sequence to the single stranded deoxyribose nucleic acid sequence so as to generate a double stranded deoxyribose nucleic acid sequence by incubating the sample in the presence of dNTPs and a DNA polymerase.

Commercial kits are available for this step which include additional enzymes such as RNAse H (to remove the RNA strand) and buffers.

As the present inventors uncovered that Dpo4 can function as a reverse transcriptase the methods utilizing this activity of Dpo4 can be effected in any application comprising a step of reverse transcription. Such applications include, but are not limited to, amplification, sequencing, cloning and transcriptome analysis.

According to specific embodiments, the nucleic acid sequence of the present invention comprises an adapter nucleic acid sequence which is capable of aiding in a downstream reaction, such as an amplification reaction, sequencing reaction, cloning and transcriptome analysis.

Thus, according to an aspect of the present invention, there is provided a method of amplifying a ribose nucleic acid sequence, the method comprising catalyzing reverse transcription of the ribose nucleic acid sequence with a Dpo4 into a deoxyribose nucleic acid sequence and amplifying the deoxyribose nucleic acid sequence.

As used herein, the term "amplification" refers to a process that increases the representation of a population of a specific nucleic acid sequence in a sample by producing multiple (i.e., at least 2) copies of the desired sequence. Methods for nucleic acid amplification which can be used with specific embodiments of the present invention are known in the art and include, but are not limited to, polymerase chain reaction (PCR), which includes, but is not limited to Allele-specific PCR, Assembly PCR or Polymerase Cycling Assembly (PCA), Asymmetric PCR, Helicase-dependent amplification, Hot-start PCR, Intersequence-specific PCR (ISSR), Inverse PCR, Ligation-mediated PCR, Methylation-specific PCR (MSP), Miniprimer PCR, Multiplex Ligation-dependent Probe Amplification, Multiplex-PCR, Nested PCR, Overlap-extension PCR, Quantitative PCR (Q-PCR), Reverse Transcription PCR (RT-PCR), real-time PCR (qRT-PCR), Solid Phase PCR: encompasses multiple meanings, including Polony Amplification (where PCR colonies are derived in a gel matrix, for example), Bridge PCR (primers are covalently linked to a solid-support surface), conventional Solid Phase PCR (where Asymmetric PCR is applied in the presence of solid support bearing primer with sequence matching one of the aqueous primers) and Enhanced Solid Phase PCR (where conventional Solid Phase PCR can be improved by employing high Tm and nested solid support primer with optional application of a thermal 'step' to favor solid support priming), Thermal asymmetric interlaced PCR (TAIL-PCR), Touchdown PCR (Step-down PCR), PAN-AC and Universal Fast Walking.

A typical amplification reaction is carried out by contacting a forward and reverse primer (a primer pair) to the nucleic acid sequence described herein together with any additional amplification reaction reagents under conditions which allow amplification of the target sequence.

Thus, according to specific embodiments, the method comprises contacting the nucleic acid sequence following reverse transcription with a forward primer and a reverse primer.

The amplification conditions which include, but not limited to, reagents, temperature, buffer, salt, ionic strength, pH, enzymes and the like may readily be selected and/or designed by one skilled in the art.

Thus, for example, amplification conditions generally comprise conditions that promote annealing and/or extension of primer sequences. Such conditions are well-known in the art and depend on the amplification method selected. Thus, for example, in a PCR reaction, amplification conditions generally comprise thermal cycling, i.e., cycling of the reaction mixture between two or more temperatures. In isothermal amplification reactions, amplification occurs without thermal cycling although an initial temperature increase may be required to initiate the reaction.

The amplification conditions encompass also reagents used in amplification and may include, but are not limited to, buffers, reagents, enzymes having polymerase activity or exonuclease activity, enzyme cofactors such as magnesium or manganese, salts, nicotinamide adenine dinucleotide (NAD) and deoxynucleoside triphosphates (dNTPs), such as deoxyadenosine triphosphate, deoxyguanosine triphosphate, deoxycytidine triphosphate and deoxythymidine triphosphate. Amplification reagents may readily be selected by one skilled in the art depending on the amplification method used.

According to specific embodiments, the amplification is effected by Dpo4.

Amplification products obtained using primers of the present invention may be detected using gel electrophoresis and visualization by ethidium bromide staining and exposure to ultraviolet (UV) light or by sequence analysis of the amplification product.

According to specific embodiments, following amplification a ribose nucleic acid sequence is synthesized from the amplified deoxyribose nucleic acid sequence by incubating with a corresponding ribose nucleic acid polymerase.

Commercially available kits may be used such as, but not limited to, the T7 High Yield RNA polymerase IVT kit (New England Biolabs).

According to specific embodiments, the ribose nucleic acid polymerase is Dpo4.

According to another aspect of the present invention, there is provided a method of sequencing a ribose nucleic acid sequence, the method comprising catalyzing reverse transcription of the ribose nucleic acid sequence with a Dpo4 into a deoxyribose nucleic acid sequence and sequencing said deoxyribose nucleic acid sequence.

According to specific embodiments, the sequencing is effected under conditions which allow sequencing of the target sequence. Such condition encompass all reaction conditions including, but not limited to, temperature, buffer, salt, ionic strength, pH, enzymes and the like.

Sequencing of the deoxyribose nucleic acid sequence according to this aspect of the present invention can be effected using any suitable sequencing method known in the art including chemical and enzymatic sequencing methods. According to specific embodiments, sequencing of the deoxyribose nucleic acid sequence is effected by a chemical sequencing method. Sequencing methods are well known to the skilled in the art and are described for example in: Sanger, F. et al., Proc. Natl. Acad. Sci. U.S.A. 75, 5463-5467 (197); A. M. Maxam and W. Gilbert, Methods of Enzymology, 1980, 65: 499-560); Zimmern & Kaesberg; M. et al., Science 281, 363, 365 (1998); Lysov, 1. et al., Dokl Akad Nauk SSSR 303, 1508-1511 (1988); Bains W. & Smith G. C. J. Theor Biol 135, 303-307 (1988); Drnanac, R. et al., Genomics 4, 114-128 (1989); Khrapko, K. R. et al., FEBS Lett 256.118-122 (1989); Pevzner P. A. J Biomol Struct Dyn 7, 63-73 (1989); Branch et al, 1989; Donis-Keller et al, 1977; Gupta et al, 1976; Gupta & Randerath, 1977; Lockard et al, 1978; Proudnikov & Mirzabekov, 1996; Stanley & Vassilenko, 1978; Tanaka et al, 1980; Waldmann et al, 1987; Wu et al, 1996 and Southern, E. M. et al., Genomics 13, 1008-1017 (1992). Such sequencing methods include, but are not limited to Maxam-Gilbert sequencing, Sanger sequencing method, Chain-termination methods, Shotgun sequencing, Bridge PCR, Massively parallel signature sequencing (MPSS), Polony sequencing, pyrosequencing, Illumina (Solexa) sequencing, SOLiD sequencing, Ion Torrent semiconductor sequencing, DNA nanoball sequencing, Heliscope single molecule sequencing, Single molecule real time (SMRT) sequencing, Nanopore DNA sequencing, Matrix-assisted laser desorption ionization time-of-flight (MALDI-TOF) mass spectrometry (U. Pieles et al., Nucleic Acids Res., 1993, 21: 3191-3196), mass spectrometry following a combination of alkaline phosphatase and exonuclease digestions (H. Wu and H. Aboleneen, Anal. Biochem. 2001, 290: 347-352), Pyrophosphate-based sequencing reaction as described, e.g., in U.S. Pat. Nos. 6,274,320, 6,258, 568 and 6,210,891.

Analysis of the products obtained in these sequencing methods for elucidation of sequence information can be carried out using any of various methods known in the art. Such methods include, but are not limited to gel electrophoresis and detection of the labeled bands using appropriate scanner, sequencing gel electrophoresis and detection of the radiolabeled band directly by phosphorescence, capillary electrophoresis adapted with a detector specific for the labels used in the reaction, Mass spectrometry (MS), Tandem mass spectrometry (MS-MS), chromatography, Thin Layer Chromatography (TLC), Liquid chromatography-mass spectrometry (LCMS), and the like.

According to specific embodiments, sequencing the deoxyribose nucleic acid sequence following reverse transcription is effected by a chemical sequencing method.

According to specific embodiments, sequencing the deoxyribose nucleic acids sequence following reverse transcription is effected according to the sequencing methods of the present invention which are disclosed hereinabove and in the Examples section which follows.

Thus, according to an aspect of the present invention, there is provided a method of sequencing a nucleic acid sequence comprising L-ribose nucleotides, the method comprising catalyzing reverse transcription of the nucleic acid sequence comprising the L-ribose nucleotides with a D-Dpo4 into a nucleic acid sequence comprising L-deoxyribose nucleotides, and subjecting said nucleic acid sequence comprising said L-deoxyribose nucleotides to a chemical sequencing method.

According to another aspect of the present invention, there is provided a method of cloning an expression product of interest, the method comprising catalyzing reverse transcription of a ribose nucleic acid sequence encoding the expression product of interest with Dpo4 into a deoxyribose nucleic acid sequence and cloning said deoxyribose nucleic acid in a host-cell.

Cloning the deoxyribose nucleic acid sequence in a host-cell can be effected by any method known in the art.

A variety of prokaryotic or eukaryotic cells can be used as host-cells to express the deoxyribose nucleic acid sequences of some embodiments of the invention. These include, but are not limited to, microorganisms (e.g. bacteria), yeast, plant cells, insects and mammalian cells.

To express an exogenous deoxyribose nucleic acid sequence in a host-cell, the deoxyribose nucleic acid sequence is preferably ligated into a nucleic acid construct suitable for expression in the host-cell. Such a nucleic acid construct includes a promoter sequence for directing transcription of the nucleic acid sequence in the cell in a constitutive or inducible manner.

Examples for mammalian nucleic acids constructs include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Nucleic acids constructs containing regulatory elements from eukaryotic viruses such as retroviruses can be also used.

Various methods can be used to introduce the nucleic acids construct of some embodiments of the invention into host-cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

According to another aspect of the present invention, there is provided a method of determining a transcriptome of a cell, the method comprising catalyzing reverse transcribing ribose nucleic acid sequences expressed in the cell with Dpo4 into deoxyribose nucleic acid sequences.

Determining a transcriptome of a cell can be effected by any method known in the art which utilizes a step of reverse transcription of the ribose nucleic acid sequences (e.g. mRNA) expressed in the cell. Such methods include, but are not limited to sequencing and hybridization based techniques such as SAGE, microarray and sequencing of full length cDNA or cDNA fragments; and disclosed for examples in Cloonan, N., et al. (2008) Nat. Methods, 5, 613-619; Plessy, C., et al. (2010) Nat. Methods, 7,528-534; Islam, S., et al., (2011) Genome Res., 21, 1160-1167; Ko, J. H. and Lee, Y. (2006) J. Microbiol. Methods, 64, 297-304; Ramskold, D., et al. (2012), Nat. Biotechnol., 30, 777-782; Tang et l., Nucleic Acids Research, 2012, 1-12; Esumi et al., Neurosci. Res. 60:439-451 (2008) and Kurimoto et al., Nucleic Acids Res. 34:42 (2006); US Patent Application Publication Nos. 20110189679 and 20150307874; and International Patent Application Publication Nos. WO2010117620A2, WO2014108850, WO2013130674 and WO2012148477, each of which is fully incorporated herein by reference.

Such methods of determining a transcriptome of a cell may include a step of isolation, extraction or derivation of the ribose nucleic acid sequences expressed in the cell, amplification, sequencing, labeling, transcribing a ribose nucleic acid sequence, fragmenting the nucleic acid sequence and/or microarray analysis, using method well-known to the skilled in the art, some of them are described in details in any of the methods described hereinabove.

According to specific embodiments, determining the transcriptome is effected under conditions which allow determining the transcriptome of a cell. Such condition encompass all reaction conditions including, but not limited to, temperature, buffer, salt, ionic strength, pH, enzymes and the like. Non-limiting examples of such conditions are described in details in any of the methods described hereinabove.

The cell according to this aspect of the present invention may be derived from any source including a plant, fungi, eubacteria, archaebacteria, protist, or animal. According to specific embodiments the cell is derived from a mammal. The cell may be cultured cells, which may be primary cells or cells from an established cell line, among others. The cell may be a cellular sample isolated initially from a multicellular organism in any suitable form.

According to specific embodiments, the cell comprises a plurality of non-homologous cells. According to other specific embodiments, the cell comprises a plurality of homologous cells. Such a plurality of cell can be obtained for example from a tissue sample, an organ, a biopsy or a cell culture.

According to still other embodiments, the cell is a single cell.

According to specific embodiments, the cell comprises a plurality of single cells wherein the ribose nucleic acid sequences in each individual ribose nucleic acid sequences sample is from a single cell.

Single cells may be isolated for example by laser capture microdissection, or by microcapillary, and marker genes may be used to locate cells of interest by e.g. flow cytometry cell sorting or other methods known in the art.

According to a particular embodiment, droplet based microfluidics is used to separate single cells into droplets—see for example WO 2013134261, the contents of which are incorporated herein by reference.

The components necessary to carry out any of the methods described herein may be provided individually or may be comprised in a kit.

Thus, according to an aspect of the present invention, there is provided a kit comprising chemicals for chemical sequencing of a nucleic acid sequence comprising L-nucleotides and a positive control template comprising a nucleic acid sequence comprising L-nucleotides.

According to specific embodiments, the kit is for sequencing a nucleic acid sequence comprising L-nucleotides.

According to specific embodiments, the kit comprises a label for labeling said nucleic acid sequence comprising said L-nucleotides at a 5' terminus or a 3' terminus of said nucleic acid sequence.

According to specific embodiments, the kit comprises a polynucleotide kinase.

According to another aspect of the present invention, there is provided a kit comprising a *Sulfolobus solfataricus* P2 DNA polymerase IV (Dpo4) and a positive control template sequence comprising a ribose nucleic acid sequence.

According to specific embodiments, the kit is for reverse transcribing a ribose nucleic acid sequence.

According to specific embodiments, the kit is for amplification, sequencing, cloning and/or determining a transcriptome of a cell comprising reverse transcribing a ribose nucleic acid sequence.

According to specific embodiments, the kit comprises dNTPs.

According to specific embodiments, the kit comprises a primer that hybridizes to a 3' terminus of said positive control template sequence comprising said ribose nucleic acid sequence.

Any of the above describe kits may also comprise additional components such as a primer, an adapter polynucleotide, an enzyme (e.g. a reverse transcriptase, a ligase, a DNA polymerase, RNA polymerase, RNAse H, DNase, exonuclease and the like), RNAse inhibitor, DNase inhibitor, a labeling agent, a linker, reagents and buffers. Non-limiting examples of such components are described in details in any of the methods described hereinabove and in the Examples section which follows.

Preferably, each of these components are packaged in separate packaging.

The containers of the kits will generally include at least one vial, test tube, flask, bottle, syringe or other containers, into which a component may be placed, and preferably, suitably aliquoted. Where there is more than one component in the kit, the kit also will generally contain a second, third or other additional container into which the additional components may be separately placed. However, various combinations of components may be comprised in a container.

When the components of the kit are provided in one or more liquid solutions, the liquid solution can be an aqueous solution. However, the components of the kit may be provided as dried powder(s). When reagents and/or components are provided as a dry powder, the powder can be reconstituted by the addition of a suitable solvent.

A kit will preferably include instructions for employing the kit components as well as the use of any other reagent not included in the kit. Instructions may include variations that can be implemented.

As used herein the term "about" refers to ±10% The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Materials—L-DNA oligos and L-RNA oligo were ordered from ChemGenes (MA, U.S.) or synthesized by a MerMade-192e DNA synthesizer with L-deoxynucleoside phosphoramidites and L-nucleoside phosphoramidites purchased from ChemGenes (MA, U.S.). D-DNA oligos were ordered from Genewiz (Beijing, China). All the DNA oligos were purified by HPLC as well as PAGE. The FAM label was introduced during the solid phage synthesis of the oligonucleotides. The PAGE DNA Purification Kit was purchased from Tiandz (Beijing, China). The FAM labelled L-DNA oligos, D-DNA oligos, and L-RNA oligos used are shown in Table 1 below. Glycogen was purchased from Ferenmentas (MS, U.S.). *Escherichia coli* (*E. coli*) genomic DNA was isolated from the *E. coli* strain K12 sub-strain MG1655 by the Cetyltrimethyl Ammonium Bromide (CTAB) method. Yeast tRNA was purchased from Solarbio (Beijing, China). Hydroxylamine hydrochloride was purchased from Sigma-Aldrich (MO, U.S.). 0-mercaptoethanol was purchased from ZhongKeTuoZhan (Beijing, China). Triethylamine was purchased from J&K Scientific (Beijing, China). Formamide and methylene blue were purchased from Amresco (OH, U.S.). DL-1,4-dithiothreitol (DTT) was purchased from Adamas Reagent Co., Ltd (Shanghai, China). Acetonitrile (HPLC grade) was purchased from J. T. Baker (Phillipsburg, NJ, USA). L-deoxynucleoside phosphoramidites and L-dNTPs were purchased from Chem-Genes (Wilmington, MA, USA). Superscript III high-fidelity reverse transcriptase was purchased from Thermo Fisher Scientific (MA, U.S.) and Q5 high-fidelity DNA polymerase was purchased from New England Biolabs (MA, U.S.).

TABLE 1

DNA oligonucleotide sequences

| SEQ ID NO. | Oligo name | Sequence |
| --- | --- | --- |
| 1 | D-/L-FAM-primer12 | 5'-FAM-ACTACGAACGCG-3' |
| 2 | D-/L-FAM-primer11 | 5'-FAM-CGCGCTGTTAT-3' |
| 3 | D-/L-FAM-primer25 | 5'-FAM-ATGCCTGGCAGTTCCCTACTCTCGC-3' |
| 4 | D-/L-FAM-primer55 | 5'-FAM-TCACGTGCATGATAGACGGCGAAGCCGTCGAGTTGCTGTGTGCCGATGCACGTGA-3' |
| 18 | (D)-41-nt DNA template | 5'-GGACGGCATTGGATCGACGATGAGTTGGTTGGACGGCTGCG-3' |
| 19 | (D)-41-nt RNA template | 5'-GGACGGCAUUGGAUCGACGAUGAGUUGGUUGGACGGCUGCG-3' |
| 20 | (D)-21 nt DNA primer (DNA-1-P) | 5'-FAM-CGCAGCCGTCCAACCAACTCA-3' |
| 21 | (D)-21 nt RNA primer (RNA-1-P) | 5'-FAM-CGCAGCCGUCCAACCAACUCA-3' |

TABLE 1-continued

DNA oligonucleotide sequences

| SEQ ID NO. | Oligo name | Sequence |
| --- | --- | --- |
| 5 | (L)-46-nt L-RNA | 5'-GGAUCGAAAGAUUUCCGCAUCCCCGAAAGGGUACAUGGCGUUAGGU-3' |
| 22 | (L)-15-nt DNA primer | 5'-FAM-ACCTAACGCCATGTA-3' |
| 23 | (L)-FAM-PCR-R-primer | 5'-FAM-ATGCCTGGCAGTTCCCTACTCTCGC-3' |
| 24 | (L)-PCR-F-primer | 5'-TGCCTGGCGGCAGTAGCGC-3' |
| 25 | (L)-120-nt DNA template | 5'-ATGCCTGGCAGTTCCCTACTCTCGCATGGGGAGACCCCACACTACCATCGGCGCTACGGCGTTTCACTTCTGAGTTCGGCATGGGGTCAGGTGGGACCACCGCGCTACTGCCGCCAGGCA-3' |
| 26 | (L)-120-nt 5S RNA template (a transcription product of SEQ ID NO: 25) | 5'-FAM-UGCCUGGCGGCAGUAGCGCGGUGGUCCCACCUGACCCCAUGCCGAACUCAGAAGUGAAACGCCGUAGCGCCGAUGGUAGUGUGGGGUCUCCCCAUGCGAGAGUAGGGAACUGCCAGGCAU-3' |
| 27 | (L) 25 nt DNA Primer (for RT of L-5S rRNA) | 5'-Cy5-ATGCCTGGCAGTTCCCTACTCTCGC-3' |
| 28 | (D)-120-nt DNA (marker) | 5'-Cy5-ATGCCTGGCAGTTCCCTACTCTCGCATGGGGAGACCCCACACTACCATCGGCGCTACGGCGTTTCACTTCTGAGTTCGGCATGGGGTCAGGTGGGACCACCGCGCTACTGCCGCCAGGCA3' |
| 29 | (L) 5S rRNA-PCR-F primer | 5'-TGCCTGGCGGCAGTAGCGC-3' |
| 30 | (L) 5S rRNA-PCR-R primer | 5'-ATGCCTGGCAGTTCCCTACTCTCGC-3' |
| 31 | (L) 76 nt tRNA template | 5'-GGGUCGUUAGCUCAGUUGGUAGAGCAGUUGACUUUUAAUCAAUUGGUCGCAGGUUCGAAUCCUGCACGACCCACCA-3' |
| 32 | (L)-FAM-14 nt DNA primer (for RT of L-76 nt tRNA) | 5'-FAM-TGGTGGGTCGTGCA-3' |
| 33 | (L) 18 nt PCR-F primer (for amplifying 76 nt RT DNA) | 5'-GGGTCGTTAGCTCAGTTG-3' |
| 34 | (L) 14 nt PCR-R primer (for amplifying 76 nt RT DNA) | 5'-TGGTGGGTCGTGCA-3' |
| 35 | (L) 18 nt PCR-F primer (for amplifying 76 nt RT DNA) | 5'-FAM-GGGTCGTTAGCTCAGTTG-3' |
| 36 | (L)-76 nt DNA (a reverse transcription product of SEQ ID NO: 31) | 5'-TGGTGGGTCGTGCAGGATTCGAACCTGCGACCAATTGATTAAAAGTCAACTGCTCTACCAACTGAGCTAACGACCC-3' |

C+T cleavage reaction by hydrazine—An aliquot of 2 µl FAM-labelled primer (10 µM) was mixed with 3 µg carrier *E. coli* genomic DNA and kept on ice. The mixture was denatured by heating to 95° C. for 2 min followed by quick chilling on ice. An aliquot of 40 µl 80% hydrazine hydrate was added and the mixture was incubated at 45° C. for 18 minutes (reduced to 10 minutes for the 25-nt sequence and to 5 minutes for the 55-nt sequence). The reaction was quenched by adding 200 µl 0.3 M sodium acetate, 2 µl glycogen (10 mg/ml), 2 µl EDTA (10 mM, pH 8.0), 5 µl yeast tRNA (10 mg/ml), and 1 ml absolute ethanol, and the mixture was chilled in liquid nitrogen for 10 minutes. The processed DNA was precipitated by centrifugation at 12,000 rpm for 10 minutes and washed by 1 ml absolute ethanol. The residual ethanol was removed by evaporation, and the pellet was dissolved into 120 µl 1 M piperidine and incubated at 90° C. for 50 minutes. Following lyophilization, the remaining pellet was dissolved in a denaturation buffer containing 98% formamide, 0.25 mM EDTA, and 0.0125% SDS. The products were analyzed by 10% or 20% PAGE in 8 M urea and scanned by a Typhoon Trio+ system operated under FAM mode. Gel quantitation was performed by the ImageQuantTL 7.0 software with 1D gel analysis package.

C-specific cleavage reaction by NH$_2$OH—HCl—An aliquot of 2 µl FAM-labelled primer (10 µM) was mixed with 3 µg carrier *E. coli* genomic DNA and kept on ice. The mixture was denatured by heating to 95° C. for 2 minutes followed by quick chilling on ice. An aliquot of 40 µl 4 M NH$_2$OH—HCl (pH adjusted to 6.0 by trimethylamine) was added and the mixture was incubated at 25° C. for 20 minutes (reduced to 10 minutes for the 25-nt sequence and to 1 minute at 90° C. for the 55-nt sequence). The reaction was quenched by adding 200 µl 0.3 M sodium acetate, 2 µl glycogen (10 mg/ml), 2 µl EDTA (10 mM, pH 8.0), 5 µl yeast tRNA (10 mg/ml), and 1 ml absolute ethanol; and the mixture was chilled in liquid nitrogen for 10 minutes. The processed DNA was precipitated by centrifugation at 12,000 rpm for 10 minutes and washed by 1 ml absolute ethanol. The residual ethanol was removed by evaporation, and the pellet was dissolved into 100 µl 1 M piperidine and incubated at 90° C. for 30 minutes. Following lyophilization, the remaining pellet was dissolved in a denaturation buffer containing 98% formamide, 0.25 mM EDTA, and 0.0125% SDS. The products were analyzed by 10% or 20% PAGE in 8 M urea and scanned by a Typhoon Trio+ system operated under FAM mode. Gel quantitation was performed by the ImageQuantTL 7.0 software with 1D gel analysis package.

A+G cleavage reaction by formic acid—An aliquot of 2 µl FAM-labelled primer (10 µM) was mixed with 3 µg carrier *E. coli* genomic DNA and kept on ice. An aliquot of 40 µl 80% formic acid was added and the mixture was incubated at 25° C. for 30 minutes (formic acid concentration reduced to 66% and incubation time reduced to 10 minutes for the 25-nt sequence and to 3 minutes for the 55-nt sequence). The reaction was quenched by adding 200 µl 0.3 M sodium acetate, 2 µl glycogen (10 mg/ml), 5 µl yeast tRNA (10 mg/ml), and 1 ml absolute ethanol; and the mixture was chilled in liquid nitrogen for 10 minutes. The processed DNA was precipitated by centrifugation at 12,000 rpm for 10 minutes and washed by 1 ml absolute ethanol. The residual ethanol was removed by evaporation, and the pellet was dissolved into 100 µl, 1 M piperidine and incubated at 90° C. for 30 minutes. Following lyophilization, the remaining pellet was dissolved in a denaturation buffer containing 98% formamide, 0.25 mM EDTA, and 0.0125% SDS. The products were analyzed by 10% or 20% PAGE in 8 M urea and scanned by a Typhoon Trio+ system operated under FAM mode. Gel quantitation was performed by the ImageQuantTL 7.0 software with 1D gel analysis package.

G-specific cleavage reaction by UV with methylene blue—An aliquot of 2 µl FAM-labelled primer (10 µM) was mixed with 3 µg carrier *E. coli* genomic DNA and kept on ice. The mixture was denatured by heating to 95° C. for 2 minutes followed by quick chilling on ice. An aliquot of 20 µl 0.1% (m/v) methylene blue was added and the mixture were exposed to a handheld UV lamp at a distance of 10 cm for 2 minutes (exposure time increased to 4 minutes for the 25-nt sequence). The reaction was quenched by adding 200 µl 0.3 M sodium acetate, 2 µl glycogen (10 mg/ml), 5 µl yeast tRNA (10 mg/ml), and 1 ml absolute ethanol; and the mixture was chilled in liquid nitrogen for 10 minutes. The processed DNA was precipitated by centrifugation at 12,000 rpm for 10 minutes and washed by 1 ml absolute ethanol. The residual ethanol was removed by evaporation, and the pellet was dissolved into 100 µl 1 M piperidine and incubated at 90° C. for 30 minutes. Following lyophilization, the remaining pellet was dissolved in a denaturation buffer containing 98% formamide, 0.25 mM EDTA, and 0.0125% SDS. The products were analyzed by 20% PAGE in 8 M urea and scanned by a Typhoon Trio+ system operated under FAM mode. Gel quantitation was performed by the ImageQuantTL 7.0 software with 1D gel analysis package.

A>C cleavage reaction by NaOH—An aliquot of 2 µl FAM-labelled primer (10 µM) was mixed with 3 µg carrier *E. coli* genomic DNA and kept on ice. An aliquot of 20 µl 1.5 M NaOH/1 mM EDTA was added and the mixture was incubated at 90° C. for 12 minutes. The reaction was quenched by adding 100 µl 1 M sodium acetate, 2 µl glycogen (10 mg/ml), 5 µl yeast tRNA (10 mg/ml), and 1 ml absolute ethanol, and the mixture was chilled in liquid nitrogen for 10 minutes. The processed DNA was precipitated by centrifugation at 12,000 rpm for 10 minutes and washed by 1 ml absolute ethanol. The residual ethanol was removed by evaporation, and the pellet was dissolved into 100 µl 1 M piperidine and incubated at 90° C. for 30 minutes. Following lyophilization, the remaining pellet was dissolved in a denaturation buffer containing 98% formamide, 0.25 mM EDTA, and 0.0125% SDS. The products were analyzed by 10% or 20% PAGE in 8 M urea and scanned by a Typhoon Trio+ system operated under FAM mode. Gel quantitation was performed by the ImageQuantTL 7.0 software with 1D gel analysis package.

Reverse transcription by Dpo4-All D- or L-primers, 41-nt D-DNA template, 46-nt L-RNA template, 120-nt L-rRNA template and 76-nt L-tRNA template were chemically synthesized (SEQ ID Nos: 1-5, 18-22, 26-27 and 31-32). All the D-primer and D-template extension reactions were performed in 10 µl reaction systems containing 50 mM HEPES (pH 7.5), 5 mM MgCl2, 50 mM NaCl, 0.1 mM EDTA, 5 mM DTT, 10% glycerol, 0.1 mg/ml BSA, dNTPs or NTPs (each at 0.8 mM for the natural system, and each at 0.2 mM for the mirror-image system), 0.5 µM DNA or RNA primer, 1 or 2 µM RNA or DNA template, 1 U/µl RNase inhibitor (for D-RNA) and 500 nM Dpo4-5m (SEQ ID NO: 10), Dpo4-6m-Y12A (SEQ ID NO: 14), Dpo4-6m-Y12G (SEQ ID NO: 16) or Dpo-6m-Y12S (SEQ ID NO: 12). All the L-primer and L-template extension reactions were performed in 20 µl reaction systems containing 50 mM HEPES (pH 7.5), 5 mM MgCl2, 50 mM NaCl, 0.1 mM EDTA, 5 mM DTT, 10% glycerol, 0.1 mg/ml BSA, dNTPs or NTPs (each at 0.8 mM for the natural system, and each at 0.2 mM for the mirror-image system), 0.5 µM DNA or RNA primer, 1 or 2 µM RNA or DNA template and ~25 µg/ml Dpo4-5m (SEQ ID NO: 10). Prior to the addition of polymerase, the reaction system was heated to 95° C. for 2 minutes and slowly cooled to RT or 4° C. for annealing. Primer extension reactions took place at 65° C. for up to 36 hours, as indicated. The reactions were stopped by adding loading buffer containing 98% formamide, 0.25 mM EDTA, and 0.0125% SDS, and the products were analyzed by 12% denaturing PAGE in 8 M urea and scanned by a Typhoon Trio+ system operated under FAM or Cy5 mode. The D-products were digested by 1 or 5 U RNase H or DNase I at 37° C. for 30 minutes.

MI-PCR of chemically synthesized L-DNA by d-Dpo4-5m—120-nt L-DNA template (SEQ ID NO: 25), L-FAM-PCR-R-primer (SEQ ID NO: 23) and L-PCR-F-primer (SEQ ID NO: 24) were chemically synthesized. The amplification reactions were performed in a 50 µl reaction system containing 50 mM HEPES (pH 7.5), 5 mM MgCl2, 50 mM NaCl, 0.1 mM EDTA, 5 mM DTT, 10% glycerol, 3% DMSO, 0.1 mg ml-1 BSA, 100 or 200 µM (each) L-dNTPs, 0.5 or 1 µM L-FAM-PCR-R-primer (SEQ ID NO: 23), 0.5 uM L-PCR-F-primer (SEQ ID NO: 24), 10 nM 120-nt L-DNA template (SEQ ID NO: 25), and 500 nM d-Dpo4-5m polymerase (SEQ ID NO: 10). MI-PCR was performed for 40 cycles. The products were analysed by 3% sieving agarose gel electrophoresis and were stained by GoldView. 800 µl of the PCR reaction system was recovered by 12% PAGE in 8M urea and used for chemical sequencing.

MI-PCR of reverse transcribed L-DNA—The amplification reaction was performed in buffer containing 50 mM HEPES (pH 7.5), 5 mM MgCl2, 50 mM NaCl, 0.1 mM EDTA, 5 mM DTT, 10% glycerol, 3% DMSO, 0.1 mg/ml BSA, 200 µM (each) L-dNTPs, 1 µM (each) L-DNA primers, 1 µl mirror-image reverse transcription product, and ~500 nM D-Dpo4-5m (SEQ ID NO: 10). Prior to the addition of polymerase, the reaction system was heated to 95° C. for 2 minutes and slowly cooled to 86° C. The PCR program settings of 120-nt L-5S rRNA were 86° C. for 3 min (initial denaturation), 86° C. for 30 s (denaturation), 58° C. for 3 min (annealing), and 65° C. for 14 min (extension) for up to 35 cycles. The PCR program settings of 76-nt L-tRNA were 86° C. for 3 min (initial denaturation), 86° C. for 30 s (denaturation), 50° C. for 3 min (annealing), and 65° C. for 8 min (extension) for up to 40 cycles. The PCR products were digested by 1 U DNase I (New England Biolabs, U.S.) at 37° C. for 5 minutes. All the products were analyzed by 3% sieving agarose gel electrophoresis and stained by GoldView (Solarbio, China). The negative controls were performed without a polymerase or a reverse transcription product.

Example 1

L-DNA Sequencing Using Nuclease-Specific Chemical Modification and Subsequent Cleavage at the Modified Nucleotides The chemical sequencing approach was first tested on a 12-nucleotides (nt) L-DNA oligo with fluorescein amidite (FAM) label at the 5' end (SEQ ID NO: 1). A fluorescent end-labelling and not a radioactive labelling was used in part because it is impractical to radioactively label L-DNA without a mirror-image polynucleotide kinases. The C+T reaction was carried out by hydrazine at 45° C., the C-specific reaction with hydroxylamine hydrochloride (pH 6.0) at 25° C., the A+G cleavage reaction by formic acid at 25° C., and the G-specific reaction with methylene blue under ultraviolet (UV) irradiation, followed by strand scission adjacent to the modified site by treatment with strong alkali (FIG. 1A). As the UV absorption spectrum of methylene blue is different from that of FAM (FIG. 2), UV was used at 254 nm to specifically excite methylene blue. Additionally, an un-labelled *E. coli* genomic DNA was used as a carrier DNA during the sequencing. The final products were separated using polyacrylamide gel electrophoresis (PAGE) and the bands representing products comprising the FAM-label were visualized by a Typhoon Trio+ system operated under FAM mode (FIG. 1B).

During the sequencing, several faint, non-specific bands were observed, particularly with the C+T and C-specific reactions, which also has been observed in previous studies on D-DNA chemical sequencing[12]. Additionally, photooxidation in the G-specific reaction tends to be less selective owing to the highly active singlet oxygens[14]. To overcome potential misreading of the L-DNA sequences, the C+T and C-specific reactions was optimized by carefully adjusting the pH in the reaction systems, which is key to the reduction of non-specific bands[8,13]. Moreover, the major bands in the A+G reaction is known to be highly reliable and can help to minimize the possibility of misreading the sequencing results[13]. Taken together, with these optimizations and adjusting reaction conditions (Table 2 below), the sequences of the 12-nt L-DNA oligo was reliably determined by PAGE analysis and sequencing chromatogram (FIGS. 1B and 1C). Similar degradation patterns were observed with a 12-nt D-DNA oligo with the same sequence (SEQ ID NO: 1) but opposite circular dichroism (CD) spectrum (FIG. 1D and FIGS. 3A-C).

Next, to test the method on L-DNA oligos of other sequences and lengths, sequencing of two FAM-labelled L-DNA oligos of 11-nt (SEQ ID NO: 2) and 25-nt (SEQ ID NO: 3) was performed using the same C+T, C-, A+G, and G-specific reactions. The final products were analyzed by PAGE scanned by a Typhoon Trio+ system operated under FAM mode. As shown in FIGS. 4A-C and 5A-C, with optimization of the reaction conditions by adjusting the reagent concentration and reaction time to reduce the non-specific bands (Table 2 below), one can accurately read the sequences of the 11-nt (SEQ ID NO: 2) and 25-nt (SEQ ID NO: 3) L-DNA oligos by PAGE analysis and sequencing chromatogram.

Encouraged by the successful sequencing of short L-DNA oligos, the ability of the method to sequence longer L-DNA molecule with therapeutic applications was examined. To this end, a previously reported 55-nt L-DNA aptamer (SEQ ID NO: 4) was chosen as a model (FIG. 6A), which has been shown to bind natural vasopressin and thus has potential to become a nuclease-resistant vasopressin antagonist[1]. Since the efficacy of the G-specific reaction is prone to be affected by the formation of secondary structures[11], a A>C reaction by NaOH at 90° C. was applied instead of the G-specific reaction[9]. The reaction conditions were optimized by adjusting the reagent concentration, temperature, and reaction time to reduce the non-specific bands (Table 2 below). A multiple loading strategy was also applied through which four sections of the L-DNA sequence were separately analyzed by polyacrylamide gels of different concentrations for better separation of the bands. As shown in FIG. 6C, using these modifications to the methodology, the full-length L-DNA aptamer sequence (SEQ ID NO: 4) was validated by combining the results from four sequencing gels. In the same manner, a 120-nt L-DNA sequence (SEQ ID NO: 25) was also successfully sequenced (FIGS. 9A-B).

TABLE 2

Reaction conditions for sequencing L-DNA molecules of different lengths

| Base-specific reaction | Reagent and concentration | Reaction condition (11 or 12 nt) | Reaction condition (25 nt) | Reaction condition (55 nt) | Reaction condition (120 nt) |
|---|---|---|---|---|---|
| C + T | 50% (m/m) hydrazine | 18 min (45° C.) | 10 min (45° C.) | 5 min (45° C.) | 2.5 min (45° C.) |
| C | 4M NH$_2$OH—HCl | 20 min (RT) | 10 min (RT) | 50 s (90° C.) | 25 s (90° C.) |
| A + G | 66-80% (v/v) formic acid | 40 min (RT) | 10 min (RT) | 3 min (RT) | 2 min (RT) |
| G | 0.1% (m/v) methylene blue under UV | 2 min (RT) | 4 min (RT) | — | — |
| A > C | 1.5M NaOH/1 mM EDTA | — | — | 12 min (90° C.) | 5 min (90° C.) |

Example 2

Reverse Transcription of RNA Using Dpo4

The thermostable *Sulfolobus solfataricus* P2 DNA polymerase IV (Dpo4) has been shown to catalyze replication of DNA and transcription of DNA into RNA[e.g. 23]. The present inventors have tested whether Dpo4 possesses a reverse transcription activity.

To this end, the ability of Dpo4 to reverse transcribe RNA was evaluated by examining the natural, L-polymerase with a 5' FAM-labeled D-DNA primer (SEQ ID NO: 20) and a synthetic D-RNA template (SEQ ID NO: 19) supplied with D-dNTPs. A fully extended product was obtained following 1 hour of incubation, suggesting that the Dpo4 containing 5 point mutations, denoted herein as Dpo4-5m (SEQ ID NO: 10) does indeed have reverse transcription activity, while the other Dpo4 mutants (SEQ ID Nos: 12, 14, 16) possess much lower efficiency (FIGS. 7A-D). Encouraged by the successful reverse transcription of short synthetic RNA, reverse transcription of a L-46-nt RNA ribozyme (SEQ ID NO: 5) with a 5' FAM-labeled L-DNA primer (SEQ ID NO: 22) and d-Dpo4-5m (SEQ ID NO: 10) was tested (FIG. 8). The fidelity of the reverse transcription by Dpo4-5m with the natural system was also examined and an error rate of ~2.6% was measured (Table 3 below).

TABLE 3

Fidelity of reverse transcription by Dpo4-5m.

| Total sequenced bases | Deletion | Insertion | Mutation | Error rate |
|---|---|---|---|---|
| 3342 bp | 18 bp | 2 bp | 66 bp | 2.6% |

In addition, purified 5'-FAM-labelled L-120-nt 5S (L-5S) rRNA (SEQ ID NO: 26) was used as a template, and 5'-Cy5-labelled L-DNA (SEQ ID NO: 27) as a primer, which was extended to full length by D-Dpo4-5m (SEQ ID NO: 10) following incubation for 36 hours (FIGS. 10-11). As expected, the L-DNA products were not digested by natural DNase I (FIG. 10). Notably, the L-RNA template was also extended (FIG. 10), likely due to non-templated nucleotide addition to the 3'-terminus by Dpo4-5m.

The broad application of reverse transcription in molecular biology has been propelled by the introduction of RT-PCR. Hence, in the next step, the ability of D-Dpo4 to amplify the reverse transcribed 120-nt L-DNA was evaluated. As shown in FIG. 12, PCR amplification of the reverse transcribed L-DNA resulted in a target band in sieving agarose gel electrophoresis with the expected length of 120 bp, which increased in intensity with cycle numbers of up to 35, while the negative controls without polymerase or reverse transcription product resulted in no amplification product. Notably, the same D-Dpo4-5m (SEQ ID NO: 10) was used for both mirror-image reverse transcription and PCR, thus simplifying the system in that it can be achieved using one D-polymerase, minimizing experimental cost and effort required to meet the future needs of mirror-image molecular applications.

Following, the present inventors tested whether the reverse transcribed and amplified L-DNA could be used for sequencing. To this end, reverse transcription was effected with a synthetic 76-nt L-tRNA template (SEQ ID NO: 31) and a 5'-FAM-labelled L-DNA primer (SEQ ID NO: 32) supplied with L-dNTPs, which was extended to full length following incubation for up to 24 hours (FIG. 13A). The reverse transcribed L-DNA was successfully amplified by mirror-image PCR (MI-PCR), and the amplification product was indeed resistant to natural DNase I digestion (FIG. 13B). Following, the same mirror-image PCR experiment was effected except that one of the primers was FAM-labelled at the 5'-terminus (SEQ ID NO: 35), followed by sequencing using a set of nucleobase-specific chemical cleavage reactions, as described in Example 1 hereinabove. As shown in FIG. 13C, the expected sequence of the reverse transcribed and PCR amplified L-DNA was determined (SEQ ID NO: 36).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited Throughout the Application

1. Williams, K. P. et al. Bioactive and nuclease-resistant 1-DNA ligand of vasopressin. *Proceedings of the National Academy of Sciences* 94, 11285-11290 (1997).
2. Yatime, L. et al. Structural basis for the targeting of complement anaphylatoxin C5a using a mixed L-RNA/L-DNA aptamer. *Nature Communications* 6, 6481, (2015).
3. Jiang, W. et al. Mirror-image polymerase chain reaction. *Cell discovery* 3, 17037 (2017).
4. Xu, W. et al. Total chemical synthesis of a thermostable enzyme capable of polymerase chain reaction. *Cell discovery* 3, 17008, (2017).
5. Wang, Z., Xu, W., Liu, L. & Zhu, T. F. A synthetic molecular system capable of mirror-image genetic replication and transcription. *Nat Chem* 8, 698-704, (2016).
6. Pech, A. et al. A thermostable d-polymerase for mirror-image PCR. *Nucleic Acids Res* 45, 3997-4005, (2017).
7. Derrington, I. M. et al. Subangstrom single-molecule measurements of motor proteins using a nanopore. *Nature biotechnology* 33, 1073-1075, (2015).
8. Rubin, C. M. & Schmid, C. W. Pyrimidine-specific chemical reactions useful for DNA sequencing. *Nucleic Acids Res* 8, 4613-4619 (1980).
9. Maxam, A. M. & Gilbert, W. A new method for sequencing DNA. *Proc Natl Acad Sci USA* 74, 560-564 (1977).
10. Rosenthal, A., Schwertner, S., Hahn, V. & Hunger, H. D. Solid-phase methods for sequencing of nucleic acids I. Simultaneous sequencing of different oligodeoxyribonucleotides using a new, mechanically stable anion-exchange paper. *Nucleic Acids Res* 13, 1173-1184 (1985).
11. Friedmann, T. & Brown, D. M. Base-specific reactions useful for DNA sequencing: methylene blue-sensitized photooxidation of guanine and osmium tetraoxide modification of thymine. *Nucleic Acids Res* 5, 615-622 (1978).

12. Banaszuk, A. M., Deugau, K. V., Sherwood, J., Michalak, M. & Glick, B. R. An efficient method for the sequence analysis of oligodeoxyribonucleotides. *Analytical biochemistry* 128, 281-286 (1983).
13. Pichersky, E. DNA Sequencing by the Chemical Method. In: Harwood A. J. (eds) Basic DNA and RNA Protocols. Methods in Molecular Biology. 58 (1996).
14. Saito, I., Sugiyama, H., Matsuura, T., Ueda, K. & Komano, T. A new procedure for determining thymine residues in DNA sequencing. Photoinduced cleavage of DNA fragments in the presence of spermine. *Nucleic Acids Res* 12, 2879-2885 (1984).
15. Bjorkbom, A. et al. Bidirectional Direct Sequencing of Noncanonical RNA by Two-Dimensional Analysis of Mass Chromatograms. *J Am Chem Soc* 137, 14430-14438, (2015).
16. Turner, J. J., Hoos, J. S., Vonhoff, S. & Klussmann, S. Methods for L-ribooligonucleotide sequence determination using LCMS. *Nucleic Acids Res* 39, e147, (2011).
17. Franca, L. T., Carrilho, E. & Kist, T. B. A review of DNA sequencing techniques. Quarterly reviews of biophysics 35, 169-200 (2002).
18. Ansorge, W. et al. Non-radioactive automated sequencing of oligonucleotides by chemical degradation. *Nucleic Acids Res* 16, 2203-2206 (1988).
19. Sanger, F., Nicklen, S. & Coulson, A. R. DNA sequencing with chain-terminating inhibitors. *Proc Natl Acad Sci USA* 74, 5463-5467 (1977).
20. Zuker, M. Mfold web server for nucleic acid folding and hybridization prediction. *Nucleic Acids Res* 31, 3406-3415 (2003).
21. Lee, H. R. & Johnson, K. A. Fidelity and processivity of reverse transcription by the human mitochondrial DNA polymerase. *The Journal of biological chemistry* 282, 31982-31989, (2007).
22. Jiang, W. et al. Mirror-image polymerase chain reaction. *Cell discovery* 3, 17037, (2017).
23. Wang, Z., Xu, W., Liu, L. & Zhu, T. F. A synthetic molecular system capable of mirror-image genetic replication and transcription. *Nat Chem* 8, 698-704, (2016).

What is claimed is:

1. A method of sequencing a nucleic acid sequence comprising L-nucleotides, the method comprising:
   (i) subjecting the nucleic acid sequence comprising the L-nucleotides to a chemical sequencing method using a chemical selected from the group consisting of Dimethyl sulfate, Methylamine, Diethyl pyrocarbonate, Methylene blue, Potassium chloropalladate, Sodium hydroxide, Osmium tetroxide, Spermine, potassium permanganate, Hydrazine, hydrazine hydrate, Hydroxylamine hydrochloride, and Formic acid;
   subjecting the nucleic acid sequence comprising the L-nucleotides to a chemical sequencing method, wherein said nucleic acid sequence comprises more than 120 nucleotides and up to 1000 nucleotides in length;
   (iii) subjecting the nucleic acid sequence comprising the L-nucleotides to a chemical sequencing method, wherein said chemical sequencing method comprises gel-electrophoresis to determine said nucleic acid sequence; and/or
   (iv) labeling at a 5' terminus or 3' terminus of the nucleic acid sequence comprising the L-nucleotides with 5-iodoacetamidofluorescein, so as to obtain a labeled nucleic acid sequence comprising the L-nucleotides; and subjecting said labeled nucleic acid sequence comprising the L-nucleotides to a chemical sequencing method.

2. The method of claim 1, wherein said chemical sequencing method comprises using a chemical selected from the group consisting of Dimethyl sulfate, Methylamine, Diethyl pyrocarbonate, Methylene blue, Potassium chloropalladate, Sodium hydroxide, Osmium tetroxide, Spermine, potassium permanganate, Hydrazine, hydrazine hydrate, Hydroxylamine hydrochloride, and Formic acid.

3. The method of claim 1, wherein said chemical is selected from the group consisting of Methylene blue, Sodium hydroxide, Hydroxylamine hydrochloride, Formic acid and hydrazine hydrate.

4. The method of claim 1, wherein said nucleic acid sequence comprises more than 150 nucleotides and up to 1000 nucleotides in length.

5. The method of claim 1, wherein said method comprises labeling said nucleic acid sequence at a 5' terminus or 3' terminus with fluorescein amidite (FAM), 5-iodoacetamidofluorescein or biotin.

6. The method of claim 1, wherein said method comprises labeling said nucleic acid sequence at a 5' terminus or 3' terminus with fluorescein amidite (FAM) or 5-iodoacetamidofluorescein.

7. The method of claim 1, wherein said labeling is at a 5' terminus.

8. The method of claim 1, wherein said method does not comprise mass-spectrometry (MS).

9. The method of claim 1, wherein said nucleic acid sequence comprises deoxyribose nucleotides.

10. The method of claim 1, wherein said nucleic acid sequence comprises ribose nucleotides.

11. The method of claim 1, wherein said chemical sequencing method comprises:
    (a) labeling a plurality of molecules of said nucleic acid sequence at a 5' terminus or 3' terminus of said plurality of molecules with a label;
    (b) partially modifying said plurality of molecules following said (a) using a nucleobase-specific chemical agent such that upon cleaving said plurality of molecules adjacent to modified nucleobases a plurality of fragments of said nucleic acid sequence comprising said label are obtained;
    (c) cleaving said plurality of molecules following said (b) adjacent to modified nucleobases; and
    (d) determining said modified nucleobases positions in said nucleic acid sequence according to lengths, masses and/or charges of fragments produced by said cleaving and comprising said label.

12. The method of claim 11, wherein said (b) is effected in at least 3 separate reaction mixtures so as to create a set of fragments comprising said label differing by a single nucleotide in length.

13. The method of claim 1, wherein said nucleic acid sequence comprising the L-nucleotides is reverse transcribed optionally with a *Sulfolobus solfataricus* P2 DNA polymerase IV (Dpo4).

14. The method of claim 1, wherein said nucleic acid sequence consists of L-nucleotides.

15. The method of claim 1, wherein said nucleic acid sequence consist of L-deoxyribonucleotides.

16. A method of sequencing a nucleic acid sequence consisting of L-deoxyribonucleotides, the method comprising subjecting the nucleic acid sequence consisting of the L-deoxyribonucleotides to a chemical sequencing method, wherein said nucleic acid sequence comprises more than 120 nucleotides and up to 1000 nucleotides in length.

17. The method of claim 16, wherein said chemical sequencing method comprises:
    (a) labeling a plurality of molecules of said nucleic acid sequence at a 5' terminus or 3' terminus of said plurality of molecules with a label;

(b) partially modifying said plurality of molecules following said (a) using an achiral nucleobase-specific chemical agent such that upon cleaving said plurality of molecules adjacent to modified nucleobases a plurality of fragments of said nucleic acid sequence comprising said label are obtained;

(c) cleaving said plurality of molecules following said (b) adjacent to modified nucleobases; and (d) determining said modified nucleobases positions in said nucleic acid sequence according to lengths, masses and/or charges of fragments produced by said cleaving and comprising said label.

18. The method of claim 16, wherein said nucleic acid sequence comprises more than 150 nucleotides and up to 1000 nucleotides in length.

19. The method of claim 16, wherein said method further comprises labeling said nucleic acid sequence at a 5' terminus or 3' terminus with fluorescein amidite (FAM), 5-iodoacetamidofluorescein or biotin.

20. The method of claim 19, wherein said labeling is at a 5' terminus.

21. The method of claim 16, wherein said method comprises gel-electrophoresis to determine said nucleic acid sequence.

22. The method of claim 16, wherein said nucleic acid sequence consisting of the L-deoxyribonucleotides is reverse transcribed optionally with a *Sulfolobus solfataricus* P2 DNA polymerase IV (Dpo4).

* * * * *